(12) United States Patent
Zhou et al.

(10) Patent No.: US 7,482,343 B2
(45) Date of Patent: Jan. 27, 2009

(54) COMPOUNDS, METHODS AND COMPOSITIONS

(75) Inventors: Han-Jie Zhou, Foster City, CA (US); David J. Morgans, Jr., Los Altos, CA (US); Gustave Bergnes, Pacifica, CA (US); Steven David Knight, West Chester, PA (US); Kenneth A. Newlander, West Chester, PA (US); Dashyant Dhanak, West Chester, PA (US); Nicholas D. Adams, Royersford, PA (US)

(73) Assignees: Cytokinetics, Inc., South San Francisco, CA (US); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/600,683

(22) Filed: Nov. 15, 2006

(65) Prior Publication Data

US 2007/0135432 A1    Jun. 14, 2007

Related U.S. Application Data

(63) Continuation of application No. 10/429,195, filed on May 2, 2003, now Pat. No. 7,166,595.

(60) Provisional application No. 60/379,658, filed on May 9, 2002.

(51) Int. Cl.
  *A61K 31/513* (2006.01)
  *C07D 239/36* (2006.01)

(52) U.S. Cl. ............... 514/233.8; 514/238.8; 514/258.1; 514/266.1; 514/269; 544/123; 544/253; 544/319

(58) Field of Classification Search ............... 514/233.8, 514/238.8, 258.1, 266.1, 269
  See application file for complete search history.

(56) References Cited

U.S. PATENT DOCUMENTS

| | | | |
|---|---|---|---|
| 5,264,439 A | 11/1993 | Greenlee et al. |
| 5,753,664 A | 5/1998 | Aono et al. |
| 6,136,812 A | 10/2000 | Chenard et al. |
| 6,545,004 B1 | 4/2003 | Finer et al. |
| 6,545,005 B1 | 4/2003 | Baxter et al. |
| 7,166,595 B2 | 1/2007 | Zhou et al. |
| 2003/0139457 A1 | 7/2003 | Baxter et al. |
| 2004/0242596 A1 | 12/2004 | Kim et al. |
| 2005/0197327 A1 | 9/2005 | Bergnes et al. |
| 2007/0149500 A1 | 6/2007 | Zhou et al. |

FOREIGN PATENT DOCUMENTS

| | | |
|---|---|---|
| JP | 62-135473 | 6/1987 |
| JP | 06049070 A2 | 2/1994 |
| WO | WO 02/09713 A2 | 2/2002 |
| WO | WO 02/09713 A3 | 2/2002 |
| WO | WO 03/027234 A2 | 4/2003 |
| WO | WO 03/035076 A1 | 5/2003 |
| WO | WO 03/035077 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/094839 A2 | 11/2003 |
| WO | WO 03/099211 A2 | 12/2003 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 A1 | 9/2004 |

OTHER PUBLICATIONS

Simone, Oncology: Introduction, Cecil Textbook of Medicine, 20th Edition, vol. 1, pp. 1004-1010, 1996.*
Farrell et al., PubMed Abstract (J Biol Chem 277(19):17079-87), May 2002.*
Yildiz et al., Kinesin: Walking, crawling or sliding along?, Trends in Cell Biology, vol. 15, No. 2, Feb. 2005.*
Vippagunta et al., Crystalline Solids, Advanced Drug Delivery Reviews, 48, pp. 3-26, 2001.*
West, Solid Solutions, Chapter 10, pp. 358 and 365, 1988.*
Ulrich, Crystallization: 4. Crystal Characteristics, Kirk-Othmer Encyclopedia of Chemical Technology, Aug. 2002.*
Hart et al. "Synthesis of (-)-Alantrypinone," Tet. Lett. 40: 5429-5432 (1999).
Hart et al. "Synthesis of ent-Alantrypinone" J. Am. Chem. Soc. 123: 5892-5899 (2001).
International Search Report and Written Opinion mailed Dec. 6, 2004, for PCT Application No. PCT/US04/01279, filed Jan. 20, 2004.
International Search Report mailed Jul. 16, 2004, for PCT Application No. PCT/US03/13627, filed May 2, 2003.
Office Action mailed Apr. 27, 2005, for U.S. Appl. No. 10/429,195, filed May 2, 2003.
International Preliminary Examination Report mailed May 9, 2005, for PCT/US03/13627, filed May 2, 2003.
International Search Report and Written Opinion mailed Apr. 28, 2005, for PCT Application No. PCT/US04/36253, filed Nov. 2, 2004.
International Search Report and Written Opinion mailed Jun. 14, 2005, for PCT Application No. PCT/US04/36853, filed Nov. 5, 2004.
Sauter et al., Caplus Abstract No. 87:84931 (1977).
Uchida et al., Caplus Abstract No. 81:152142 (1974).
Yamada et al., Caplus Abstract No. 134:252363 (2001).
Matsuoka et al., Caplus Abstract No. 133:150920 (2000).
Nugent et al., Caplus Abstract No. 123:143921 (1995).
De Melo et al., Caplus Abstract No. 117:143023 (1992).
Irikura et al., Caplus Abstract No. 105:42834 (1986).
Kyorin Pharmaceutical Co., Ltd., Caplus Abstract No. 103:87901 (1985).
Shuto et al., Caplus Abstract No. 90:72134 (1979).

(Continued)

*Primary Examiner*—Deepak Rao
(74) *Attorney, Agent, or Firm*—Finnegan, Henderson, Farabow, Garrett & Dunner, LLP

(57) ABSTRACT

Compounds useful for treating cellular proliferative diseases and disorders by modulating the activity of KSP are disclosed.

17 Claims, No Drawings

OTHER PUBLICATIONS

Katagiri et al., Caplus Abstract No. 51536 (1984).
Hegrand et al., Caplus Abstract No. 80:95873 (1974).
Witkop et al., Caplus Abstract No. 75:77191 (1971).
Coleman et al. "Inhibitors of the mitotic kinesin spindle protein" *Expert Opin. Ther. Patents* 14(12): 1659-1667 (2004).

Office Action mailed Dec. 5, 2005, for U.S. Appl. No. 10/429,195, filed May 2, 2003.
Notice of Allowance mailed Aug. 23, 2006, for U.S. Appl. No. 10/429,195, filed May 2, 2003.
Office Action mailed Jun. 19, 2007, for U.S. Appl. No. 10/980,627, filed Nov. 2, 2004.

* cited by examiner

COMPOUNDS, METHODS AND COMPOSITIONS

CROSS-REFERENCE TO RELATED PATENT APPLICATIONS

This application is a continuation of U.S. application Ser. No. 10/429,195, filed May 2, 2003 now U.S. Pat. No. 7,166,595, which claims the benefit of U.S. Provisional Application No. 60/379,658, filed May 9, 2002; both of which are incorporated herein by reference in their entirety for all purposes.

FIELD OF THE INVENTION

This invention relates to compounds which are inhibitors of the mitotic kinesin KSP and are useful in the treatment of cellular proliferative diseases, for example cancer, hyperplasias, restenosis, cardiac hypertrophy, immune disorders, fungal disorders, and inflammation.

BACKGROUND OF THE INVENTION

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426), and a fragment of the KSP gene (TRIP5) has been described (Lee, et al., Mol Endocrinol., 9:243-54 (1995); GenBank accession number L40372). *Xenopus* KSP homologs (Eg5), as well as Drosophila KLP61 F/KRP1 30 have been reported.

Mitotic kinesins, including KSP, are attractive targets for the discovery and development of novel antimitotic chemotherapeutics. Accordingly, it is an object of the present invention to provide compounds, compositions and methods useful in the inhibition of KSP.

SUMMARY OF THE INVENTION

In accordance with the objects outlined above, the present invention provides compounds that can be used to treat cellular proliferative diseases. The compounds are KSP inhibitors, particularly human KSP inhibitors. The present invention also provides compositions comprising such compounds, and methods utilizing such compounds or compositions, which can be used to treat cellular proliferative diseases.

In one aspect, the invention relates to methods for treating cellular proliferative diseases, and for treating disorders by inhibiting the activity of KSP. The methods employ compounds represented by Formula I:

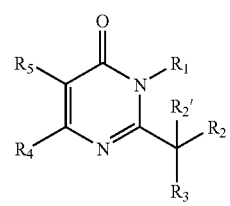

Formula I wherein:

$R_1$ is chosen from hydrogen, optionally substituted alkyl-, optionally substituted aryl-, optionally substituted aralkyl-, optionally substituted heteroaryl-, and optionally substituted heteroaralkyl-;

$R_2$ and $R_2'$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_2'$ taken together form an optionally substituted 3- to 7-membered ring;

$R_3$ is selected from the group consisting of optionally substituted imidazolyl-, optionally substituted imidazolinyl-, —$NHR_6$; —$N(R_6)(COR_7)$; —$N(R_6)(SO_2R_{7a})$; and —$N(R_6)(CH_2R_{7b})$;

$R_4$ and $R_5$ are independently chosen from hydrogen, optionally substituted alkyl-, optionally substituted alkoxy, halogen, hydroxyl-, nitro, cyano, dialkylamino, alkylsulfonyl-, alkylsulfonamido, alkylsulfanyl-, carboxyalkyl-, carboxamido, aminocarbonyl-, optionally substituted aryl-, optionally substituted aralkyl-, optionally substituted heteroaralkyl and optionally substituted heteroaryl-; or $R_4$ and $R_5$ taken together with the carbons to which they are attached form an optionally substituted 5-, 6- or 7-membered, aliphatic carbocyclic ring;

$R_6$ is chosen from hydrogen, optionally substituted alkyl-, optionally substituted aryl-, optionally substituted aralkyl-, optionally substituted heteroaralkyl-, and optionally substituted heterocyclyl-;

$R_7$ is chosen from hydrogen, optionally substituted alkyl-, optionally substituted aryl-, optionally substituted aralkyl-, optionally substituted heteroaryl-, optionally substituted heteroaralkyl-, $R_8O$— and $R_{14}$—NH—;

$R_{7a}$ is chosen from optionally substituted alkyl-, optionally substituted aryl-, optionally substituted aralkyl-, optionally substituted heteroaryl-, optionally substituted heteroaralkyl-, and $R_{14}$—NH—;

$R_{7b}$ is chosen from hydrogen, optionally substituted alkyl-, optionally substituted aryl-, optionally substituted aralkyl-, optionally substituted heteroaryl-, and optionally substituted heteroaralkyl-;

$R_8$ is chosen from optionally substituted alkyl-, optionally substituted aryl-, optionally substituted aralkyl-, optionally substituted heteroaryl-, and optionally substituted heteroaralkyl-; and $R_{14}$ is chosen from hydrogen, optionally substituted alkyl-, optionally substituted aryl-, optionally substituted aralkyl-, optionally substituted heteroaryl-, and optionally substituted heteroaralkyl-;

(Formula I including single stereoisomers and mixtures of stereoisomers);

a pharmaceutically acceptable salt of a compound of Formula I;

a pharmaceutically acceptable solvate of a compound of Formula I; or a pharmaceutically acceptable solvate of a pharmaceutically acceptable salt of a compound of Formula I.

In one aspect, the invention relates to methods for treating cellular proliferative diseases and other disorders that can be treated by inhibiting KSP by the administration of a therapeutically effective amount of a compound of Formula I; a pharmaceutically acceptable salt of a compound of Formula I; pharmaceutically acceptable solvate of a compound of Formula I; or a pharmaceutically acceptable solvate of a pharmaceutically acceptable salt of a compound of Formula I. Such diseases and disorders include cancer, hyperplasia, restenosis, cardiac hypertrophy, immune disorders, fungal disorders and inflammation.

In another aspect, the invention relates to compounds useful in inhibiting KSP kinesin. The compounds have the structures shown above in Formula I; a pharmaceutically acceptable salt of a compound of Formula I; a pharmaceutically acceptable solvate of a compound of Formula I; or a pharmaceutically acceptable solvate of a pharmaceutically acceptable salt of a compound of Formula I. The invention also relates to pharmaceutical compositions comprising: a therapeutically effective amount of a compound of Formula I; a pharmaceutically acceptable salt of a compound of Formula I; a pharmaceutically acceptable solvate of a compound of Formula I; or a pharmaceutically acceptable solvate of a pharmaceutically acceptable salt of a compound of Formula I; and one or more pharmaceutical excipients. In another aspect, the composition further comprises a chemotherapeutic agent other than a compound of the present invention.

In an additional aspect, the present invention provides methods of screening for compounds that will bind to a KSP kinesin, for example compounds that will displace or compete with the binding of a compound of the invention. The methods comprise combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods comprise combining a compound of the invention, a KSP kinesin, and at least one candidate agent and determining the effect of the candidate agent on the KSP kinesin activity.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
CBZ=carbobenzoxy=benzyloxycarbonyl
DBU=diazabicyclo[5.4.0]undec-7-ene
DCM=dichloromethane=methylene chloride=$CH_2Cl_2$
DCE=dichloroethane
DEAD=diethyl azodicarboxylate
DIC=diisopropylcarbodiimide
DIEA=N,N-diisopropylethylamine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Et=ethyl
ETOH=ethanol
Fmoc=9-fluorenylmethoxycarbonyl
GC=gas chromatography
HATU=O-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
Pfp=pentafluorophenol
PPTS=pyridinium p-toluenesulfonate
Py=pyridine
PyBroP=bromo-tris-pyrrolidino-phosphonium hexafluorophosphate rt=room temperature
sat'd=saturated
s-=secondary
t-=tertiary
TBDMS=t-butyldimethylsilyl
TES=triethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl Alkyl is intended to include linear, branched, or cyclic aliphatic hydrocarbon structures and combinations thereof, which structures may be saturated or unsaturated. Lower-alkyl refers to alkyl groups of from 1 to 5 carbon atoms, preferably from 1 to 4 carbon atoms. Examples of lower-alkyl groups include methyl-, ethyl-, propyl-, isopropyl-, butyl-, s- and t-butyl and the like. Preferred alkyl groups are those of $C_{20}$ or below. More preferred alkyl groups are those of $C_{13}$ or below. Cycloalkyl is a subset of alkyl and includes cyclic aliphatic hydrocarbon groups of from 3 to 13 carbon atoms. Examples of cycloalkyl groups include c-propyl-, c-butyl-, c-pentyl-, norbornyl-, adamantyl and the like. Cycloalkyl-alkyl- is another subset of alkyl and refers to cycloalkyl attached to the parent structure through a non-cyclic alkyl-. Examples of cycloalkyl-alkyl- include cyclohexylmethyl-, cyclopropylmethyl-, cyclohexylpropyl-, and the like. In this application, alkyl includes alkanyl-, alkenyl and alkynyl residues; it is intended to include vinyl-, allyl-, isoprenyl and the like. When an alkyl residue having a specific number of carbons is named, all geometric isomers having that number of carbons are intended to be encompassed; thus, for example, "butyl" is meant to include n-butyl-, sec-butyl-, isobutyl and t-butyl-; "propyl" includes n-propyl-, isopropyl-, and c-propyl-.

Alkylene-, alkenylene-, and alkynylene- are other subsets of alkyl-, including the same residues as alkyl-, but having two points of attachment within a chemical structure. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). Likewise, examples of alkenylene include ethenylene (—CH=CH—), propenylene (—CH=CH—$CH_2$—), and cyclohexylpropenylene (—CH=CHCH($C_6H_{13}$)—). Examples of alkynylene include ethynylene (—C≡C—) and propynylene (—CH=CH—$CH_2$—).

Cycloalkenyl is a subset of alkyl and includes unsaturated cyclic hydrocarbon groups of from 3 to 13 carbon atoms. Examples of cycloalkenyl groups include c-hexenyl-, c-pentenyl and the like.

Alkoxy or alkoxyl refers to an alkyl group, preferably including from 1 to 8 carbon atoms, of a straight, branched, or cyclic configuration, or a combination thereof, attached to the parent structure through an oxygen (i.e., the group alkyl-O—). Examples include methoxy-, ethoxy-, propoxy-, isopropoxy-, cyclopropyloxy-, cyclohexyloxy- and the like. Lower-alkoxy refers to alkoxy groups containing one to four carbons.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by oxygen, nitrogen (e.g., carboxamido), or sulfur as long as the point of attachment to the parent remains at the carbonyl. Examples include acetyl-, benzoyl-, propionyl-, isobutyryl-, oxalyl-, t-butoxycarbonyl-, benzyloxycarbonyl, morpholinylcarbonyl, and the like. Lower-acyl refers to acyl groups containing one to four carbons.

Amino refers to the group —$NH_2$. The term "substituted amino" refers to the group —NHR or —NRR where each R is independently selected from the group: optionally substituted alkyl-, optionally substituted alkoxy, optionally substituted aminocarbonyl-, optionally substituted aryl-, optionally substituted heteroaryl-, optionally substituted heterocyclyl-, acyl-, alkoxycarbonyl-, sulfanyl-, sulfinyl and sulfonyl-, e.g., diethylamino, methylsulfonylamino, furanyl-oxy-sulfonamino.

Aminocarbonyl- refers to the group —$NR^cCOR^b$, —$NR^cCO_2R^a$, or —$NR^cCONR^bR^c$, where
  $R^a$ is an optionally substituted $C_1$-$C_6$ alkyl-, aryl-, heteroaryl-, aryl-$C_1$-$C_4$ alkyl-, or heteroaryl-$C_1$-$C_4$ alkyl- group;
  $R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and
  $R^c$ is hydrogen or $C_1$-$C_4$ alkyl-; and where each optionally substituted $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$O_2$NH (phenyl), —$NHSO_2$($C_1$-$C_4$ alkyl), —$NHSO_2$(phenyl), and —$NHSO_2$($C_1$-$C_4$ haloalkyl).

Antimitotic refers to a drug for inhibiting or preventing mitosis, for example, by causing metaphase arrest. Some antitumour drugs block proliferation and are considered antimitotics.

Aryl and heteroaryl mean a 5- or 6-membered aromatic or heteroaromatic ring containing 0 or 1-4 heteroatoms, respectively, selected from O, N, or S; a bicyclic 9- or 10-membered aromatic or heteroaromatic ring system containing 0 or 1-4 (or more) heteroatoms, respectively, selected from O, N, or S; or a tricyclic 12- to 14-membered aromatic or heteroaromatic ring system containing 0 or 1-4 (or more) heteroatoms, respectively, selected from O, N, or S. The aromatic 6- to 14-membered carbocyclic rings include, e.g., phenyl-, naphthyl-, indanyl-, tetralinyl-, and fluorenyl and the 5- to 10-membered aromatic heterocyclic rings include, e.g., imidazolyl-, pyridinyl-, indolyl-, thienyl-, benzopyranonyl-, thiazolyl-, furanyl-, benzimidazolyl-, quinolinyl-, isoquinolinyl-, quinoxalinyl-, pyrimidinyl-, pyrazinyl-, tetrazolyl and pyrazolyl-.

Aralkyl- refers to a residue in which an aryl moiety is attached to the parent structure via an alkyl residue. Examples include benzyl-, phenethyl-, phenylvinyl-, phenylallyl and the like. Heteroaralkyl- refers to a residue in which a heteroaryl moiety is attached to the parent structure via an alkyl residue. Examples include furanylmethyl-, pyridinylmethyl-, pyrimidinylethyl and the like.

Aralkoxy- refers to the group —O-aralkyl. Similarly, heteroaralkoxy-refers to the group —O-heteroaralkyl-; aryloxy- refers to the group —O-aryl-; acyloxy-refers to the group —O-acyl-; heteroaryloxy- refers to the group —O-heteroaryl-; and heterocyclyloxy- refers to the group —O-heterocyclyl (i.e., aralkyl-, heteroaralkyl-, aryl-, acyl-, heterocyclyl-, or heteroaryl is attached to the parent structure through an oxygen).

Carboxyalkyl- refers to the group -alkyl-COOH.

Carboxamido refers to the group —CONR$^b$R$^c$, where $R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and $R^c$ is hydrogen or $C_1$-$C_4$ alkyl-; and where each optionally substituted $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl, —$C_1$-$C_4$ alkyl-OH, —O$C_1$-$C_4$ haloalkyl, halogen, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl, —CON($C_1$-$C_4$ alkyl) ($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O) (phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$ ($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). Carboxamido is meant to include carbamoyl-; lower-alkyl carbamoyl-; benzylcarbamoyl-; phenylcarbamoyl-; methoxymethyl-carbamoyl-; and the like.

Halogen or halo refers to fluorine, chlorine, bromine or iodine. Fluorine, chlorine and bromine are preferred. Dihaloaryl-, dihaloalkyl-, trihaloaryl etc. refer to aryl and alkyl substituted with the designated plurality of halogens (here, 2, 2 and 3, respectively), but not necessarily a plurality of the same halogen; thus 4-chloro-3-fluorophenyl is within the scope of dihaloaryl-.

Heterocyclyl means a cycloalkyl or aryl residue in which one to four of the carbons is replaced by a heteroatom such as oxygen, nitrogen or sulfur. Examples of heterocycles that fall within the scope of the invention include azetidinyl-, imidazolinyl-, pyrrolidinyl-, pyrazolyl-, pyrrolyl-, indolyl-, quinolinyl-, isoquinolinyl-, tetrahydroisoquinolinyl-, benzofuranyl-, benzodioxanyl-, benzodioxyl (commonly referred to as methylenedioxyphenyl-, when occurring as a substituent), tetrazolyl-, morpholinyl-, thiazolyl-, pyridinyl-, pyridazinyl-, piperidinyl-, pyrimidinyl-, thienyl-, furanyl-, oxazolyl-, oxazolinyl-, isoxazolyl-, dioxanyl-, tetrahydrofuranyl and the like. "N-heterocyclyl" refers to a nitrogen-containing heterocycle. The term heterocyclyl encompasses heteroaryl-, which is a subset of heterocyclyl-. Examples of N-heterocyclyl residues include azetidinyl-, 4-morpholinyl-, 4-thiomorpholinyl-, 1-piperidinyl-, 1-pyrrolidinyl-, 3-thiazolidinyl-, piperazinyl and 4-(3,4-dihydrobenzoxazinyl). Examples of substituted heterocyclyl include 4-methyl-1-piperazinyl and 4-benzyl-1-piperidinyl-.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

Optional or optionally means that the subsequently described event or circumstance may or may not occur, and that the description includes instances where said event or circumstances occurs and instances in which it does not. For example, "optionally substituted alkyl" includes "alkyl" and "substituted alkyl" as defined herein. It will be understood by those skilled in the art with respect to any group containing one or more substituents that such groups are not intended to introduce any substitution or substitution patterns that are sterically impractical and/or synthetically non-feasible and/ or inherently unstable.

Substituted alkoxy refers to alkoxy wherein the alkyl constituent is substituted (i.e., —O-(substituted alkyl)). One suitable substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of about 2-20, preferably about 2-10, and more preferably about 2-5. Another suitable substituted alkoxy group is hydroxyalkoxy or —OCH$_2$(CH$_2$)$_y$OH, where y is an integer of about 1-10, preferably about 1-4.

Substituted- alkyl-, aryl-, and heteroaryl- refer respectively to alkyl-, aryl-, and heteroaryl wherein one or more (up to about 5, preferably up to about 3) hydrogen atoms are replaced by a substituent independently selected from the group: —R$^a$, —OR$^b$, —O($C_1$-$C_2$ alkyl)O— (as an aryl substituent), —SR$^b$, guanidine, guanidine wherein one or more of the guanidine hydrogens are replaced with a lower-alkyl group, —NR$^b$R$^c$, halogen, cyano, nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, —SO$_2$R$^a$, —SO$_2$NR$^b$R$^c$, and —NR$^c$SO$_2$R$^a$, where $R^a$ is an optionally substituted $C_1$-$C_6$ alkyl-, aryl-, heteroaryl-, aryl-$C_1$-$C_4$ alkyl-, or heteroaryl-$C_1$-$C_4$ alkyl- group, $R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group;

$R^c$ is hydrogen or $C_1$-$C_4$ alkyl-;

where each optionally substituted $R^a$ group and $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl-, —$C_1$-$C_4$ alkyl-OH, —O$C_1$-$C_4$ haloalkyl-, halogen, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl-, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl-, —C(O)$C_1$-$C_4$ phenyl-, —C(O)$C_1$-$C_4$ haloalkyl-, —OC(O)$C_1$-$C_4$ alkyl-, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —S($O_2$)—H, —S($O_2$)-(optionally substituted alkyl), —S($O_2$)-optionally substituted aryl), —S($O_2$)-(optionally substituted heteroaryl), —S($O_2$)-(optionally substituted heterocyclyl), —S($O_2$)-(optionally substituted alkoxy), —S($O_2$)-optionally substituted aryloxy), —S($O_2$)-(optionally substituted heteroaryloxy), —S($O_2$)-(optionally substituted heterocyclyloxy); and —S($O_2$)-(optionally substituted amino).

Pharmaceutically acceptable salts refers to those salts that retain the biological effectiveness of the free compound and that are not biologically undesirable or unsuitable for pharmaceutical use, formed with a suitable acid or base, and includes pharmaceutically acceptable acid addition salts and base addition salts. Pharmaceutically acceptable acid addition salts include those derived from inorganic acids such as hydrochloric acid, hydrobromic acid, sulfuric acid, nitric acid, phosphoric acid and the like, and those derived from organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particular embodiments are the ammonium, potassium, sodium, calcium, and magnesium salts. Base addition salts also include those derived from pharmaceutically acceptable organic nontoxic bases, including salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form is where at least one of the hydroxyl groups present in a compound is protected with a hydroxy protecting group. Likewise, amines and other reactive groups may similarly be protected.

Solvate refers to the compound formed by the interaction of a solvent and a compound of Formula I or salt thereof. Suitable solvates of the compounds of the Formula I or a salt thereof are pharmaceutically acceptable solvates including hydrates.

Many of the compounds described herein contain one or more asymmetric centers (e.g. the carbon to which $R_2$ and $R_{2'}$ are attached where $R_2$ differs from $R_{2'}$) and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms and rotational isomers are also intended to be included.

When desired, the R- and S-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Compounds of the Present Invention

The present invention is directed to a class of novel compounds, that can be described as pyrimidinone derivatives, that are inhibitors of one or more mitotic kinesins. By inhibiting mitotic kinesins, but not other kinesins (e.g., transport kinesins), specific inhibition of cellular proliferation is accomplished. While not intending to be bound by any theory, the present invention capitalizes on the finding that perturbation of mitotic kinesin function causes malformation or dysfunction of mitotic spindles, frequently resulting in cell cycle arrest and cell death. According to one embodiment of the invention, the compounds described herein inhibit the mitotic kinesin, KSP, particularly human KSP. In another embodiment, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see, U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a mitotic kinesin comprise contacting an inhibitor of the invention with a kinesin, particularly a human kinesin, more particularly, human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

The present invention provides inhibitors of mitotic kinesins, in particular KSP and especially human KSP, for the treatment of disorders associated with cell proliferation. The compounds, compositions and methods described herein can differ in their selectivity and are used to treat diseases of cellular proliferation, including, but not limited to cancer, hyperplasias, restenosis, cardiac hypertrophy, immune disorders, fungal disorders and inflammation.

Accordingly, the present invention relates to methods employing compounds represented by Formula I:

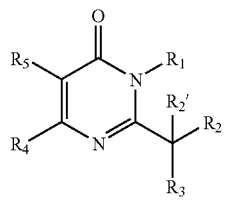

Formula I wherein:
- $R_1$ is chosen from hydrogen, optionally substituted alkyl-, optionally substituted aryl-, optionally substituted aralkyl-, optionally substituted heteroaryl-, and optionally substituted heteroaralkyl-;
- $R_2$ and $R_2'$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_2'$ taken together form an optionally substituted 3- to 7-membered ring;
- $R_3$ is selected from the group consisting of optionally substituted imidazolyl-, optionally substituted imidazolinyl-, —$NHR_6$; —$N(R_6)(COR_7)$; —$N(R_6)(SO_2R_{7a})$; and —$N(R_6)(CH_2R_{7b})$;
- $R_6$ is chosen from hydrogen, optionally substituted alkyl-, optionally substituted aryl-, optionally substituted aralkyl-, optionally substituted heteroaralkyl-, and optionally substituted heterocyclyl-;
- $R_7$ is chosen from hydrogen, optionally substituted alkyl-, optionally substituted aryl-, optionally substituted aralkyl-, optionally substituted heteroaryl-, optionally substituted heteroaralkyl-, $R_8O$— and $R_{14}$—NH—;
- $R_{7a}$ is chosen from optionally substituted alkyl-, optionally substituted aryl-, optionally substituted aralkyl-, optionally substituted heteroaryl-, optionally substituted heteroaralkyl-, and $R_{14}$—NH—;
- $R_{7b}$ is chosen from hydrogen, optionally substituted alkyl-, optionally substituted aryl-, optionally substituted aralkyl-, optionally substituted heteroaryl-, and optionally substituted heteroaralkyl-;
- $R_8$ is chosen from optionally substituted alkyl-, optionally substituted aryl-, optionally substituted aralkyl-, optionally substituted heteroaryl-, and optionally substituted heteroaralkyl-;
- $R_{14}$ is chosen from hydrogen, optionally substituted alkyl-, optionally substituted aryl-, optionally substituted aralkyl-, optionally substituted heteroaryl-, and optionally substituted heteroaralkyl-; and
- $R_4$ and $R_5$ are independently chosen from hydrogen, optionally substituted alkyl-, optionally substituted alkoxy, halogen, hydroxyl-, nitro, cyano, dialkylamino, alkylsulfonyl-, alkylsulfonamido, alkylsulfanyl-, carboxyalkyl-, carboxamido, aminocarbonyl-, optionally substituted aryl-, optionally substituted aralkyl-, optionally substituted heteroaralkyl and optionally substituted heteroaryl-; or $R_4$ and $R_5$ taken together with the carbons to which they are attached form an optionally substituted 5-, 6- or 7-membered aliphatic carbocyclic ring;

including single stereoisomers and mixtures of stereoisomers;

a pharmaceutically acceptable salt of a compound of Formula I;

a pharmaceutically acceptable solvate of a compound of Formula I;

or a pharmaceutically acceptable solvate of a pharmaceutically acceptable salt of a compound of Formula I. In a particular embodiment, the stereogenic center to which $R_2$ and $R_2'$ are attached is of the R configuration.

Nomenclature

The compounds of Formula I can be named and numbered in the manner (e.g., using AutoNom version 2.1 in ISIS-DRAW or ChemDraw) described below. For example, the compound:

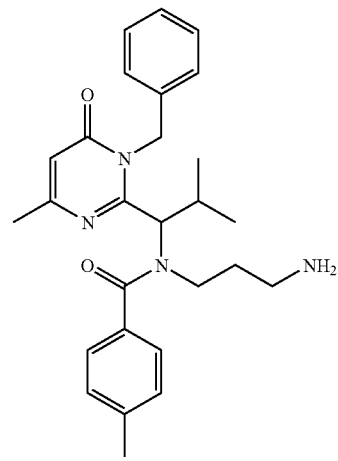

i.e., the compound according to Formula I where $R_1$ is benzyl-, $R_2$ is propyl (or i-propyl), $R_2'$ is hydrogen; $R_3$ is —$N(R_6)(COR_7)$; $R_4$ is methyl-; $R_5$ is hydrogen; $R_6$ is aminopropyl-; and $R_7$ is p-tolyl can be named N-(3-amino-propyl)-N-[1-(1-benzyl-4-methyl-6-oxo-1,6-dihydro-pyrimidin-2-yl)-2-methyl-propyl]-4-methyl-benzamide.

Likewise, the compound

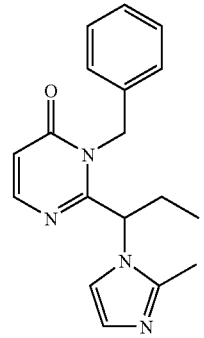

i.e., the compound according to Formula I where $R_1$ is benzyl-, $R_2$ is ethyl-, $R_{2'}$ is hydrogen; $R_3$ is substituted imidazolyl-; and $R_4$ and $R_5$ are hydrogen can be named 3-benzyl-2-[1-(2-methyl-imidazol-1-yl)-propyl]-3H-pyrimidin-4-one.

The compound

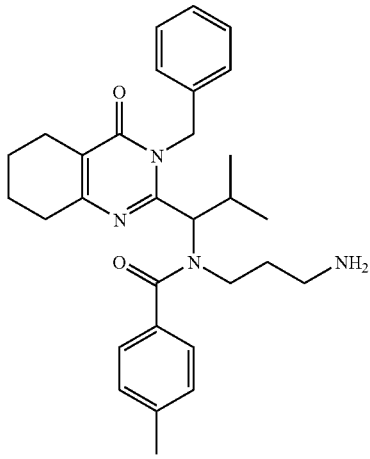

i.e., the compound according to Formula I where $R_1$ is benzyl-, $R_2$ is i-propyl-, $R_{2'}$ is hydrogen; $R_3$ is —$N(R_6)(COR_7)$; $R_6$ is aminopropyl-; $R_7$ is p-tolyl-; and $R_4$ and $R_5$, together with the carbons to which they are bound, form a 6-membered carbocyclic ring can be named N-(3-amino-propyl)-N-[1-(3-benzyl-4-oxo-3,4,5,6,7,8-hexahydro-quinazolin-2-yl)-2-methyl-propyl]-4-methyl-benzamide.

Synthetic Reaction Parameters

The compounds of Formula I can be prepared by following the procedures described with reference to the Reaction Schemes below.

Unless specified otherwise, the terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

In general, esters of carboxylic acids may be prepared by conventional esterification procedures, for example alkyl esters may be prepared by treating the required carboxylic acid with the appropriate alkanol, generally under acidic conditions. Likewise, amides may be prepared using conventional amidation procedures, for example amides may be prepared by treating an activated carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4171-4173, (1977). Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates of the compounds mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

The compounds of Formula I can be prepared by following the procedures with reference to the Reaction Schemes below.

Brief Description Of Reaction Schemes

Reaction Scheme 1 illustrates synthesis of compounds of Formula I wherein $R_3$ is —$N(R_6)(COR_7)$.

Reaction Scheme 2 illustrates a synthesis of compounds of Formula 205 which are useful as intermediates in the synthesis of compounds of Formula I.

Reaction Scheme 3 illustrates a synthesis of compounds of Formula I wherein $R_3$ is —$N(R_6)(SO_2R_{7a})$.

Reaction Scheme 4 illustrates a synthesis of compounds of Formula I wherein $R_3$ is —$N(R_6)(CH_2R_{7b})$.

Reaction Scheme 5 illustrates a synthesis of compounds of Formula I wherein $R_3$ is optionally substituted imidazolyl-.

Reaction Scheme 6 illustrates an alternative synthesis of compounds of Formula I wherein $R_3$ is optionally substituted imidazolyl-.

Reaction Scheme 7 illustrates a synthesis of compounds of Formula I wherein $R_3$ is optionally substituted imidazolinyl-.

Reaction Scheme 8 illustrates an alternative synthesis of compounds of Formula I wherein $R_3$ is optionally substituted imidazolinyl-.

Reaction Scheme 9 illustrates a synthesis of compounds of Formula 907 which are useful as intermediates in the synthesis of compounds of Formula I.

Reaction Scheme 10 illustrates an alternative synthesis of compounds of Formula 907 which are useful as intermediates in the synthesis of compounds of Formula I.

Reaction Scheme 11 illustrates a synthesis of compounds of Formula 1103 which are useful as intermediates in the synthesis of compounds of Formula I.

Reaction Scheme 12 illustrates a synthesis of compounds of Formula 1203 which are useful as intermediates in the synthesis of compounds of Formula I.

Reaction Scheme 13 illustrates a synthesis of compounds of Formula I wherein $R_4$ is —(CO)$NH_2$ or —CN.

Reaction Scheme 14 illustrates a synthesis of compounds of Formula 1405 which are useful as intermediates in the synthesis of compounds of Formula I.

Reaction Scheme 15 illustrates a synthesis of compounds of Formula 1505 which are useful as intermediates in the synthesis of compounds of Formula I.

Reaction Scheme 16 illustrates a synthesis of compounds of Formula 1605 which are useful as intermediates in the synthesis of compounds of Formula I.

Reaction Scheme 17 illustrates a synthesis of compounds of Formula I wherein $R_5$ is bromo or phenyl.

Reaction Scheme 18 illustrates a synthesis of compounds of Formula I wherein $R_5$ is —CN or —($CH_2$)NH(CO)$CH_3$.

Reaction Scheme 19 illustrates synthesis of compounds of Formula I wherein $R_3$ is —N($R_6$)(CO$R_7$) and $R_7$ is —O$R_9$.

Reaction Scheme 20 illustrates a synthesis of compounds of Formula I wherein $R_3$ is —N($R_6$)(CO$R_7$) and $R_7$ is —NH$R_{14}$.

Reaction Scheme 21 illustrates a synthesis of compounds of Formula 2103 which are useful as intermediates in the synthesis of compounds of Formula I.

Reaction Scheme 22 illustrates a synthesis of compounds of Formula 2205 which are useful as intermediates in the synthesis of compounds of Formula I.

Reaction Scheme 23 illustrates a synthesis of compounds of Formula 2305 which are useful as intermediates in the synthesis of compounds of Formula I.

Reaction Scheme 24 illustrates a synthesis of compounds of Formula I wherein $R_3$ is —N($R_6$)(CO$R_7$).

Reaction Scheme 25 illustrates a synthesis of compounds of Formula I wherein $R_3$ is —N($R_6$)(CO$R_7$).

Reaction Scheme 26 illustrates an alternative synthesis of compounds of Formula I wherein $R_3$ is optionally substituted imidazolinyl Reaction Scheme 27 illustrates an alternative synthesis of compound of Formula I wherein $R_3$ is optionally substituted imidazolyl-.

Reaction Scheme 28 illustrates a synthesis of compounds of Formula I wherein $R_5$ is an optionally substituted amino group.

Starting Materials

The optionally substituted β-keto amides of Formula 101 and the other reactants are commercially available, e.g., from Aldrich Chemical Company, Milwaukee, Wis. or may be readily prepared by those skilled in the art using commonly employed synthetic methodology.

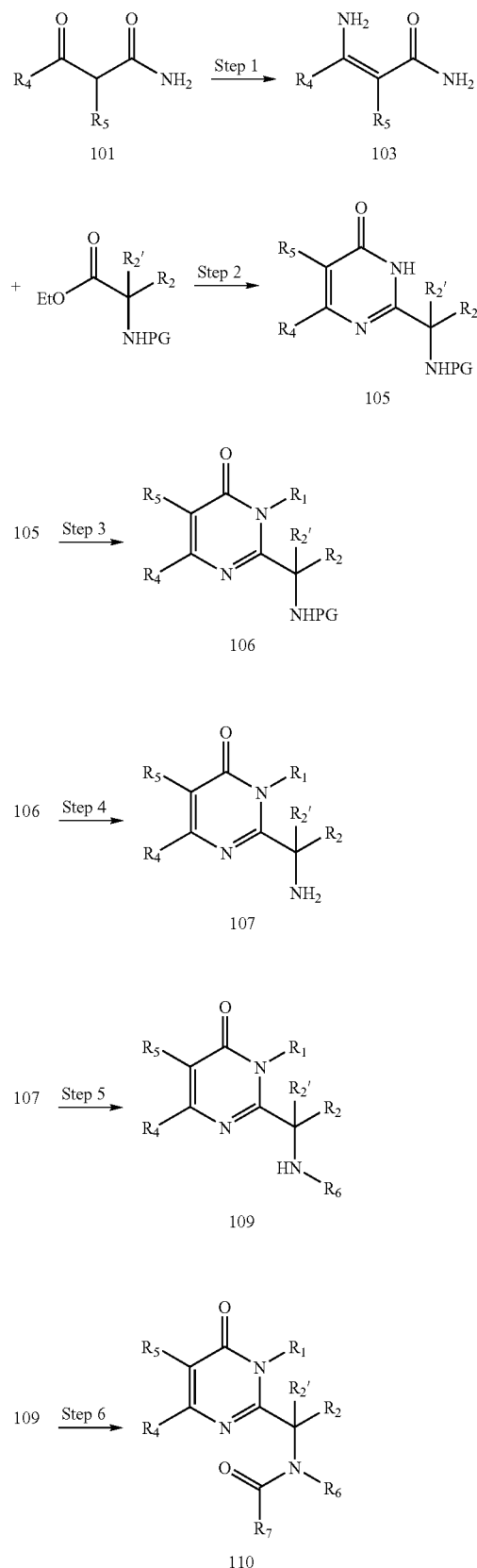

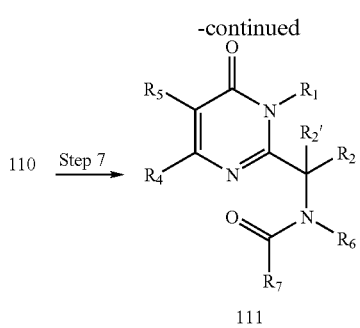

Preparation of Formula 103

Referring to Reaction Scheme 1, Step 1, a mixture of an optionally substituted acetoacetamide (the compound of Formula 101) or an acetoacetate ester in an inert organic solvent (such as xylenes) is added to a flask equipped with a dry-ice reflux condenser. The resulting mixture is heated to reflux and purged continuously with gaseous ammonia for about 3 hours, and then cooled to room temperature. The reaction mixture is filtered and the filtrate is concentrated under reduced pressure. The optionally substituted β-aminocrotonamide (the compound of Formula 103) is isolated and purified.

Preparation of Formula 105

Referring to Reaction Scheme 1, Step 2, freshly generated sodium ethoxide is added to a mixture of a compound of Formula 103 and a slight excess (preferably about 1.1 equivalents) of a suitably protected alpha amino acid ester (a compound of Formula 104, preferably wherein protecting group, PG, is Boc) in ethanol. The resulting solution is heated at reflux for several hours. The product, a pyrimidinone of Formula 105, is isolated and purified.

Preparation of Formula 106

Referring to Reaction Scheme 1, Step 3, to a solution of a pyrimidinone of Formula 105 in a polar, aprotic solvent such as dioxane is added an excess (preferably about 1.2 equivalents) of lithium hydride, while maintaining room temperature. The resulting suspension is stirred for about 15 minutes, followed by addition of a slight excess (preferably about 1.1 equivalents) of a compound having the structure $R_1$—X wherein X is a leaving group, preferably a tosylate and $R_1$ is as defined above. The reaction mixture is heated at reflux for about 20-24 hours. The product, a pyrimidinone of Formula 106, is isolated and purified.

Preparation of Formula 107

Referring to Reaction Scheme 1, Step 4, the amino protecting group of a compound of Formula 106 is removed. For example, to a solution of a pyrimidinone of Formula 106 wherein the amino protecting group, PG, is Boc in a polar, aprotic solvent such as dichloromethane is added trifluoroacetic acid, while maintaining the temperature at about 0° C. The resulting solution is then stirred at room temperature for one hour and concentrated in vacuo. The product, a compound of Formula 107, is isolated and used in the next step without further purification. One of skill in the art will readily appreciate that the removal of other protecting groups can be accomplished using conditions known in the art. See, e.g., Greene, et al. supra.

Preparation of Formula 109

Referring to Reaction Scheme 1, Step 5, to a solution of a pyrimidinone of Formula 107 is added successively a slight excess (preferably about 1.2 equivalents) of an aldehyde comprising $R_{6'}$ (i.e., a compound having the formula $R_{6'}$CHO where $R_{6'}$CH$_2$— is equivalent to $R_6$ and $R_6$ is as described above or is a protected precursor to such a substituent, e.g., (3-oxo-propyl)-carbamic acid tert-butyl ester) and a reducing agent such as sodium triacetoxyborohydride. The resulting mixture is stirred for several hours. The product, a pyrimidinone of Formula 109, is isolated and purified.

Preparation of Formula 110

Referring to Reaction Scheme 1, Step 6, to a solution of a pyrimidinone of Formula 109 and an amine base such as diisopropylethylamine in a polar, aprotic solvent such as dichloromethane is added an $R_7$ acyl chloride (such as Cl—C(O)—$R_7$ where $R_7$ is as described above). The resulting solution is stirred under nitrogen at room temperature for several hours. The product, a pyrimidinone of Formula 110, is isolated and purified.

Preparation of Formula 111

Optionally, any protecting groups on a compound of Formula 110 are then removed. For example, if $R_6$ comprises a protected amine wherein the protecting group is a Boc group, then referring to Reaction Scheme 1, Step 7, to a solution of a pyrimidinone of Formula 110 in a polar, aprotic solvent such as dichloromethane is added trifluoroacetic acid, while maintaining the reaction at about room temperature. The reaction is monitored, e.g., by TLC. Upon completion, the product, a pyrimidinone of Formula III, is isolated and purified.

Preparation of Optically Active Compounds of Formula 107

In certain compounds of the invention, a particular stereo configuration (such as the (R) isomer) may be preferred at the stereogenic center to which $R_2$ is attached. The optically active compound can be prepared by methods known in the art. For example, an amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer, is isolated and purified.

For the sake of brevity in the remaining description of the synthesis of compounds of Formula I, it should be understood that either single isomer or a mixture of isomers may be employed to give the corresponding product.

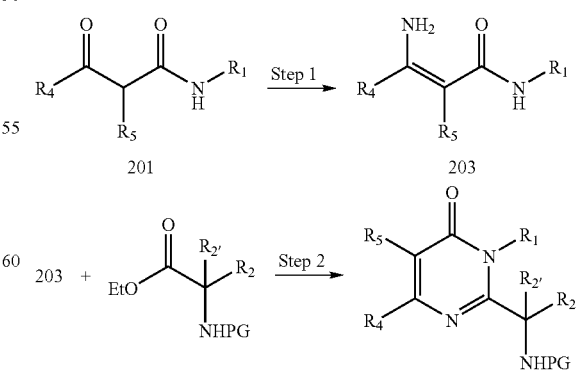

Preparation of Formula 203

Referring to Reaction Scheme 2, Step 1, a mixture of an optionally substituted beta-ketoamide of Formula 201 in an inert organic solvent (such as xylenes) is added to a flask equipped with a dry-ice reflux condenser. The resulting mixture is heated to reflux and purged continuously with gaseous ammonia for about 5 hours, and then cooled to room temperature. The reaction mixture is filtered and the filtrate is concentrated under reduced pressure. The product, an optionally substituted compound of Formula 203, is isolated and used in the next step without further purification.

Preparation of Formula 205

Referring to Reaction Scheme 2, Step 2, freshly generated sodium ethoxide is added to a mixture of a compound of Formula 203 and a slight excess (preferably about 1.1 equivalents) of a suitably protected alpha amino acid ester (a compound of Formula 204, and more preferably, a compound of Formula 204 wherein PG is Boc) in ethanol. The resulting solution is heated at reflux for several hours. The product, a pyrimidinone of Formula 205, is isolated and purified.

Reaction Scheme 3

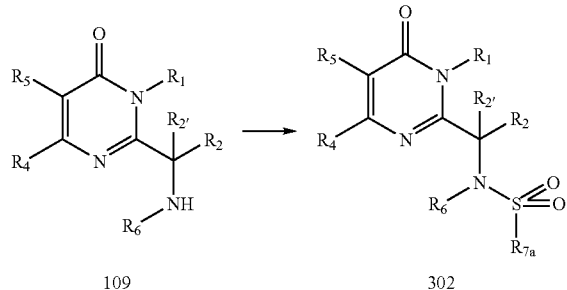

Referring to Reaction Scheme 3, to a solution of a pyrimidinone of Formula 109 and an amine base such as diisopropylethylamine in a polar, aprotic solvent such as dichloromethane is added a compound having the formula Cl—S(O)$_2$—R$_{7a}$ or O—(S(O)$_2$—R$_{7a}$)$_2$ where R$_{7a}$ is as described above. The resulting solution is stirred under nitrogen at room temperature for several hours. The product, a pyrimidinone of Formula 302, is isolated and purified.

Reaction Scheme 4

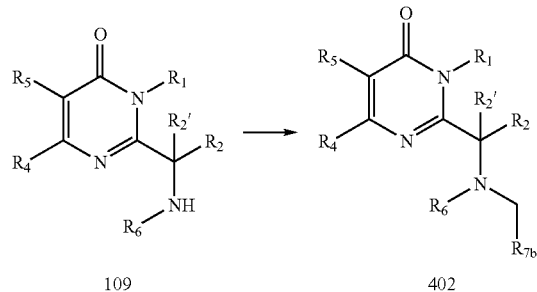

Referring to Reaction Scheme 4, to a solution of a pyrimidinone of Formula 109 and an amine base such as diisopropylethylamine in a polar, aprotic solvent such as dichloromethane is added a compound having the formula X—CH$_2$—R$_7$ where R$_7$ is as described above and X is a leaving group (preferably a halide). The resulting solution is stirred under nitrogen at room temperature or with heat for several hours. The product, a pyrimidinone of Formula 402, is isolated and purified.

Reaction Scheme 5

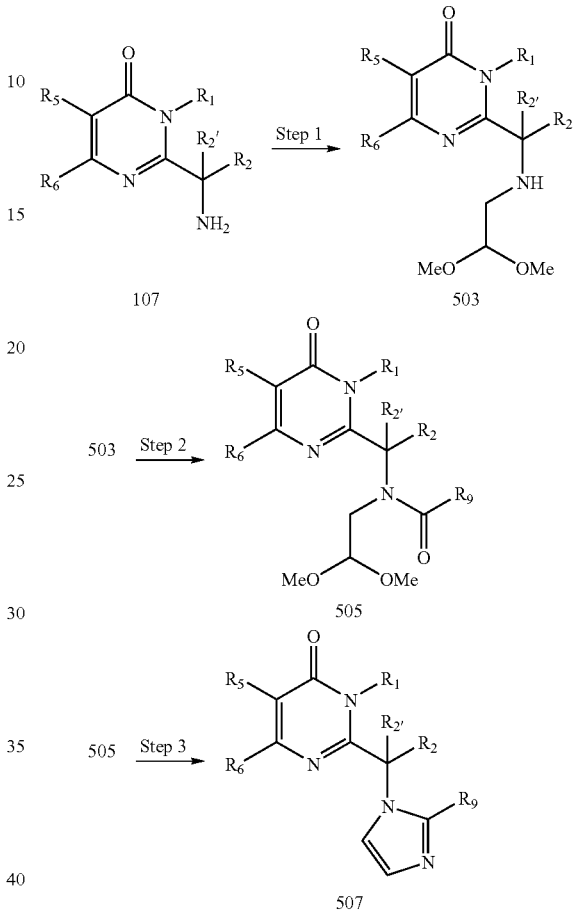

Preparation of Formula 503

Referring to Reaction Scheme 5, Step 1, to an optionally substituted compound of Formula 107 dissolved in a polar, aprotic solvent (such as DMF) in the presence of a base (such as potassium carbonate) is added one equivalent of an optionally substituted suitably protected aldehyde wherein such aldehyde further comprises a leaving group, preferably, a halide. The solution is heated at reflux, monitoring completion of the reaction (e.g., by TLC). The reaction mixture is cooled and the corresponding, optionally substituted pyrimidinone of Formula 503 is isolated and purified.

Preparation of Formula 505

Referring to Reaction Scheme 5, Step 2, to an optionally substituted compound of Formula 503 in an inert solvent (such as dichloromethane) in the presence of about 1.5 molar equivalents of an amine base (such as triethylamine) is added about 1.5 molar equivalents of an R$_9$ acid chloride, such as, Cl—C(O)—R$_9$, where R$_9$ is as described herein. The reaction takes place, with stirring, at room temperature over a period of 4 to 24 hours. Completion is monitored, e.g., by TLC. The corresponding compound of Formula 505 is isolated and purified.

Preparation of Formula 507

Referring to Reaction Scheme 5, Step 3, a solution of a compound of Formula 505 and an excess of ammonium acetate in acetic acid is heated at reflux for 1-4 hours. Completion is monitored, e.g., by TLC. The corresponding compound of Formula 507 is isolated and purified.

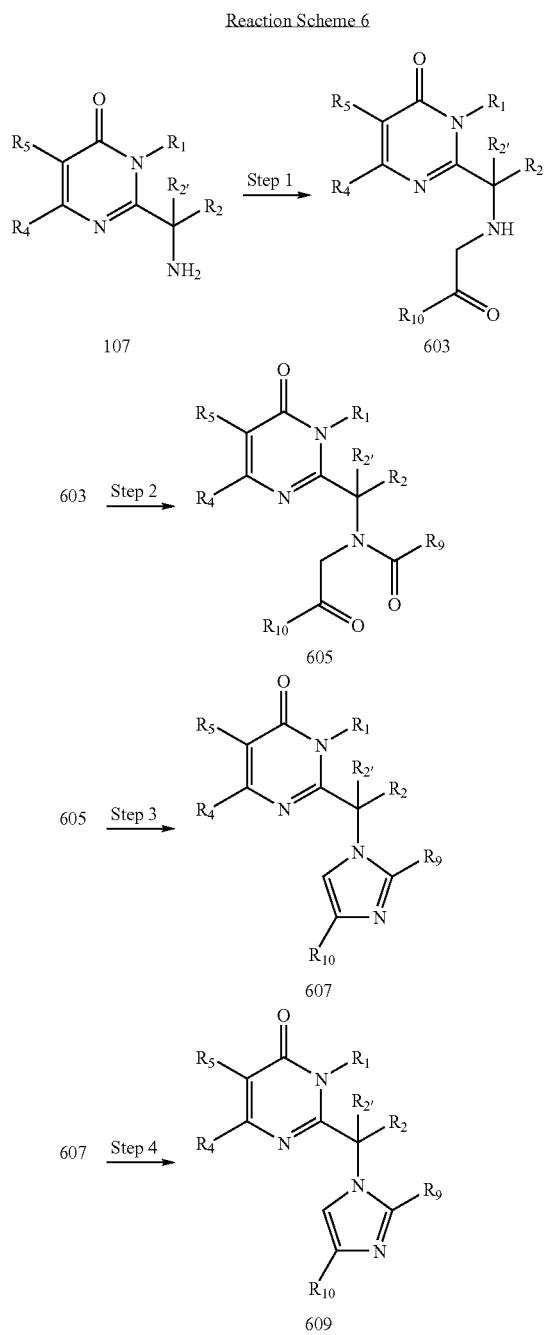

Preparation of Formula 603

Referring to Reaction Scheme 6, Step 1, a suspension of a compound of Formula 107, an alpha-haloketone reagent of the Formula $R_{10}(CO)CH_2X$ wherein X is a halide, and about an equivalent of a base, such as potassium carbonate in a polar, aprotic solvent such as DMF is stirred at room temperature. The reaction is diluted with water and the resulting solid, a compound of Formula 603, is used in the subsequent step without further purification.

Preparation of Formula 605

Referring to Reaction Scheme 6, Step 2, a solution of the compound of Formula 603, about an equivalent of an amine base, such as triethylamine and about an equivalent of an acid chloride (such as a compound of Formula $R_9$—COCl) in an organic solvent such as methylene chloride is stirred at room temperature for several hours. Completion is monitored, e.g., by TLC. The corresponding compound of Formula 605 is isolated and purified.

Preparation of Formula 607

Referring to Reaction Scheme 6, Step 3, a solution of a compound of Formula 605 and an excess of ammonium acetate in acetic acid is heated at reflux using a Dean-Stark trap and condenser. Completion is monitored, e.g., by TLC. The corresponding compound of Formula 607 is isolated and purified.

Preparation of Formula 609

Referring to Reaction Scheme 6, Step 4, if 607 is protected as a phthalimide, a solution of a compound of Formula 607 and an excess of anhydrous hydrazine in a polar, protic solvent such as ethanol is heated at reflux. The reaction is cooled to about 5° C. and any precipitate is filtered off. The filtrate is concentrated in vacuo and purified to yield a compound of Formula 609.

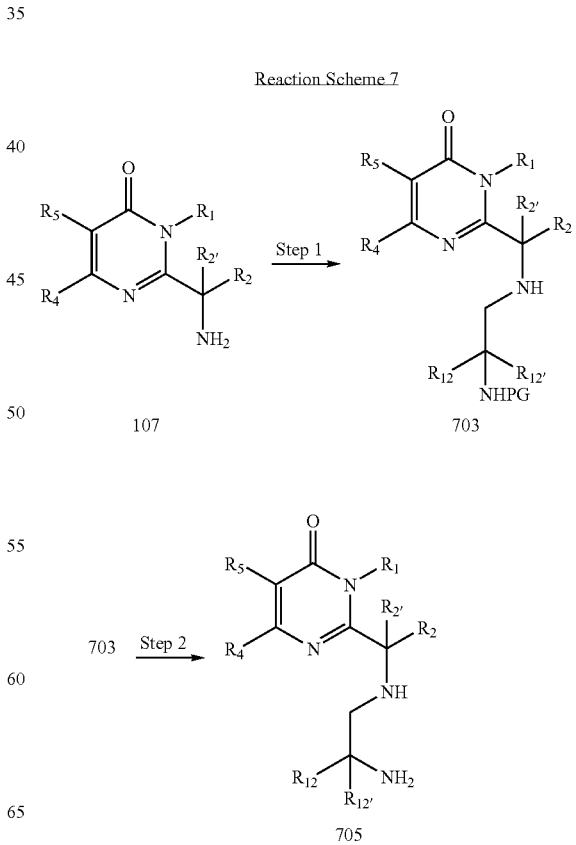

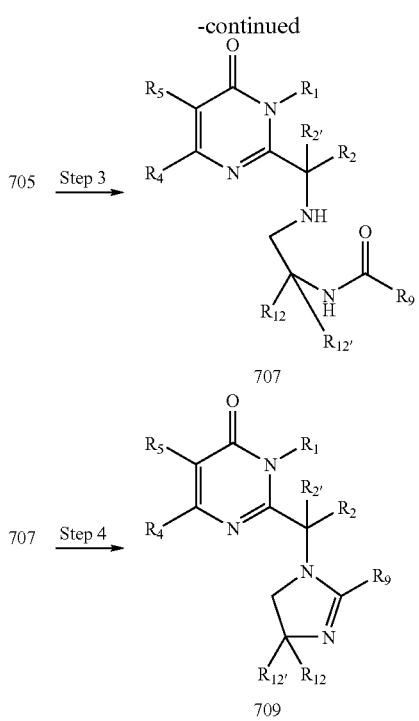

Preparation of Formula 709

Referring to Reaction Scheme 7, Step 4, a solution of a compound of Formula 707 in an excess of phosphorus oxychloride is heated at reflux. After 8 hours, the reaction mixture is allowed to cool to ambient temperature and concentrated under reduced pressure. The corresponding compound of Formula 709 is isolated and purified.

Reaction Scheme 8

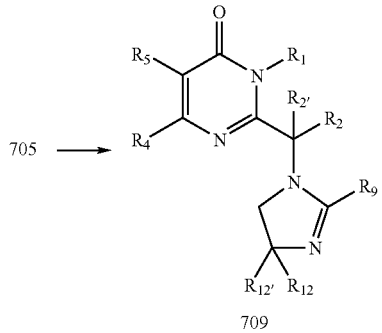

Preparation of Formula 709

As an alternative to Steps 3 and 4 of Reaction Scheme 7, acylation of primary amines of Formula 705, followed by acetic acid mediated cyclization, can proceed without isolation of the intermediate amides to provide the target compound of Formula 709. This route is shown in Reaction Scheme 8.

More specifically, to a solution of a compound of Formula 705 in a polar, aprotic solvent such as dichloromethane is added an excess, preferably about two equivalents of an amine base, such as triethylamine, followed by about an equivalent of an acid chloride. The resultant solution is stirred at ambient temperature for 2 hours, then evaporated under reduced pressure. The resultant solid is treated with glacial acetic acid, then the resultant suspension is heated at reflux for about 48 hours. The reaction is cooled to ambient temperature then evaporated under reduced pressure. The corresponding compound of Formula 709 is isolated and purified.

Preparation of Formula 703

Referring to Reaction Scheme 7, Step 1, reductive amination of amines of Formula 107 (prepared as described in WO 0130768) with an optionally substituted, aldehyde-containing carbamic acid ester (Seki et. al. *Chem. Pharm. Bull.* 1996, 44, 2061) gives urethane intermediates. Removal of the Boc protecting group furnishes an amine of Formula 705.

More specifically, to a solution of a compound of Formula 107 and an equivalent of a suitably protected aldehyde (Seki et. al. *Chem. Pharm. Bull.* 1996, 44, 2061) in dichloromethane is added a slight excess of a reducing agent, such as sodium triacetoxyborohydride. The resultant cloudy mixture is maintained at ambient temperature. Completion is monitored, e.g., by TLC. The corresponding compound of Formula 703 is isolated and used in the subsequent step without purification.

Preparation of Formula 705

Referring to Reaction Scheme 4, Step 2, to a solution of a compound of Formula 703 in a polar, aprotic solvent such as dichloromethane is added a strong acid such as trifluoroacetic acid. The resultant solution is maintained at ambient temperature overnight and concentrated under reduced pressure. The residue is isolated to give a compound of Formula 705 which is used in the subsequent step without purification.

Preparation of Formula 707

Referring to Reaction Scheme 4, Step 3, to a solution of a compound of Formula 705 in a polar, aprotic solvent such as dichloromethane is added an excess, preferably about two equivalents of an amine base such as triethylamine, followed by about an equivalent or slight excess of an acid chloride. The resultant solution is stirred at ambient temperature for about 3 hours. Completion is monitored, e.g., by TLC. The corresponding compound of Formula 707 is isolated and purified.

Reaction Scheme 9

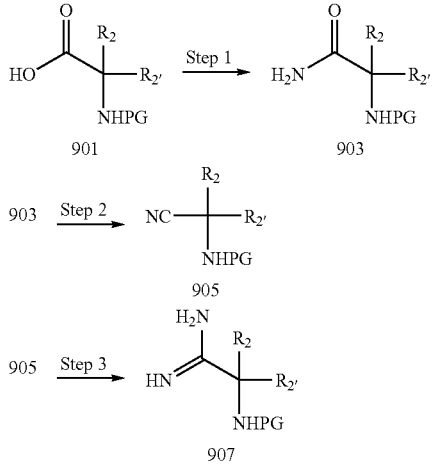

Preparation of Compounds of Formula 903

Referring to Reaction Scheme 9, Step 1, to a 0° C. solution of a compound of Formula 901 and an excess (preferably about 1.4 equivalents) of N-methyl morpholine in an anhydrous, nonpolar, aprotic solvent such tetrahydrofuran is added an excess (preferably about 1.3 eqivalents) of iso-butyl chloroformate. The resulting mixture is stirred at room temperature for about 4 hours. The flask is then equipped with a dry-ice reflux condenser and purged continuously with gaseous ammonia for about 2 hours. The resulting reaction mixture is then stirred at room temperature overnight. The product, a compound of Formula 903, is isolated and used without further purification.

Preparation of Compounds of Formula 905

Referring to Reaction Scheme 9, Step 2, to a room temperature solution of a compound of Formula 903 in a nonpolar, aprotic solvent such as dioxane is added an excess (preferably about 2.5 equivalents) of pyridine and an excess (preferably about 2 equivalents) of trifluoroacetic anhydride, successively. The resulting solution is stirred for about 4 hours until no starting material is present. The product, a compound of Formula 905, is isolated and purified.

Preparation of Compounds of Formula 907

Referring to Reaction Scheme 9, Step 3, to a room temperature solution of a compound of Formula 905 and N-acetylcysteine in a polar, protic solvent such as ethylene glycol is added solid ammonium acetate. The resulting solution is heated to about 100° C. for about 48 hours. Most of the ethylene glycol is distilled in vacuo. The product, a compound of Formula 907, is isolated and used without further purification.

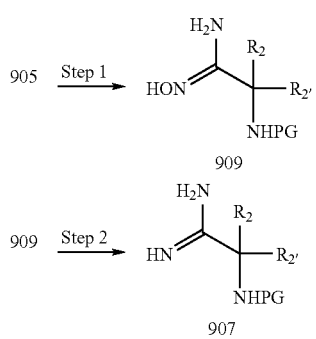

Preparation of Compounds of Formula 909

Referring to Reaction Scheme 10, Step 1, a solution of sodium methoxide in methanol (preferably, about 2 equivalents of a 0.5 M solution) is then added to a compound of Formula 905. To the resulting reaction mixture is added an excess (preferably about 2 equivalents) of hydroxylamine hydrochloride. The reaction mixture is then heated to about 50° C. overnight. The product, a compound of Formula 909, is isolated and used without further purification.

Preparation of Compounds of Formula 907

To a room temperature solution of a compound of Formula 909 in acetic acid is added an excess (preferably about 1.5 equivalents) of acetic anhydride and Pd/C. The reaction mixture is stirred under a hydrogen atmosphere for about 24 hours and then filtered through Celite. The product, a compound of Formula 907, is isolated and used without further purification.

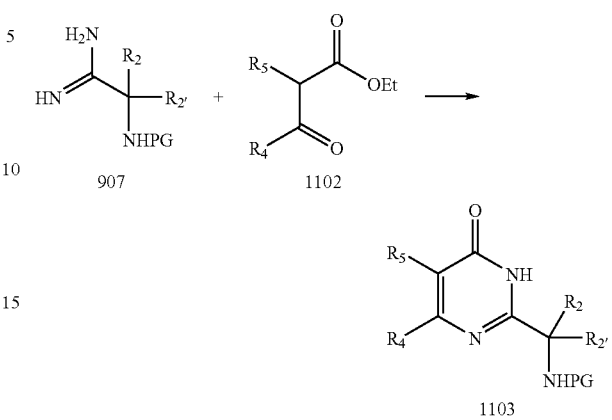

Preparation of Compounds of Formula 1103

Referring to Reaction Scheme 11, to a solution of a compound of Formula 1102 and a compound of Formula 907 is added a solution of sodium methoxide in methanol (preferably about 2.4 equivalents of a 0.5 M solution). The resulting solution is heated to about 60° C. for about 30 minutes. The product, a compound of Formula 1103, is isolated and purified.

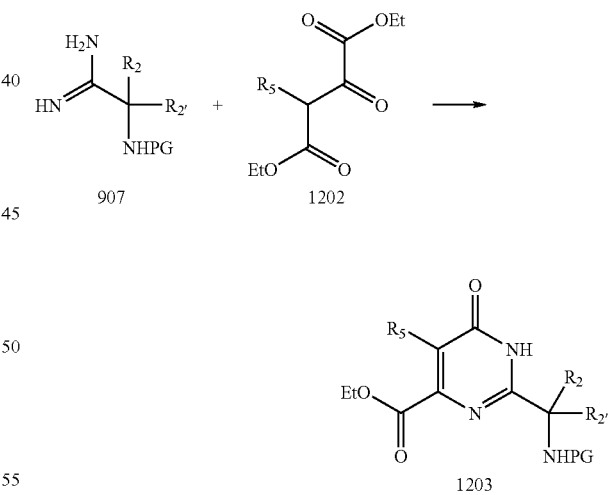

Preparation of Compounds of Formula 1203

Referring to Reaction Scheme 12, to a room temperature solution of a compound of Formula 907 and about an equivalent of diisopropylethylamine in anhydrous ethanol is added about an equivalent of a compound of Formula 1202. The resulting mixture is heated to about 70° C. for about 16 hours. The product, a compound of Formula 1203, is isolated and purified.

Reaction Scheme 13

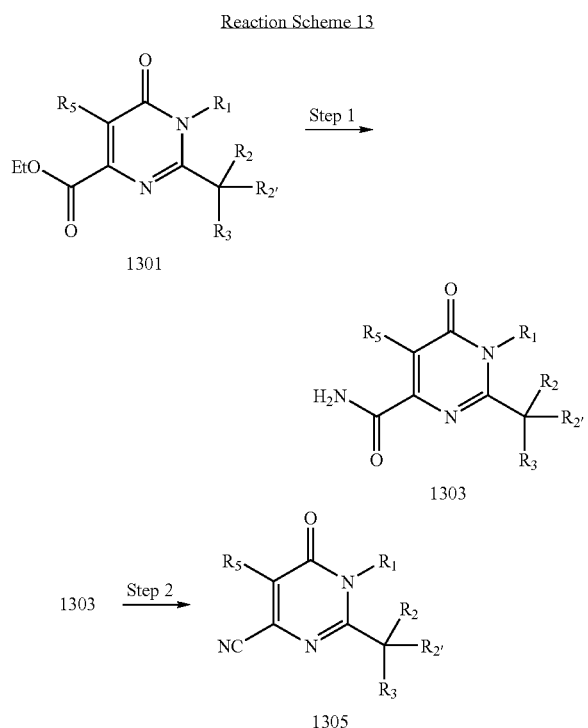

Preparation of Compounds of Formula 1303

Referring to Reaction Scheme 13, Step 1, to a room temperature solution of a compound of Formula 1301 in a polar, protic solvent such as ethanol is added concentrated aqueous ammonia. The resulting mixture is stirred at room temperature for about 24 hours. The product, a compound of Formula 1303, is isolated and purified.

Preparation of Compounds of Formula 1305

Referring to Reaction Scheme 13, Step 2, to a room temperature solution of a compound of Formula 1303 in pyridine is added an excess of thionyl chloride. The product, a compound of Formula 1305, is isolated and purified.

Reaction Scheme 14

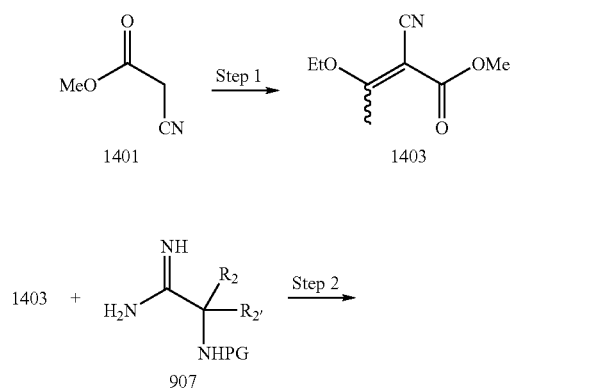

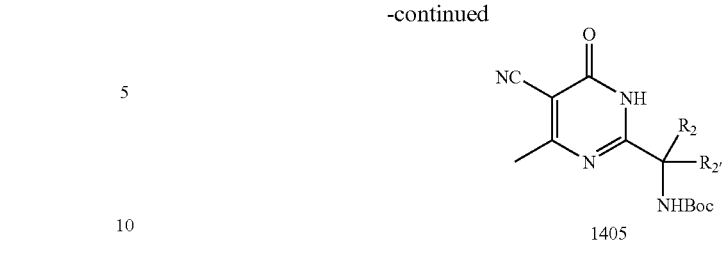

Preparation of Compounds of Formula 1403

Referring to Reaction Scheme 14, Step 1, a solution of methyl cyanoacetate of Formula 1401 and an excess (preferably about 1.1 eqivalents) of triethylorthoacetate in acetic anhydride is heated to reflux for about 3 hours. The product, a compound of Formula 1403, is isolated and used without further purification.

Preparation of Compounds of Formula 1405

Referring to Reaction Scheme 14, Step 2, to a solution of a compound of Formula 1403 and an excess (preferably about 3 equivalents) of a compound of Formula 907 in a polar, protic solvent such as methanol is added a solution of sodium methoxide in methanol (preferably, as a 0.5 M solution). The resulting solution is stirred at about 60° C. under an atmosphere of nitrogen for about 30 minutes. The product, a compound of Formula 1405, is isolated and purified.

Alternative Preparation of Compounds of Formula 1405

Referring to Reaction Scheme 14, Step 2, alternatively, to a stirred solution of a compound of Formula 907 in a polar, protic solvent such as ethanol is added about an equivalent of a compound of Formula 1403. The reaction is refluxed for about 18 h and cooled to RT. The product, a compound of Formula 1405, is isolated and purified.

Reaction Scheme 15

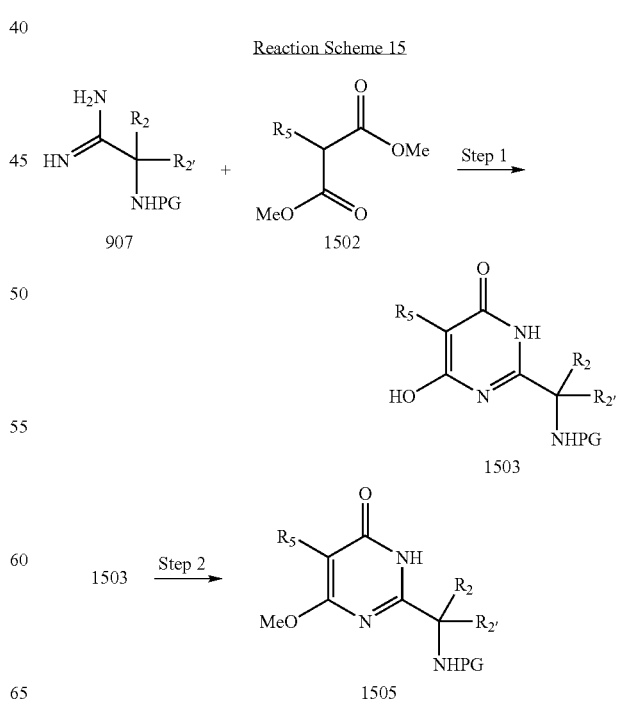

Preparation of Compounds of Formula 1503

Referring to Reaction Scheme 15, Step 1, to a room temperature solution of a compound of Formula 1502, such as an optionally substituted dialkyl malonate and an excess (preferably about 1.5 equivalents) of a compound of Formula 907 in methanol is added a solution of an excess of sodium methoxide in methanol (preferably as a 0.5 M solution in methanol). The resulting solution is heated to about 60° C. for about 4 hours. The product, a compound of Formula 1503, is isolated and used without further purification.

Preparation of Compounds of Formula 1505

Referring to Reaction Scheme 15, Step 2, to a solution of a compound of Formula 1503 in a nonpolar, aprotic solvent such as DMF is added sodium bicarbonate and dimethyl sulfate. The resulting solution is stirred at about 0° C. for about 4 hours. The product, a compound of Formula 1505, is isolated and purified.

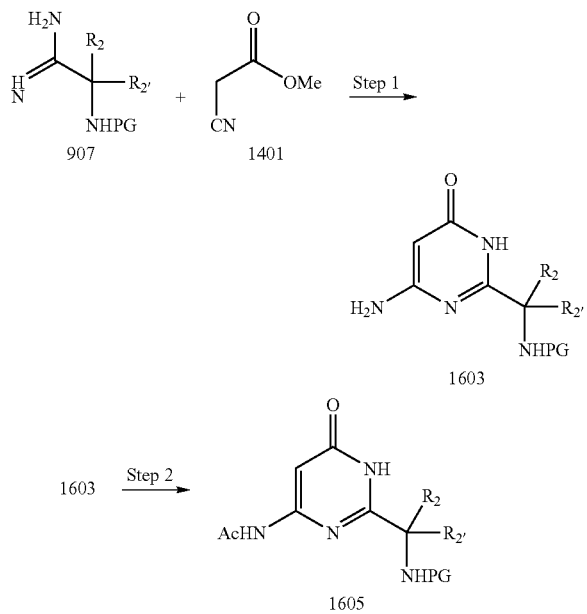

Preparation of Compounds of Formula 1603

Referring to Reaction Scheme 16, Step 1, to a room temperature solution of methyl cyanoacetate (i.e., compound of Formula 1401) and an excess (preferably about 1.5 equivalents) of a compound of Formula 907 in methanol is added a solution of sodium methoxide in methanol (preferably, about 1.8 equivalents of a 0.5 M solution in methanol). The resulting solution is heated to about 60° C. for about 4 hours. The product, a compound of Formula 1603, is isolated and used without further purification.

Preparation of Compounds of Formula 1605

To an about 0° C. solution of a compound of Formula 1603 in a nonpolar, aprotic solvent such as tetrahydrofuran are successively added diisopropylethylamine and an excess (preferably about 2 equivalents) of an acid chloride (e.g., acetyl chloride). The resulting solution is stirred at about 0° C. for about 6 hours. The product, a compound of Formula 1605, is isolated and purified.

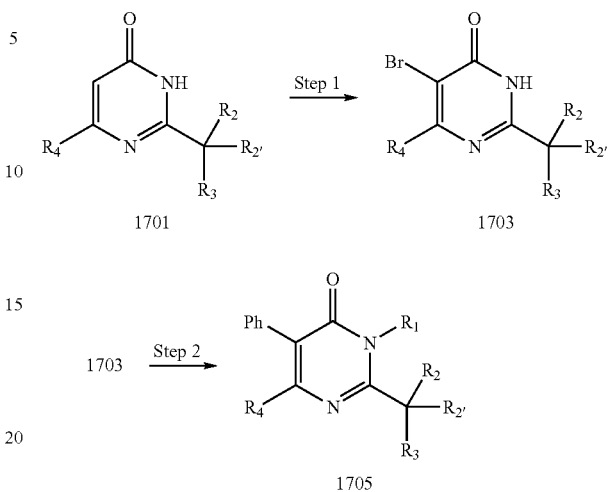

Preparation of Compounds of Formula 1703

Referring to Reaction Scheme 17, Step 1, to a room temperature solution of a compound of Formula 1701 in carbon tetrachloride is added about an equivalent of N-bromosuccinimide. The resulting mixture is heated to about 85° C. for about 1 hour. The product, a compound of Formula 1703, is isolated and purified.

Preparation of Compounds of Formula 1705

Referring to Reaction Scheme 17, Step 2, a compound of Formula 1703, about 0.2 equivalent of 2-(dicyclohexylphosphino)biphenyl, about 0.1 equivalent of palladium acetate, an excess (preferably about 1.5 equivalents) of phenylboronic acid, and an excess (preferably about 3 equivalents) of potassium fluoride are placed in a resealable Schlenk tube. The tube is evacuated and back-filled with nitrogen several times. Toluene is then added by syringe, and the resulting mixture is heated to about 80° C. for about 72 h. The product, a compound of Formula 1705, is isolated and purified.

Alternative Preparation of Compounds of Formula 1705

Referring again to Reaction Scheme 17, Step 2, a 10-mL Smith microwave reaction vial is charged with a compound of Formula 1703, about an equivalent of 3-chloroboronic acid, $Na_2CO_3$, and $PdCl_2(PPh_3)_2$ followed by $MeCN$—$H_2O$ (1:1). The mixture is purged with argon gas, sealed, and subjected to the microwave reactor for about 5 min at about 150° C. The product, a compound of Formula 1705, is isolated and purified.

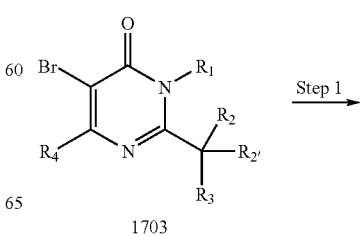

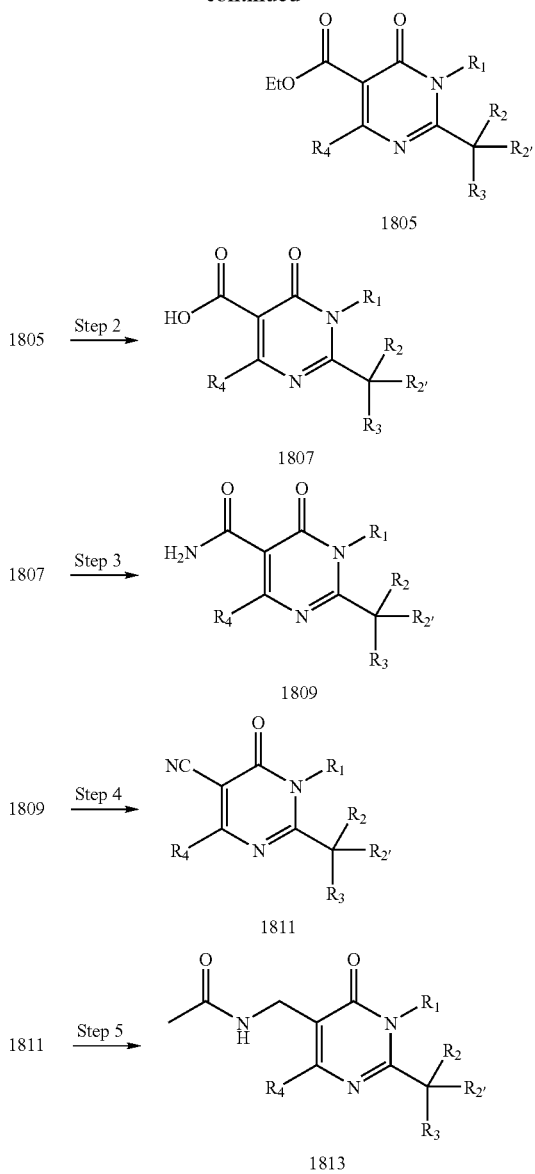

4 hours. The product, a compound of Formula 1807, is isolated and used without further purification.

Preparation of Compounds of Formula 1809

Referring to Reaction Scheme 18, Step 3, to a room temperature solution of a compound of Formula 1807 in anhydrous tetrahydrofuran are successively added an excess (preferably about 3 equivalents) of diisopropylethylamine and an excess (preferably about 1.2 equivalents) of isobutyl chloroformate. The resulting mixture is stirred for about 3 hours at room temperature under an atmosphere of nitrogen. The reaction is then cooled to about 0° C. and purged with gaseous ammonia for about 45 minutes. The mixture is then allowed to warm to room temperature for an addition 45 minutes. The product, a compound of Formula 1809, is isolated and purified.

Preparation of Compounds of Formula 1811

Referring to Reaction Scheme 18, Step 4, to a room temperature solution of a compound of Formula 1809 in pyridine is added thionyl chloride. The reaction mixture is stirred at room temperature for about 16 hours. The product, a compound of Formula 1811, is isolated and purified.

Preparation of Compounds of Formula 1813

Referring to Reaction Scheme 18, Step 5, to a stirred solution of a compound of Formula 1811 in acetic acid is carefully added 10% PDd/C. The reaction is hydrogenated under a balloon of hydrogen for about 18 hours at RT and the crude amine is isolated. To the crude amine in a nonpolar, aprotic solvent such as $CH_2Cl_2$ is added with stirring a base such as triethylamine and acetic anhydride. After stirring at RT for about 2 hours, the product, a compound of Formula 1813, is isolated and purified.

Preparation of Compounds of Formula 1805

Referring to Reaction Scheme 18, Step 1, to a solution of a compound of Formula 1703 in anhydrous ethanol in a thick-walled glass tube is added about 0.25 equivalent of 1,3-bis(diphenylphosphino)propane, an excess of triethylamine and about 0.2 equivalent of palladium acetate. The tube is evacuated and back-filled with carbon monoxide three times and then pressurized with carbon monoxide (at about 30 psi). The mixture is heated to about 70° C. for about 48 hours. The product, a compound of Formula 1805, is isolated and purified.

Preparation of Compounds of Formula 1807

Referring to Reaction Scheme 18, Step 2, to a room temperature solution of a compound of Formula 1805 in tetrahydrofuran and methanol is added aqueous potassium hydroxide. The resulting mixture is heated to about 70° C. for about Reaction Scheme 19

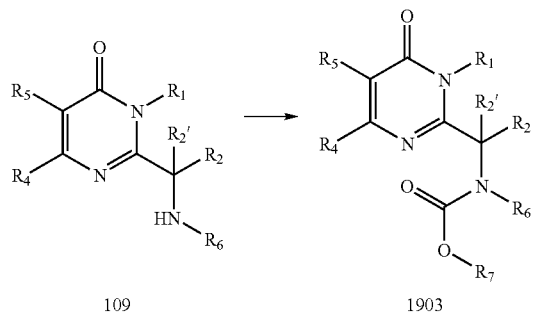

Preparation of Compounds of Formula 1903

Referring to Reaction Scheme 19, a compound of Formula 109 is reacted with a slight excess of a compound of the formula $R_7O(CO)Cl$ in the presence of a base such as triethylamine in a nonpolar, aprotic solvent such as dichloromethane. The product, a compound of Formula 1903 is isolated and purified.

Reaction Scheme 20

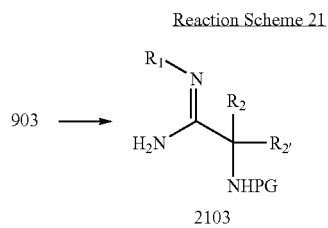

Preparation of Compounds of Formula 2003

Referring to Reaction Scheme 20, a compound of Formula 109 is treated with a slight excess of an isocyanate $R_{14}$—N=C=O in the presence of a base, such as triethylamine, in a nonpolar, aprotic solvent, such as dichloromethane. The product, a compound of Formula 2003, is isolated and purified.

Reaction Scheme 21

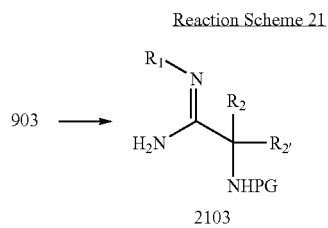

Preparation of Compounds of Formula 2103

Referring to Reaction Scheme 21, to a stirred solution of a compound of Formula 903 in a nonpolar, aprotic solvent such as $CH_2Cl_2$ is added an excess (preferably about 1.05 equivalents) of triethyloxonium hexafluorophosphate. The reaction is stirred for about 48 h at RT, poured into a separatory funnel, washed, dried, filtered and concentrated under vacuum. To the remaining oil is added a compound of formula $R_1NH_2$ and a polar, protic solvent such as ethanol. The reaction is stirred at about 60° C. for about 24 h. The product, a compound of Formula 2103, is isolated and used without purification.

Reaction Scheme 22

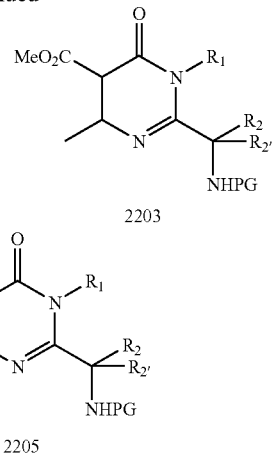

Preparation of Compounds of Formula 2203

Referring to Reaction Scheme 22, Step 1, to a solution of a compound of Formula 2103 in a polar, protic solvent such as methanol is added about an equivalent of a compound of Formula 2201 (i.e., dimethyl ethylidenemalonate). The reaction is slowly heated to about 110° C. allowing the solvent to distill off. The reaction is stirred for about 5 h at about 110° C. then allowed to cool to RT. The product, a compound of Formula 2203, is isolated and purified.

Preparation of Compounds of Formula 2205

Referring to Reaction Scheme 22, Step 2, to a stirred solution of a compound of Formula 2203 in a nonpolar, aprotic solvent such as $CCl_4$ is added $K_2CO_3$, N-bromosuccinimde, and benzoyl peroxide. The reaction is refluxed for about 0.5 h and cooled to RT. The product, a compound of Formula 2205, is isolated and purified.

Reaction Scheme 23

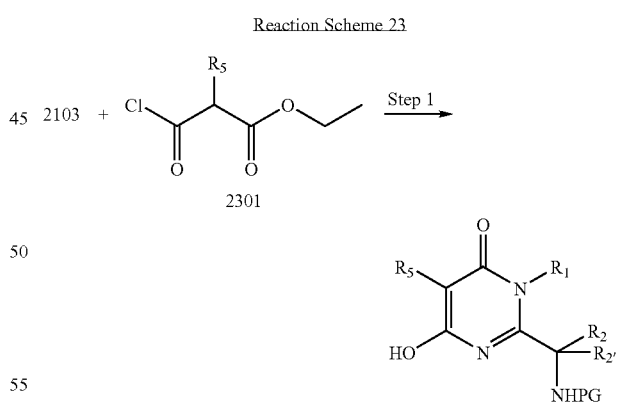

Preparation of Compounds of Formula 2303

Referring to Reaction Scheme 23, Step 1, to a stirred solution of a compound of Formula 2103 in a nonpolar, aprotic solvent such as $CH_2Cl_2$ with cooling at about 0° C. is added a base such as $Et_3N$ followed by an excess (preferably about 1.1 equivalent) of a compound of Formula 2301 (preferably, wherein $R_5$ is methyl) dropwise over about 15 minutes. The reaction is allowed to warm to RT and stirred for about 4 h. The product, a compound of Formula 2303, is isolated and purified.

Preparation of Compounds of Formula 2305

Referring to Reaction Scheme 23, Step 2, to a stirred solution of a compound of Formula 2303 is added portionwise a 60% dispersion of NaH in mineral oil. After stirring for about 15 minutes at RT, an excess (preferably, about 1.1 equivalents) of N-phenyltrifluoromethanesulfonimide is added. The reaction is stirred at RT for about 18 h. The product, the corresponding triflate, is isolated and purified. To the crude triflate with stirring in a nonpolar, aprotic solvent such as DMF is added $Zn(CN)_2$ and $(PPh_3)_4Pd$. The reaction is heated under an inert atmosphere at about 90° C. for about 4 h and cooled to RT. The product, a compound of Formula 2305, is isolated and purified.

Reaction Scheme 24

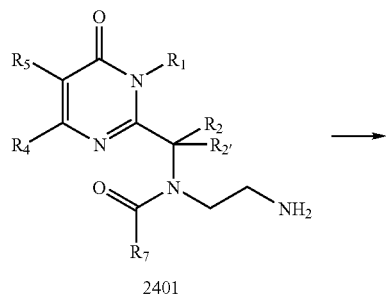

2401

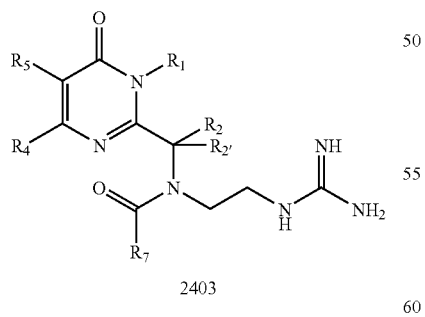

2403

To a solution of a compound of Formula 2401 in a nonpolar, aprotic solvent such as DMF is added 1H-pyrazole-1-carboxamidine hydrochloride and diisopropylethyl amine. The reaction is stirred at RT for about 16 h. The product, a compound of 2403, is isolated and purified.

Reaction Scheme 25

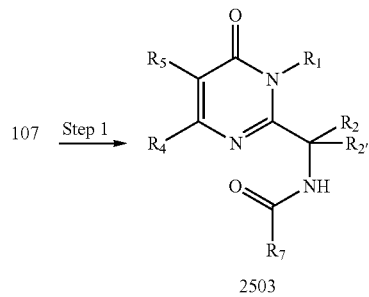

2503

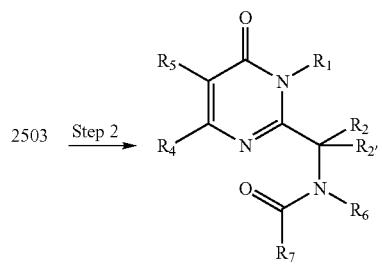

111

Preparation of Compounds of Formula 2503

Referring to Reaction Scheme 25, Step 1, to a compound of Formula 107 and a base such as triethylamine in a nonpolar, aprotic solvent such as $CH_2Cl_2$ is added a compound of Formula $R_7$—(CO)Cl. The reaction is stirred at RT for about 48 h. The product, a compound of Formula 2503, is isolated and purified.

Preparation of Compounds of Formula 111

Referring to Reaction Scheme 25, Step 2, to a compound of Formula 2503 in a nonpolar, aprotic solvent such as DMF is added a base, such as sodium hydride. The reaction is stirred for about 15 at RT then a compound of Formula $R_6$—X wherein X is a leaving group (preferably, a halide) is added. The reaction is stirred at RT for about 24 h. The product, a compound of Formula 111, is isolated and purified.

Reaction Scheme 26

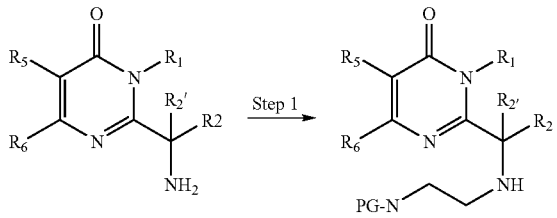

107                                                          2603

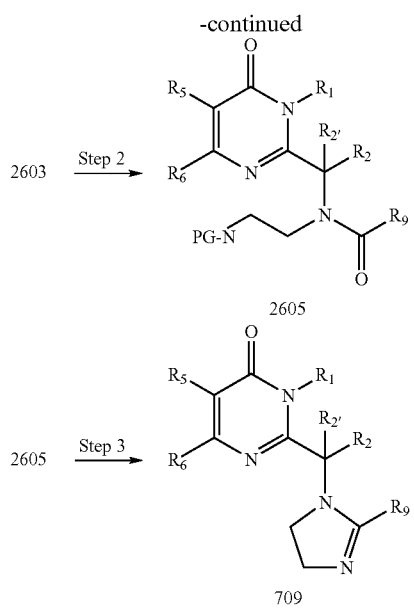

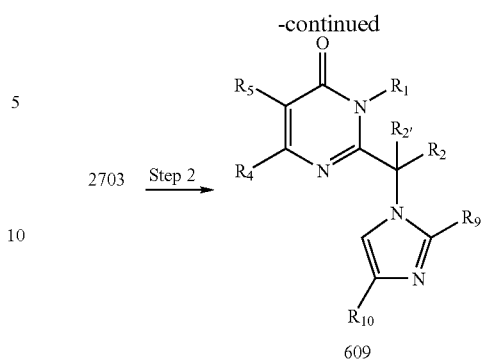

Preparation of Compounds of Formula 2703

Referring to Reaction Scheme 27, Step 1, to a compound of Formula 107 in a nonpolar, aprotic solvent such as DMF is added a compound of Formula X—$CH_2$—(CO)—$R_{10}$ (wherein X is a leaving group, preferably a halide) and a base such as N,N-diisopropylethylamine. The reaction is stirred for about 16 h at room temperature. The product is isolated and added to a nonpolar, aprotic solvent such as triethylamine and a compound of the formula $R_9$—(CO)—Cl. The reaction is stirred for about 16 h at room temperature. The product, a compound of Formula 2703, is isolated and purified.

Preparation of Compounds of Formula 609

Referring to Reaction Scheme 27, Step 2, to a compound of Formula 2703 in glacial acetic acid is added ammonium acetate and the reaction is heated at reflux for about 16 h. The product, a compound of Formula 609, is isolated and purified.

Preparation of Compounds of Formula 2603

Referring to Reaction Scheme 26, Step 1, a compound of Formula 107 and an excess of a compound of Formula PG-N—$CH_2$CHO (preferably, 2H-isoindole-2-acetaldehyde) are dissolved in a nonpolar, aprotic solvent such as dichloroethane. Glacial acetic acid is added followed by sodium triacetoxy borohydride. The reaction is stirred at room temperature under nitrogen for about 3.5 h. The product, a compound of Formula 2603, is isolated and purified.

Preparation of Compounds of Formula 2605

Referring to Reaction Scheme 26, Step 2, a slight excess (preferably about 1.1 equivalents) of a compound of the Formula $R_9$—(CO)—Cl is dissolved in a nonpolar, aprotic solvent such as toluene and is treated with a base such as followed by a compound of Formula 2603. The reaction is stirred at about 110° C. for about 3 h. The reaction is cooled to room temperature. The product, a compound of Formula 2605, is isolated and purified.

Preparation of Compounds of Formula 709

Referring to Reaction Scheme 26, Step 3, when the amino functionality is protected as the phthalidmide, the protected amine of Formula 2605, is treated with hydrazine monohydrate in a polar, protic solvent such as ethanol at about 70° C. for about 12 h. The product, a compound of Formula 709, is isolated and purified.

Reaction Scheme 27

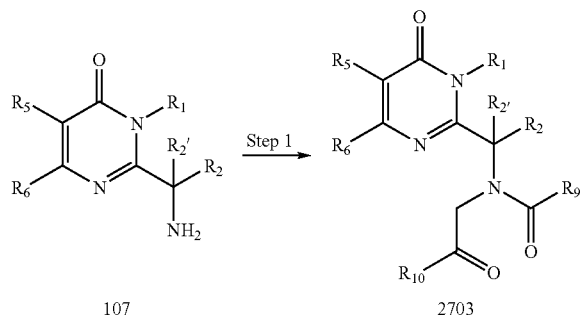

Reaction Scheme 28

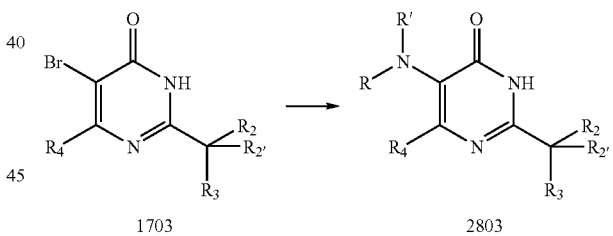

Preparation of Compounds of Formula 2803

Referring to Reaction Scheme 28, to a compound of Formula 1703 in a nonpolar, aprotic solvent such as toluene is added an amine of the formula H—NRR', a base such as NaO-tBu, $Pd_2DBA$, and (S)-BINAP. The reaction is stirred at about 90° C. for about 72 h. The product, a compound of Formula 2803, is isolated and purified.

Particular Processes and Last Steps

A compound of Formula I is optionally contacted with a pharmaceutically acceptable acid or base to form the corresponding acid or base addition salt.

A pharmaceutically acceptable acid addition salt of a compound of Formula I is optionally contacted with a base to form the corresponding free base of Formula I.

A pharmaceutically acceptable base addition salt of a compound of Formula I is optionally contacted with an acid to form the corresponding free acid of Formula I.

Particular Embodiments of Compounds of the Invention $R_1$

When considering the compounds of Formula I, in one embodiment, $R_1$ is selected from hydrogen, optionally substituted $C_1$-$C_8$ alkyl-, optionally substituted aryl-, optionally substituted heteroaryl-, optionally substituted aryl-$C_1$-$C_4$-alkyl-, and optionally substituted heteroaryl-$C_1$-$C_4$-alkyl- (more preferably optionally substituted aryl and optionally substituted aryl-$C_1$-$C_4$-alkyl-). In a more particular embodiment $R_1$ is selected from hydrogen, optionally substituted $C_1$-$C_4$ alkyl-, optionally substituted phenyl-$C_1$-$C_4$-alkyl-, optionally substituted naphthalenylmethyl-, optionally substituted phenyl-, and naphthyl-. Even more particularly, $R_1$ is optionally substituted phenyl-$C_1$-$C_4$-alkyl-, optionally substituted heteroaryl-$C_1$-$C_4$-alkyl-, or naphthalenylmethyl-.

Yet more particularly, $R_1$ is naphthyl-, phenyl-, bromophenyl-, chlorophenyl-, methoxyphenyl-, ethoxyphenyl-, tolyl-, dimethylphenyl-, chorofluorophenyl-, methylchlorophenyl-, ethylphenyl-, phenethyl-, benzyl-, chlorobenzyl-, methylbenzyl-, methoxybenzyl-, cyanobenzyl-, hydroxybenzyl-, dichlorobenzyl-, dimethoxybenzyl-, or naphthalenylmethyl-. More suitably, $R_1$ is benzyl-, cyanobenzyl-, methoxybenzyl-, or naphthalenylmethyl-. Most particularly, $R_1$ is benzyl-.

$R_2$ and $R_{2'}$

When considering the compounds of Formula I and as will be appreciated by those skilled in the art, the compounds described herein possess a potentially chiral center at the carbon to which $R_2$ and $R_{2'}$ are attached. The $R_2$ and $R_{2'}$ groups may be the same or different; if different, the compound is chiral (i.e., has a stereogenic center). When $R_2$ and $R_{2'}$ are different, in particular embodiments $R_2'$ is hydrogen and $R_2$ is other than hydrogen. The invention contemplates the use of pure enantiomers and mixtures of enantiomers, including racemic mixtures, although the use of a substantially optically pure enantiomer will generally be preferred. The term "substantially pure" means having at least about 95% chemical purity with no single impurity greater than about 1%. The term "substantially optically pure" or "enantiomerically pure" means having at least about 97.5% enantiomeric excess. In a a particular embodiment, the stereogenic center to which $R_2$ and $R_{2'}$ are attached is of the R configuration.

When considering the compounds of Formula I, $R_2$ and $R_{2'}$ are independently chosen from hydrogen, optionally substituted alkyl-, optionally substituted alkoxy, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring.

In one embodiment, $R_2$ is optionally substituted $C_1$-$C_4$ alkyl-, and $R_{2'}$ is hydrogen or optionally substituted $C_1$-$C_4$ alkyl-. More suitably, $R_{2'}$ is hydrogen and $R_2$ is optionally substituted $C_1$-$C_4$ alkyl-. In a most particular embodiment $R_2$ is chosen from methyl-, ethyl-, propyl (particularly, c-propyl or i-propyl), butyl (particularly, t-butyl), methylthioethyl-, methylthiomethyl-, aminobutyl-, (CBZ)aminobutyl-, cyclohexylmethyl-, benzyloxymethyl-, methylsulfanylethyl-, methylsulfanylmethyl-, and hydroxymethyl-, and $R_{2'}$ is hydrogen. Especially chosen embodiments are when $R_{2'}$ is hydrogen and $R_2$ is ethyl or propyl (particularly, c-propyl or i-propyl). Even more particularly, $R_2$ is i-propyl. Yet more particularly, the stereogenic center to which $R_2$ and $R_{2'}$ is attached is of the R configuration.

In one embodiment, if either $R_2$ or $R_{2'}$ is hydrogen, then the other is not hydrogen. In another embodiment, both $R_2$ and $R_{2'}$ are hydrogen.

$R_4$ and $R_5$

When considering the compounds of Formula I, in one embodiment, $R_4$ is hydrogen; acyl-; alkoxy; cyano; carboxy, carboxamido; aminocarbonyl-; lower-alkyl-; lower-alkyl substituted with one or more of the following substituents: halo, lower-alkoxy, or hydroxy; phenyl-; or phenyl substituted with one or more of the following substituents: halo, lower-alkoxy, or hydroxy. More particularly, $R_4$ is hydrogen, cyano, methyl, or methyl substituted with one or more of the following substituents: halo, lower-alkoxy, or hydroxy (particularly, halo, e.g., —$CF_3$).

When considering the compounds of Formula I, in one embodiment, $R_5$ is hydrogen; acyl-; carboxy; carboxamido; cyano; lower-alkyl (especially, methyl or ethyl); halo (especially, bromo, chloro or fluoro); benzyl-; piperonyl-; naphthyl-; furyl-; thienyl-; indolyl-; morpholinyl-; phenyl-; benzodioxolyl-; or phenyl substituted with one or more of the following substituents: optionally substituted amino, dialkylamino, acylamino (e.g., acetylamino), cyano, halo, optionally substituted lower-alkyl-(including trifluoromethyl and hydroxy alkyl such as hydroxymethyl), optionally substituted lower-alkoxy, optionally substituted lower-alkyl sulfanyl (including methylsulfanyl), hydroxy, or thio.

More suitably, $R_5$ is methyl-; ethyl-; bromo; carboxy; cyano; phenyl-; halophenyl-; lower-alkylphenyl-; trifluoromethylphenyl-; lower-alkoxyphenyl-; di(lower-alkoxy)phenyl-; polyhalophenyl-; halo lower-alkylphenyl (e.g., halomethylphenyl-); furyl-; thienyl-; lower-alkylsulfanylphenyl-; thiophenyl-; aminophenyl-; aminocarbonylphenyl-; cyanophenyl-; di(lower-alkyl)aminophenyl-; di(lower-alkyl) phenyl-; acetylaminophenyl-; amino substituted lower-alkylphenyl-; hydroxy substituted lower-alkylphenyl- (e.g., methylhydroxyphenyl-); piperonyl-; naphthyl-; carbamoyl-; lower-alkyl carbamoyl- (e.g., methyl, ethyl, or propyl carbamoyl); benzylcarbamoyl-; phenylcarbamoyl-; methoxymethyl carbamoyl-; methoxyethyl carbamoyl-; hydroxymethyl carbamoyl-; hydroxyethyl carbamoyl-; indolyl-; oxalyl-; morpholinyl-; cyano; carboxy; and morpholinocarbonyl-.

More suitably, $R_5$ is hydrogen, methyl, or cyano.

When considering the compounds of Formula I, in another embodiment, $R_4$ and $R_5$ taken together with the carbons to which they are attached form an optionally substituted 5-, 6- or 7-membered aliphatic carbocyclic ring. The ring may be substituted with one or more of the following substituents: halo, optionally substituted lower-alkyl-, optionally substituted lower-alkoxy, and/or hydroxy.

Compounds wherein $R_3$ is an Optionally Substituted Imidazolyl

When $R_3$ is an optionally substituted imidazolyl-, in particular embodiments, $R_3$ has the formula:

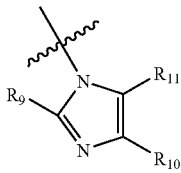

wherein

R$_9$ is chosen from hydrogen, optionally substituted C$_1$-C$_8$ alkyl-, optionally substituted aryl-, optionally substituted aryl-C$_1$-C$_4$-alkyl-, optionally substituted heteroaryl-C$_1$-C$_4$-alkyl-, optionally substituted aryl-C$_1$-C$_4$-alkoxy, optionally substituted heteroaryl-C$_1$-C$_4$-alkoxy, and optionally substituted heteroaryl-; and R$_{10}$ and R$_{11}$ are independently hydrogen, optionally substituted C$_1$-C$_8$ alkyl-, optionally substituted aryl-, or optionally substituted aryl-C$_1$-C$_4$-alkyl-.

According to one embodiment, R$_9$ is phenyl substituted with C$_1$-C$_4$-alkyl-, C$_1$-C$_4$-alkoxy-, and/or halo; phenyl-; benzyl-; thiophenyl-; or thiophenyl-substituted with C$_1$-C$_4$-alkyl-, C$_1$-C$_4$-alkoxy, and/or halo. More suitably, R$_9$ is phenyl substituted with one or more halo and/or methyl.

According to another embodiment, R$_{11}$ is hydrogen and R$_{10}$ is substituted C$_1$-C$_4$ alkyl-. More suitably, R$_{11}$ is hydrogen and R$_{10}$ is aminomethyl-, aminoethyl-, aminopropyl-, acetylamino-methyl-, acetylaminoethyl-, benzyloxycarbonylamino-methyl- or benzyloxycarbonylamino-ethyl-.

Compounds wherein R$_3$ is an Optionally Substituted Imidazolinyl

When R$_3$ is an imidazoline, in one embodiment, R$_3$ has the formula

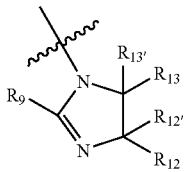

wherein,

R$_9$ is chosen from hydrogen, optionally substituted C$_1$-C$_8$ alkyl-, optionally substituted aryl-, optionally substituted aryl-C$_1$-C$_4$-alkyl-, optionally substituted heteroaryl-, optionally substituted heteroaryl-C$_1$-C$_4$-alkyl-; and R$_{12}$, R$_{12'}$, R$_{13}$, and R$_{13'}$ are independently chosen from hydrogen, optionally substituted C$_1$-C$_8$ alkyl-, optionally substituted aryl-, and optionally substituted aryl-C$_1$-C$_4$-alkyl-.

In one embodiment, R$_9$ is methylenedioxyphenyl-; phenyl-; phenyl substituted with C$_1$-C$_4$ alkyl-, C$_1$-C$_4$ alkoxy-, and/or halo; benzyl-; thienyl substituted with C$_1$-C$_4$ alkyl; benzyl; thiophenyl-; or thiophenyl- substituted with C$_1$-C$_4$-alkyl-, C$_1$-C$_4$-alkoxy-, and/or halo. More suitably, R$_9$ is methylenedioxyphenyl-; phenyl-; tolyl-; methoxyphenyl-; or halomethylphenyl-.

In one embodiment, R$_{12}$, R$_{12'}$, R$_{13'}$, and R$_{13}$ are independently hydrogen or optionally substituted C$_1$-C$_4$ alkyl-. More suitably, R$_{13'}$ and R$_{13}$ are hydrogen.

Compounds wherein R$_3$ is —NHR$_6$, —NR$_6$(COR$_7$), or —NR$_6$(CH$_2$R$_{7b}$)

In one embodiment, R$_6$ is chosen from hydrogen, optionally substituted alkyl-, optionally substituted aryl-, optionally substituted aralkyl-, optionally substituted heteroaralkyl-, and optionally substituted heterocyclyl-. More suitably, R$_6$ is R$_{16}$-alkylene-, and R$_{16}$ is chosen from alkoxy, amino, alkylamino, dialkylamino, carboxy, guanidine, hydroxyl-, and N-heterocyclyl-.

In a more particular embodiment, R$_6$ is selected from optionally substituted lower-alkyl-, optionally substituted cyclohexyl-; phenyl substituted with hydroxy, lower-alkoxy or lower-alkyl-; benzyl-; heteroarylmethyl-; heteroarylethyl-; and heteroarylpropyl-.

In a most particular embodiment, R$_6$ is chosen from methyl-, ethyl-, propyl-, butyl-, cyclohexyl-, carboxyethyl-, carboxymethyl-, methoxyethyl-, hydroxyethyl-, hydroxypropyl-, dimethylaminoethyl-, dimethylaminopropyl-, diethylaminoethyl-, diethylaminopropyl-, aminopropyl-, methylaminopropyl-, 2,2-dimethyl-3-(dimethylamino)propyl-, 1-cyclohexyl-4-(diethylamino)butyl-, aminoethyl-, aminobutyl-, aminopentyl-, aminohexyl-, aminoethoxyethyl-, isopropylaminopropyl-, diisopropylaminoethyl-, 1-methyl-4-(diethylamino)butyl-, (t-Boc)aminopropyl-, hydroxyphenyl-, benzyl-, methoxyphenyl-, methylmethoxyphenyl-, dimethylphenyl-, tolyl-, ethylphenyl-, (oxopyrrolidinyl)propyl-, (methoxycarbonyl)ethyl-, benzylpiperidinyl-, pyridinylethyl-, pyridinylmethyl-, morpholinylethyl morpholinylpropyl-, piperidinyl-, azetidinylmethyl-, azetidinylethyl-azetidinylpropyl-, pyrrolidinylmethyl-, pyrrolidinylethyl-, pyrrolidinylpropyl-, piperidinylmethyl-, piperidinylethyl-, imidazolylpropyl-, imidazolylethyl-, (ethylpyrrolidinyl)methyl-, (methylpyrrolidinyl)ethyl-, (methylpiperidinyl)propyl-, (methylpiperazinyl)propyl-, guanidino-ethyl-, guanidino-propyl-, furanylmethyl and indolyl-ethyl-.

When considering the compounds of Formula I, in a particular embodiment R$_7$ is selected from hydrogen, optionally substituted alkyl-, optionally substituted aralkyl-, optionally substituted heteroaralkyl-, optionally substituted heteroaryl-, optionally substituted aryl-, R$_8$O— and R$_{14}$—NH—, wherein R$_8$ is chosen from optionally substituted alkyl and optionally substituted aryl and R$_{14}$ is chosen from hydrogen, optionally substituted alkyl and optionally substituted aryl-.

In a more particular embodiment, when R$_7$ is not R$_{14}$NH— or R$_8$O—, R$_7$ is chosen from optionally substituted alkyl-; aryl- (including phenyl-, biphenyl-, and naphthyl-); substituted aryl- (including phenyl substituted with one or more cyano, halo, lower-alkyl-, lower-alkoxy, hydroxy-lower-alkyl-, nitro, carboxy, methylenedioxy, trifluoromethoxy, or trifluoromethyl-); benzyl-; and optionally substituted heteroaryl-.

In a most particular embodiment, when R$_7$ is not R$_{14}$NH— or R$_8$O—, R$_7$ is chosen from ethyl-, propyl-, chloropropyl-, butoxy, heptyl-, butyl-, octyl-, tridecanyl-, (ethoxycarbonyl) ethyl-, dimethylaminoethyl-, dimethylaminomethyl-, phenyl-, naphthyl-, halophenyl-, polyhalophenyl-, cyanophenyl-, hydroxymethylphenyl-, halo(trifluoromethyl)phenyl-, chlorophenoxymethyl-, methoxyphenyl-, carboxyphenyl-, ethylphenyl-, tolyl-, hydroxymethylphenyl-; ethylphenyl-; biphenylyl-, methylenedioxyphenyl-, methylsulfonylphenyl-, methoxychlorophenyl-, chloronaphthyl-, acetylphenyl-, methylhalophenyl-, trifluoromethylphenyl-, trifluoromethoxyphenyl-, butylphenyl-, pentylphenyl-, methylnitrophenyl-, phenoxymethyl-, dimethoxyphenyl-, phenylvinyl-, nitrochlorophenyl-, nitrophenyl-, dinitrophenyl-, bis(trifluoromethyl)phenyl-, benzyloxymethyl-, benzyl-, furanyl-, benzofuranyl-, pyridinyl-, pyridyl-, indolyl-, methylpyridinyl-, methylpyridyl-, (3-carbamoyl)pyridinyl-[nicotinamide], 3-carbamoyl-6-methylpyridinyl-, quinolinyl-, picolinyl-, pyrazolyl-, pyrazinyl-, methylpyrazinyl-, morpholinomethyl-, methylthiomethyl-, methoxymethyl-, imidazolyl-; isoxazolyl-, methyl-isoxazolyl-; benzothiadiazolyl-; methylenedioxyphenyl-, thienyl-, methylthienyl-, methyl-nicotinamidyl-; methyl-pyrazinyl; benzodioxolyl; and methyl-thiophenyl-.

More suitably, $R_7$ is tolyl-, halophenyl-, halomethylphenyl-, hydroxymethylphenyl-, methylenedioxyphenyl-, formylphenyl or cyanophenyl-.

In another particular embodiment, when $R_7$ is $R_{14}NH$—, $R_{14}$ is chosen from lower-alkyl-; cyclohexyl-; phenyl-; and phenyl substituted with halo, lower-alkyl-, loweralkoxy, or lower-alkylsulfanyl-.

In another particular embodiment, when $R_7$ is $R_{14}NH$—, $R_{14}$ is isopropyl-, butyl-, cyclohexyl-, phenyl-, bromophenyl-, dichlorophenyl-, methoxyphenyl-, ethylphenyl-, tolyl-, trifluoromethylphenyl or methylthiophenyl-.

In a particular embodiment, when $R_7$ is $R_8O$—, $R_8$ is chosen from lower-alkyl-; cyclohexyl-; phenyl-; and phenyl substituted with halo, lower-alkyl-, loweralkoxy, or lower-alkylsulfanyl-.

In a most particular embodiment, when $R_7$ is $R_8O$—, $R_8$ is isopropyl-, butyl-, cyclohexyl-, phenyl-, bromophenyl-, dichlorophenyl-, methoxyphenyl-, ethylphenyl-, tolyl-, trifluoromethylphenyl or methylthiophenyl-.

Suitably, $R_{7b}$ is chosen from $C_1$-$C_{13}$ alkyl-; substituted lower-alkyl-; phenyl-; naphthyl-; phenyl substituted with cyano, halo, lower-alkyl-, lower-alkoxy, nitro, methylenedioxy, or trifluoromethyl-; biphenylyl-, benzyl and heterocyclyl-. Most suitably, $R_{7b}$ is chosen from phenyl substituted with one or more halo, methyl-, cyano, trifluoromethyl-, trifluoromethoxy, carboxy, or methoxycarbonyl groups; piperidinyl-; and naphthyl-. Even more suitably, $R_{7b}$ is halophenyl-, methylhalophenyl-, polyhalophenyl-, tolyl-, dimethylphenyl-, methoxyphenyl-, dimethoxyphenyl-, cyanophenyl-, trifluoromethylphenyl-, trifluorometoxyphenyl-, bis(trifluoromethyl)phenyl-, carboxyphenyl-, t-butylphenyl-, methoxycarbonylphenyl-, piperidinyl-, and naphthyl-.

Compounds wherein $R_3$ is —$NR_6(SO_2R_{7a})$

When $R_3$ is —$NR_6(SO_2R_{7a})$, $R_6$ is as described above and $R_{7a}$ is chosen from $C_1$-$C_{13}$ alkyl-; phenyl-; naphthyl-; phenyl substituted with cyano, halo, lower-alkyl-, lower-alkoxy, nitro, methylenedioxy, or trifluoromethyl-; biphenylyl and heteroaryl-. More suitably, $R_{7a}$ is chosen from phenyl substituted with halo, lower-alkyl-, lower-alkoxy, cyano, nitro, methlenedioxy, or trifluoromethyl-; and naphthyl-.

Particular Subgenus

In a particular subgenus of compounds of Formula I,
$R_1$ is optionally substituted aryl-$C_1$-$C_4$-alkyl-, optionally substituted heteroaryl-$C_1$-$C_4$-alkyl-, or naphthalenylmethyl;
$R_2$ is optionally substituted $C_1$-$C_4$-alkyl-;
$R_{2'}$ is hydrogen;
$R_4$ is hydrogen, cyano, or methyl substituted with one or more of the following substituents: halo, lower-alkoxy, or hydroxy;
$R_5$ is hydrogen, methyl, or cyano; and
$R_3$ is optionally substituted imidazolyl-, optionally substituted imidazolinyl-, —$NHR_6$; —$N(R_6)(COR_7)$; —$N(R_6)(SO_2R_{7a})$; and —$N(R_6)(CH_2R_{7b})$.

In a particular subgenus of compounds of Formula I wherein $R_3$ is optionally substituted imidazolyl-,
$R_1$, $R_2$, $R_{2'}$, $R_4$, and $R_5$ are as defined above;
$R_9$ is phenyl substituted with one or more halo and/or methyl; and
$R_{11}$ is hydrogen and $R_{10}$ is substituted $C_1$-$C_4$ alkyl- (especially, aminomethyl-, aminoethyl-, aminopropyl-, acetylamino-methyl-, acetylaminoethyl-, benzyloxycarbonylamino-methyl- or benzyloxycarbonylaminoethyl-.)

In a particular subgenus of compounds of Formula I wherein $R_3$ is optionally substituted imidazolinyl-,
$R_1$, $R_2$, $R_{2'}$, $R_4$, and $R_5$ are as defined above;
$R_9$ is methylenedioxyphenyl-; phenyl-; tolyl-; methoxyphenyl-; or halomethylphenyl-; and
$R_{12}$, $R_{12'}$, $R_{13}$, and $R_{13'}$ are independently hydrogen or optionally substituted $C_1$-$C_4$ alkyl-. More particularly, $R_{13'}$ and $R_{13}$ are hydrogen.

In a particular subgenus of compounds of Formula I wherein $R_3$ is —$NR_6$,
$R_1$, $R_2$, $R_{2'}$, $R_4$, and $R_5$ are as defined above;
$R_6$ is chosen from hydrogen, optionally substituted alkyl-, optionally substituted aryl-, optionally substituted aralkyl-, optionally substituted heteroaralkyl-, and optionally substituted heterocyclyl-.

In a particular subgenus of compounds of Formula I wherein $R_3$ is —$NR_6(COR_7)$,
$R_1$, $R_2$, $R_{2'}$, $R_4$, and $R_5$ are as defined above;
$R_6$ is chosen from hydrogen, optionally substituted alkyl-, optionally substituted aryl-, optionally substituted aralkyl-, optionally substituted heteroaralkyl-, and optionally substituted heterocyclyl- and
$R_7$ is selected from hydrogen, optionally substituted alkyl-, optionally substituted aralkyl-, optionally substituted heteroaralkyl-, optionally substituted heteroaryl-, optionally substituted aryl-, $R_8O$— and $R_{14}$—NH—, wherein $R_8$ is chosen from optionally substituted alkyl and optionally substituted aryl and $R_{14}$ is chosen from hydrogen, optionally substituted alkyl and optionally substituted aryl.

More particularly, $R_1$, $R_2$, $R_{2'}$, $R_4$, and $R_5$ are as defined above;
$R_6$ is $R_{16}$-alkylene-, and $R_{16}$ is chosen from alkoxy, amino, alkylamino, dialkylamino, carboxy, hydroxyl-, and N-heterocyclyl- (especially, $R_6$ is selected from optionally substituted lower-alkyl-, optionally substituted cyclohexyl-; phenyl substituted with hydroxy, loweralkoxy or lower-alkyl-; benzyl-; heteroarylmethyl-; heteroarylethyl-; heteroarylpropyl-);
and
$R_7$ is selected from hydrogen, optionally substituted alkyl-, optionally substituted aralkyl-, optionally substituted heteroaralkyl-, optionally substituted heteroaryl-, optionally substituted aryl-, $R_8O$— and $R_{14}$—NH—, wherein $R_8$ is chosen from optionally substituted alkyl and optionally substituted aryl and $R_{14}$ is chosen from hydrogen, optionally substituted alkyl and optionally substituted aryl.

In a particular subgenus of compounds of Formula I wherein $R_3$ is —$NR_6(COR_7)$,
$R_1$, $R_2$, $R_{2'}$, $R_4$, and $R_5$ are as defined above;
$R_6$ is chosen from hydrogen, optionally substituted alkyl-, optionally substituted aryl-, optionally substituted aralkyl-, optionally substituted heteroaralkyl-, and optionally substituted heterocyclyl- and
and
$R_7$ is selected from optionally substituted alkyl-; aryl-; substituted aryl-; benzyl-; and optionally substituted heteroaryl-.

In a particular subgenus of compounds of Formula I wherein $R_3$ is —$NR_6(COR_7)$.

$R_1$, $R_2$, $R_{2'}$, $R_4$, $R_5$ and $R_6$ are as defined above; and $R_7$ is tolyl-, halophenyl-, halomethylphenyl-, hydroxymethylphenyl-, methylenedioxyphenyl-, formylphenyl or cyanophenyl-.

In a particular subgenus of compounds of Formula I wherein $R_3$ is —$N(R_6)(CH_2R_{7b})$, $R_1$, $R_2$, $R_{2'}$, $R_4$, and $R_5$ are as defined above;

$R_6$ is chosen from hydrogen, optionally substituted alkyl-, optionally substituted aryl-, optionally substituted aralkyl-, optionally substituted heteroaralkyl-, and optionally substituted heterocyclyl- and $R_{7b}$ is chosen from phenyl substituted with one or more halo, methyl-, cyano, trifluoromethyl-, trifluoromethoxy, carboxy, or methoxycarbonyl groups; piperidinyl-; and naphthyl-.

In a particular subgenus of compounds of Formula I wherein $R_3$ is —$NR_6(SO_2R_{7a})$, $R_1$, $R_2$, $R_{2'}$, $R_4$, and $R_5$ are as defined above;

$R_6$ is chosen from hydrogen, optionally substituted alkyl-, optionally substituted aryl-, optionally substituted aralkyl-, optionally substituted heteroaralkyl-, and optionally substituted heterocyclyl- and $R_{7a}$ is chosen from phenyl substituted with halo, loweralkyl-, lower-alkoxy, cyano, nitro, methlenedixoy, or trifluoromethyl-; and naphthyl-.

Particular compounds include:

N-(3-Amino-propyl)-N-[1-(1-benzyl-5-cyano-4-methyl-6-oxo-1,6-dihydro-pyrimidin-2-yl)-2-methyl-propyl]-4-methyl-benzamide;

N-(3-Amino-propyl)-N-[1-(1-benzyl-5-cyano-4-methyl-6-oxo-1,6-dihydro-pyrimidin-2-yl)-2-methyl-propyl]-3-fluoro-4-methyl-benzamide;

N-(3-Amino-propyl)-N-[1-(1-benzyl-5-cyano-4-methyl-6-oxo-1,6-dihydro-pyrimidin-2-yl)-2-methyl-propyl]-4-ethyl-benzamide;

N-(3-Amino-propyl)-N-[1-(1-benzyl-5-cyano-4-methyl-6-oxo-1,6-dihydro-pyrimidin-2-yl)-2-methyl-propyl]-4-fluoro-benzamide;

N-(3-Amino-propyl)-N-[1-(1-benzyl-5-cyano-4-methyl-6-oxo-1,6-dihydro-pyrimidin-2-yl)-2-methyl-propyl]-4-chloro-benzamide;

N-(3-Amino-propyl)-N-[1-(1-benzyl-5-cyano-4-methyl-6-oxo-1,6-dihydro-pyrimidin-2-yl)-2-methyl-propyl]-4-bromo-benzamide;

N-(3-Amino-propyl)-N-[1-(1-benzyl-5-cyano-4-methyl-6-oxo-1,6-dihydro-pyrimidin-2-yl)-2-methyl-propyl]-4-trifluoromethyl-benzamide;

N-(3-Amino-propyl)-N-[1-(1-benzyl-5-cyano-4-methyl-6-oxo-1,6-dihydro-pyrimidin-2-yl)-2-methyl-propyl]-4-trifluoromethoxy-benzamide;

N-(3-Amino-propyl)-N-[1-(1-benzyl-5-cyano-4-methyl-6-oxo-1,6-dihydro-pyrimidin-2-yl)-2-methyl-propyl]-3-methyl-benzamide;

N-(3-Amino-propyl)-N-[1-(1-benzyl-5-cyano-4-methyl-6-oxo-1,6-dihydro-pyrimidin-2-yl)-2-methyl-propyl]-3-fluoro-benzamide;

N-(3-Amino-propyl)-N-[1-(1-benzyl-5-cyano-4-methyl-6-oxo-1,6-dihydro-pyrimidin-2-yl)-2-methyl-propyl]-3-chloro-benzamide;

N-(3-Amino-propyl)-N-[1-(1-benzyl-5-cyano-4-methyl-6-oxo-1,6-dihydro-pyrimidin-2-yl)-2-methyl-propyl]-3-cyano-benzamide;

N-(3-Amino-propyl)-N-[1-(1-benzyl-5-cyano-4-methyl-6-oxo-1,6-dihydro-pyrimidin-2-yl)-2-methyl-propyl]-4-fluoro-3-methyl-benzamide;

N-(3-Amino-propyl)-N-[1-(1-benzyl-5-cyano-4-methyl-6-oxo-1,6-dihydro-pyrimidin-2-yl)-2-methyl-propyl]-3-chloro-4-fluoro-benzamide;

N-(3-Amino-propyl)-N-[1-(1-benzyl-5-cyano-4-methyl-6-oxo-1,6-dihydro-pyrimidin-2-yl)-2-methyl-propyl]-4-fluoro-3-trifluoromethyl-benzamide;

N-(3-Amino-propyl)-N-[1-(1-benzyl-5-cyano-4-methyl-6-oxo-1,6-dihydro-pyrimidin-2-yl)-2-methyl-propyl]-3,4-difluoro-benzamide;

N-(3-Amino-propyl)-N-[1-(1-benzyl-5-cyano-4-methyl-6-oxo-1,6-dihydro-pyrimidin-2-yl)-2-methyl-propyl]-3,4-dimethoxy-benzamide;

N-(3-Amino-propyl)-N-[1-(1-benzyl-4,5-dimethyl-6-oxo-1,6-dihydro-pyrimidin-2-yl)-2-methyl-propyl]-4-methyl-benzamide;

N-[1-(1-Benzyl-4,5-dimethyl-6-oxo-1,6-dihydro-pyrimidin-2-yl)-2-methyl-propyl]-4-methyl-N-(2-pyrrolidin-1-yl-ethyl)-benzamide;

N-[1-(1-Benzyl-4,5-dimethyl-6-oxo-1,6-dihydro-pyrimidin-2-yl)-2-methyl-propyl]-4-methyl-N-pyrrolidin-3-ylmethyl-benzamide;

N-[1-(1-Benzyl-4,5-dimethyl-6-oxo-1,6-dihydro-pyrimidin-2-yl)-2-methyl-propyl]-4-methyl-N-pyrrolidin-2-ylmethyl-benzamide;

N-[1-(1-Benzyl-4,5-dimethyl-6-oxo-1,6-dihydro-pyrimidin-2-yl)-2-methyl-propyl]-4-methyl-N-piperidin-4-ylmethyl-benzamide;

N-Azetidin-3-ylmethyl-N-[1-(1-benzyl-4,5-dimethyl-6-oxo-1,6-dihydro-pyrimidin-2-yl)-2-methyl-propyl]-4-methyl-benzamide;

N-(3-Amino-propyl)-N-[1-(1-benzyl-4-cyano-5-methyl-6-oxo-1,6-dihydro-pyrimidin-2-yl)-2-methyl-propyl]-4-methyl-benzamide;

N-(2-Amino-ethyl)-N-[1-(1-benzyl-4-cyano-5-methyl-6-oxo-1,6-dihydro-pyrimidin-2-yl)-2-methyl-propyl]-4-methyl-benzamide;

N-[1-(1-Benzyl-4-cyano-5-methyl-6-oxo-1,6-dihydro-pyrimidin-2-yl)-2-methyl-propyl]-N-(2-guanidino-ethyl)-4-methyl-benzamide;

N-(3-Amino-propyl)-N-{1-[1-(3-methoxy-benzyl)-4,5-dimethyl-6-oxo-1,6-dihydro-pyrimidin-2-yl]-2-methyl-propyl}-4-methyl-benzamide;

3-Benzyl-5,6-dimethyl-2-[2-methyl-1-(2-p-tolyl-4,5-dihydro-imidazol-1-yl)-propyl]-3H-pyrimidin-4-one;

1-Benzyl-5-methyl-2-[2-methyl-1-(2-p-tolyl-4,5-dihydro-imidazol-1-yl)-propyl]-6-oxo-1,6-dihydro-pyrimidine-4-carbonitrile;

N-[1-(5-Acetyl-1-benzyl-4-methyl-6-oxo-1,6-dihydro-pyrimidin-2-yl)-2-methyl-propyl]-N-(3-amino-propyl)-4-methyl-benzamide;

2-{1'-[(3-Amino-propyl)-(4-methyl-benzoyl)-amino]-2-methyl-propyl}-1-benzyl-4-methyl-6-oxo-1,6-dihydro-pyrimidine-5-carboxylic acid amide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid methylamide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid ethylamide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid benzylamide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid phenylamide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid(acetylamino-methyl)-amide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid methoxymethyl-amide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid hydroxymethyl-amide;

N-(3-Amino-propyl)-N-{1-[1-benzyl-4-methyl-5-(morpholine-4-carbonyl)-6-oxo-1,6-dihydro-pyrimidin-2-yl]-2-methyl-propyl}-4-methyl-benzamide;

(2-{1-[(3-Amino-propyl)-(4-methyl-benzoyl)-amino]-2-methyl-propyl}-1-benzyl-4-methyl-6-oxo-1,6-dihydro-pyrimidin-5-yl)-oxo-acetic acid;

N-(3-Amino-propyl)-N-[1-(1-benzyl-4-methyl-6-oxo-5-phenyl-1,6-dihydro-pyrimidin-2-yl)-2-methyl-propyl]-4-methyl-benzamide;

N-(3-Amino-propyl)-N-[1-(1-benzyl-4,5-dimethyl-6-oxo-1,6-dihydro-pyrimidin-2-yl)-2-methyl-propyl]-4-methyl-benzamide;

N-(3-Amino-propyl)-N-[1-(1-benzyl-4-methyl-6-oxo-5-phenyl-1,6-dihydro-pyrimidin-2-yl)-2-methyl-propyl]-4-methyl-benzamide;

N-(3-Amino-propyl)-N-{1-[1-benzyl-5-(3-fluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3-chloro-phenyl)-4-methyl-6-oxo-1,6-dihydro-pyrimidin-2-yl]-2-methyl-propyl}-4-methyl-benzamide;

N-(3-Amino-propyl)-N-[1-(1-benzyl-4-methyl-6-oxo-5-m-tolyl-1,6-dihydro-pyrimidin-2-yl)-2-methyl-propyl]-4-methyl-benzamide;

N-(3-Amino-propyl)-N-{1-[1-benzyl-5-(3-methoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-4-methyl-6-oxo-5-(3-trifluoromethyl-phenyl)-1,6-dihydro-pyrimidin-2-yl]-2-methyl-propyl}-4-methyl-benzamide;

N-(3-Amino-propyl)-N-{1-[1-benzyl-5-(4-fluoro-phenyl)-4-methyl-6-oxo-1,6-dihydro-pyrimidin-2-yl]-2-methyl-propyl}-4-methyl-benzamide;

N-(3-Amino-propyl)-N-[1-(1-benzyl-4-methyl-6-oxo-5-p-tolyl-1,6-dihydro-pyrimidin-2-yl)-2-methyl-propyl]-4-methyl-benzamide;

N-(3-Amino-propyl)-N-{1-[1-benzyl-5-(4-chloro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(4-methoxy-phenyl)-4-methyl-6-oxo-1,6-dihydro-pyrimidin-2-yl]-2-methyl-propyl}-4-methyl-benzamide;

N-(3-Amino-propyl)-N-[1-(1-benzyl-5-furan-2-yl-4-methyl-6-oxo-1,6-dihydro-pyrimidin-2-yl)-2-methyl-propyl]-4-methyl-benzamide;

N-(3-Amino-propyl)-N-[1-(1-benzyl-5-furan-3-yl-4-methyl-6-oxo-1,6-dihydro-pyrimidin-2-yl)-2-methyl-propyl]-4-methyl-benzamide N-(3-Amino-propyl)-N-[1-(1-benzyl-4-methyl-6-oxo-5-thien-3-yl-1,6-dihydro-pyrimidin-2-yl)-2-methyl-propyl]-4-methyl-benzamide;

N-(3-Amino-propyl)-N-{1-[1-benzyl-4-methyl-5-(4-methylsulfanyl-phenyl)-6-oxo-1,6-dihydro-pyrimidin-2-yl]-2-methyl-propyl}-4-methyl-benzamide;

N-(3-Amino-propyl)-N-{1-[1-benzyl-5-(4-cyano-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(4-ethoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3-ethoxy-phenyl)-4-methyl-6-oxo-1,6-dihydro-pyrimidin-2-yl]-2-methyl-propyl}-4-methyl-benzamide;

N-{1-[5-(3-Amino-phenyl)-1-benzyl-4-methyl-6-oxo-1,6-dihydro-pyrimidin-2-yl]-2-methyl-propyl}-N-(3-amino-propyl)-4-methyl-benzamide;

N-(3-Amino-propyl)-N-[1-(1-benzyl-4-methyl-6-oxo-5-o-tolyl-1,6-dihydro-pyrimidin-2-yl)-2-methyl-propyl]-4-methyl-benzamide;

N-{1-[5-(3-Acetylamino-phenyl)-1-benzyl-4-methyl-6-oxo-1,6-dihydro-pyrimidin-2-yl]-2-methyl-propyl}-N-(3-amino-propyl)-4-methyl-benzamide;

N-(3-Amino-propyl)-N-{1-[1-benzyl-5-(3-cyano-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3-dimethylamino-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2-methoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2-ethoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2-fluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3,4-difluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2,3-difluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2,4-difluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2,5-difluoro-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(2,5-dimethyl-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3,4-dimethyl-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3,4-dimethoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(4-fluoro-3-methyl-phenyl)-4-methyl-6-oxo-1,6-dihydro-pyrimidin-2-yl]-2-methyl-propyl}-4-methyl-benzamide;

N-{1-[5-(3-Amino-4-methyl-phenyl)-1-benzyl-4-methyl-6-oxo-1,6-dihydro-pyrimidin-2-yl]-2-methyl-propyl}-N-(3-amino-propyl)-4-methyl-benzamide;

N-(3-Amino-propyl)-N-{1-[1-benzyl-5-(4-hydroxymethyl-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(3-methoxy-phenyl)-4-methyl-6-oxo-1,6-dihydro-pyrimidin-2-yl]-2-methyl-propyl}-4-methyl-benzamide;

N-(3-Amino-propyl)-N-{1-[1-benzyl-5-(piperonyl)-4-methyl-6-oxo-1,6-dihydro-pyrimidin-2-yl]-2-methyl-propyl}-4-methyl-benzamide;

N-(3-Amino-propyl)-N-[1-(1-benzyl-4-methyl-5-naphthalen-1-ylmethyl-6-oxo-1,6-dihydro-pyrimidin-2-yl)-2-methyl-propyl]-4-methyl-benzamide;

N-(3-Amino-propyl)-N-[1-(1-benzyl-4-cyano-5-methyl-6-oxo-1,6-dihydro-pyrimidin-2-yl)-2-methyl-propyl]-3-fluoro-4-methyl-benzamide;

N-(3-Amino-propyl)-N-[1-(1-benzyl-4-cyano-5-methyl-6-oxo-1,6-dihydro-pyrimidin-2-yl)-2-methyl-propyl]-4-fluoro-benzamide;

N-(3-Amino-propyl)-N-[1-(1-benzyl-4-cyano-5-methyl-6-oxo-1,6-dihydro-pyrimidin-2-yl)-2-methyl-propyl]-4-ethyl-benzamide;

N-(3-Amino-propyl)-N-[1-(1-benzyl-4-cyano-5-methyl-6-oxo-1,6-dihydro-pyrimidin-2-yl)-2-methyl-propyl]-4-trifluoromethyl-benzamide;

N-(3-Amino-propyl)-N-[1-(1-benzyl-4-cyano-5-methyl-6-oxo-1,6-dihydro-pyrimidin-2-yl)-2-methyl-propyl]-4-trifluoromethoxy-benzamide;

N-(3-Amino-propyl)-N-[1-(1-benzyl-4-cyano-5-methyl-6-oxo-1,6-dihydro-pyrimidin-2-yl)-2-methyl-propyl]-3-fluoro-benzamide;

N-(3-Amino-propyl)-N-[1-(1-benzyl-4-cyano-5-methyl-6-oxo-1,6-dihydro-pyrimidin-2-yl)-2-methyl-propyl]-3-chloro-benzamide;

N-(3-Amino-propyl)-N-[1-(1-benzyl-4-cyano-5-methyl-6-oxo-1,6-dihydro-pyrimidin-2-yl)-2-methyl-propyl]-3-cyano-benzamide;

N-(3-Amino-propyl)-N-[1-(1-benzyl-4-cyano-5-methyl-6-oxo-1,6-dihydro-pyrimidin-2-yl)-2-methyl-propyl]-3-fluoro-4-trifluoromethyl-benzamide;

N-(3-Amino-propyl)-N-[1-(1-benzyl-4-cyano-5-methyl-6-oxo-1,6-dihydro-pyrimidin-2-yl)-2-methyl-propyl]-3,4-difluoro-benzamide;

N-(3-Amino-propyl)-N-[1-(1-benzyl-4-cyano-5-methyl-6-oxo-1,6-dihydro-pyrimidin-2-yl)-2-methyl-propyl]-3,4-dimethoxy-benzamide;

N-(3-Amino-propyl)-N-[1-(1-benzyl-4-methyl-6-oxo-1,6-dihydro-pyrimidin-2-yl)-2-methyl-propyl]-4-methyl-benzamide;

N-(3-Amino-propyl)-N-[1-(1-benzyl-6-oxo-4-phenyl-1,6-dihydro-pyrimidin-2-yl)-2-methyl-propyl]-4-methyl-benzamide;

N-(3-Amino-propyl)-N-[1-(1-benzyl-6-oxo-4-propyl-1,6-dihydro-pyrimidin-2-yl)-2-methyl-propyl]-4-methyl-benzamide;

N-(3-Amino-propyl)-N-[1-(1-benzyl-4-isopropyl-6-oxo-1,6-dihydro-pyrimidin-2-yl)-2-methyl-propyl]-4-methyl-benzamide;

N-(3-Amino-propyl)-N-[1-(1-benzyl-4-methoxymethyl-6-oxo-1,6-dihydro-pyrimidin-2-yl)-2-methyl-propyl]-4-methyl-benzamide;

N-(3-Amino-propyl)-N-[1-(1-benzyl-4-hydroxymethyl-6-oxo-1,6-dihydro-pyrimidin-2-yl)-2-methyl-propyl]-4-methyl-benzamide;

N-(3-Amino-propyl)-N-[1-(1-benzyl-6-oxo-4-trifluoromethyl-1,6-dihydro-pyrimidin-2-yl)-2-methyl-propyl]-4-methyl-benzamide;

N-(3-Amino-propyl)-N-[1-(1-benzyl-4,5-dimethyl-6-oxo-1,6-dihydro-pyrimidin-2-yl)-2-methyl-propyl]-4-methyl-benzamide;

N-(3-Amino-propyl)-N-[1-(1-benzyl-4-methoxy-6-oxo-1,6-dihydro-pyrimidin-2-yl)-2-methyl-propyl]-4-methyl-benzamide;

2-{1-[(3-Amino-propyl)-(4-methyl-benzoyl)-amino]-2-methyl-propyl}-1-benzyl-5-methyl-6-oxo-1,6-dihydro-pyrimidine-4-carboxylic acid ethyl ester;

2-{1-[(3-Amino-propyl)-(4-methyl-benzoyl)-amino]-2-methyl-propyl}-1-benzyl-5-methyl-6-oxo-1,6-dihydro-pyrimidine-4-carboxylic acid amide;

N-[1-(4-Acetylamino-1-benzyl-6-oxo-1,6-dihydro-pyrimidin-2-yl)-2-methyl-propyl]-N-(3-amino-propyl)-4-methyl-benzamide;

N-(3-Amino-propyl)-N-[1-(1-benzyl-4-cyano-5-methyl-6-oxo-1,6-dihydro-pyrimidin-2-yl)-2-methyl-propyl]-4-methyl-benzamide;

N-(3-Amino-propyl)-N-[1-(1-benzyl-5-methyl-6-oxo-1,6-dihydro-pyrimidin-2-yl)-2-methyl-propyl]-4-methyl-benzamide;

N-(3-Amino-propyl)-N-[1-(1-benzyl-6-oxo-1,6-dihydro-pyrimidin-2-yl)-2-methyl-propyl]-4-methyl-benzamide;

N-(3-Amino-propyl)-N-[1-(1-benzyl-5-isopropyl-4-methyl-6-oxo-1,6-dihydro-pyrimidin-2-yl)-2-methyl-propyl]-4-methyl-benzamide;

N-(3-Amino-propyl)-N-[1-(1-benzyl-5-fluoro-4-methyl-6-oxo-1,6-dihydro-pyrimidin-2-yl)-2-methyl-propyl]-4-methyl-benzamide;

N-(3-Amino-propyl)-N-[1-(1-benzyl-5-bromo-4-methyl-6-oxo-1,6-dihydro-pyrimidin-2-yl)-2-methyl-propyl]-4-methyl-benzamide;

N-(3-Amino-propyl)-N-[1-(1,5-dibenzyl-4-methyl-6-oxo-1,6-dihydro-pyrimidin-2-yl)-2-methyl-propyl]-4-methyl-benzamide;

N-(3-Amino-propyl)-N-[1-(1-benzyl-4-methyl-6-oxo-5-phenyl-1,6-dihydro-pyrimidin-2-yl)-2-methyl-propyl]-4-methyl-benzamide;

2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid ethyl ester;

N-(3-Amino-propyl)-N-[1-(1-benzyl-4,5-dimethyl-6-oxo-1,6-dihydro-pyrimidin-2-yl)-2-methyl-propyl]-3-fluoro-4-methyl-benzamide;

N-(3-Amino-propyl)-N-[1-(1-benzyl-4,5-dimethyl-6-oxo-1,6-dihydro-pyrimidin-2-yl)-2-methyl-propyl]-4-methoxy-benzamide;

Benzo[1,2,3]thiadiazole-5-carboxylic acid(3-amino-propyl)-[1-(1-benzyl-4,5-dimethyl-6-oxo-1,6-dihydro-pyrimidin-2-yl)-2-methyl-propyl]-amide;

N-(3-Amino-propyl)-N-[1-(1-benzyl-4,5-dimethyl-6-oxo-1,6-dihydro-pyrimidin-2-yl)-2-methyl-propyl]-4-cyano-benzamide;

Benzo[1,3]dioxole-5-carboxylic acid(3-amino-propyl)-[1-(1-benzyl-4,5-dimethyl-6-oxo-1,6-dihydro-pyrimidin-2-yl)-2-methyl-propyl]-amide;

N-(2-Amino-ethyl)-N-[1-(1-benzyl-4,5-dimethyl-6-oxo-1,6-dihydro-pyrimidin-2-yl)-2-methyl-propyl]-benzamide;

N-(3-Amino-propyl)-N-[1-(1-benzyl-4-cyano-5-methyl-6-oxo-1,6-dihydro-pyrimidin-2-yl)-2-methyl-propyl]-4-methyl-benzamide;

N-(3-Amino-propyl)-N-[1-(1-benzyl-4,5-dimethyl-6-oxo-1,6-dihydro-pyrimidin-2-yl)-2-methyl-propyl]-3-fluoro-4-methyl-benzamide;

N-(2-Amino-ethyl)-N-[1-(1-benzyl-4,5-dimethyl-6-oxo-1,6-dihydro-pyrimidin-2-yl)-2-methyl-propyl]-4-cyano-benzamide;

5-Methyl-thiophene-2-carboxylic acid(2-amino-ethyl)-[1-(1-benzyl-4,5-dimethyl-6-oxo-1,6-dihydro-pyrimidin-2-yl)-2-methyl-propyl]-amide 5-Methyl-isoxazole-3-carboxylic acid(3-amino-propyl)-[1-(1-benzyl-4,5-dimethyl-6-oxo-1,6-dihydro-pyrimidin-2-yl)-2-methyl-propyl]-amide;

5-Methyl-pyrazine-2-carboxylic acid(3-amino-propyl)-[1-(1-benzyl-4,5-dimethyl-6-oxo-1,6-dihydro-pyrimidin-2-yl)-2-methyl-propyl]-amide;

N-(3-Amino-propyl)-N-[1-(1-benzyl-4,5-dimethyl-6-oxo-1,6-dihydro-pyrimidin-2-yl)-2-methyl-propyl]-2-methoxy-acetamide;

N-(3-Amino-propyl)-N-[1-(4,5-dimethyl-1-naphthalen-1-ylmethyl-6-oxo-1,6-dihydro-pyrimidin-2-yl)-2-methyl-propyl]-2-methoxy-acetamide;

2-{1-[4-(2-Amino-ethyl)-2-p-tolyl-imidazol-1-yl]-2-methyl-propyl}-3-benzyl-5,6-dimethyl-3H-pyrimidin-4-one;

3-Benzyl-5,6-dimethyl-2-[2-methyl-1-(2-p-tolyl-4,5-dihydro-imidazol-1-yl)-propyl]-3H-pyrimidin-4-one;

3-Benzyl-5,6-dimethyl-2-{2-methyl-1-[2-(5-methyl-thiophen-2-yl)-4,5-dihydro-imidazol-1-yl]-propyl}-3H-pyrimidin-4-one;

N-(3-Amino-propyl)-N-[1-(1-benzyl-4,5-dimethyl-6-oxo-1,6-dihydro-pyrimidin-2-yl)-2-methyl-propyl]-4-methyl-benzenesulfonamide;

N-(3-Amino-propyl)-N-[1-(3-benzyl-4-oxo-3,4,5,6,7,8-hexahydro-quinazolin-2-yl)-2-methyl-propyl]-4-methyl-benzamide;

N-(3-Amino-propyl)-N-[1-(3-benzyl-4-oxo-4,5,6,7-tetrahydro-3H-cyclopentapyrimidin-2-yl)-2-methyl-propyl]-4-methyl-benzamide; and 2-(1-Amino-2-methyl-propyl)-3-benzyl-3,5,6,7-tetrahydro-cyclopentapyrimidin-4-one.

Utility, Testing and Administration

General Utility

Once made, the compounds of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a particular embodiment, the compounds of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to, and/or inhibit the activity of, a mitotic kinesin, KSP. In one embodiment, the KSP is human KSP, although the compounds may be used to bind to or inhibit the activity of KSP kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. No. 6,437,115, hereby incorporated by reference in its entirety. The compounds of the invention have been shown to have specificity for KSP. However, the present invention includes the use of the compounds to bind to or modulate other mitotic kinesins.

The compounds of the invention are used to treat cellular proliferation diseases. Such disease states which can be treated by the compounds, compositions and methods provided herein include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in one embodiment, the invention herein includes application to cells or individuals afflicted or subject to impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non- Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Testing

For assay of KSP-modulating activity, generally either KSP or a compound according to the invention is non-diffusably bound to an insoluble support having isolated sample receiving areas (e.g., a microtiter plate, an array, etc.). The insoluble support may be made of any composition to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the sample is not crucial so long as it is compatible with the reagents and overall methods of the invention, maintains the activity of the sample and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The compounds of the invention may be used on their own to inhibit the activity of a mitotic kinesin, particularly KSP. In one embodiment, a compound of the invention is combined with KSP and the activity of KSP is assayed. Kinesin (including KSP) activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, Anal. Biochem. 242 (1):20-5; Gittes et al., 1996, Biophys. J. 70(1): 418-29; Shirakawa et al., 1995, J. Exp. Biol. 198: 1809-15; Winkelmann et al., 1995, Biophys. J. 68: 2444-53; Winkelmann et al., 1995, Biophys. J. 68: 72S.)

Methods known in the art for determining ATPase hydrolysis activity also can be used. Suitably, solution based assays are utilized. U.S. Pat. No. 6,410,254, hereby incorporated by reference in its entirety, describes such assays. Alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of the reaction mixture is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In one embodiment ATPase assays of kinesin are performed in the absence of microtubules. In another embodiment, the ATPase assays are performed in the presence of microtubules. Different types of agents can be detected in the above assays. In a one embodiment, the effect of an agent is independent of the concentration of microtubules and ATP. In another embodiment, the effect of the agents on kinesin ATPase can be decreased by increasing the concentrations of ATP, microtubules or both. In yet another embodiment, the effect of the agent is increased by increasing concentrations of ATP, microtubules or both.

Compounds that inhibit the biochemical activity of KSP in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414), each incorporated herein by reference in its entirety.

The compounds of the invention inhibit the KSP kinesin. One measure of inhibition is $IC_{50}$, defined as the concentration of the compound at which the activity of KSP is decreased by fifty percent relative to a control. Preferred compounds have $IC_{50}$'s of less than about 1 mM, with preferred embodiments having $IC_{50}$'s of less than about 100 µM, with more preferred embodiments having $IC_{50}$'s of less than about 10 µM, with particularly preferred embodiments having $IC_{50}$'s of less than about 1 µM, and especially preferred embodiments having $IC_{50}$'s of less than about 100 nM, and with the most preferred embodiments having $IC_{50}$'s of less than about 10 nM. Measurement of $IC_{50}$ is done using an ATPase assay such as described herein.

Another measure of inhibition is $K_i$. For compounds with $IC_{50}$'s less than 1 µM, the $K_i$ or $K_d$ is defined as the dissociation rate constant for the interaction of the compounds described herein with KSP. Preferred compounds have $K_i$'s of less than about 100 µM, with preferred embodiments having $K_i$'s of less than about 10 µM, and particularly preferred embodiments having $K_i$'s of less than about 1 µM and especially preferred embodiments having $K_i$'s of less than about 100 nM, and with the most preferred embodiments having $K_i$'s of less than about 10 nM.

The $K_i$ for a compound is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM; those having a $GI_{50}$ of less than about 20 µM are more preferred; those having a $GI_{50}$ of less than about 10 µM more so; those having a $GI_{50}$ of less than about 1 µM more so; those having a $GI_{50}$ of less than about 100 nM more so; and those having a $GI_{50}$ of less than about 10 nM even more so. Measurement of $GI_{50}$ is done using a cell proliferation assay such as described herein. Compounds of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation, irrespective of the concentration demonstrating inhibition, have potential clinical usefulness.

To employ the compounds of the invention in a method of screening for compounds that bind to KSP kinesin, the KSP is bound to a support, and a compound of the invention is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the compound of the invention to KSP may be done in a number of ways. In one embodiment, the compound is labeled, for example, with a fluorescent or radioactive moiety, and binding is determined directly. For example, this may be done by attaching all or a portion of KSP to a solid support, adding a labeled test compound (for example a compound of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}I$, or with fluorophores. Alternatively, more than one component may be labeled with different labels; using $^{125}I$ for the proteins, for example, and a fluorophor for the antimitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that particular protein, for example, polymer structures such as microtubules, and energy sources such as ATP. Particular embodiments of assays herein include candidate agents which do not bind the cellular proliferation protein in its endogenous native state termed herein as "exogenous" agents. In another embodiment, exogenous agents further exclude antibodies to KSP.

Candidate agents can encompass numerous chemical classes, though typically they are organic molecules, preferably they are small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl-, hydroxyl-, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, and/or amidification to produce structural analogs.

Competitive screening assays may be done by combining KSP and a drug candidate in a first sample. A second sample comprises a compound of the present invention, KSP and a drug candidate. This may be performed in either the presence or absence of microtubules. The binding of the drug candidate is determined for both samples, and a change, or difference in binding between the two samples indicates the presence of a drug candidate capable of binding to KSP and potentially inhibiting its activity. That is, if the binding of the drug candidate is different in the second sample relative to the first sample, the drug candidate is capable of binding to KSP.

In a particular embodiment, the binding of the candidate agent to KSP is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In another embodiment, the competitor is added first, followed by the candidate agent. Displacement of the competitor is an indication the candidate agent is binding to KSP and thus is capable of binding to, and potentially inhibiting, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

Inhibition is tested by screening for candidate agents capable of inhibiting the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Suitably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Administration

Accordingly, the compounds of the invention are administered to cells. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Compounds of the invention having the desired pharmacological activity may be administered, preferably as a pharmaceutically acceptable composition comprising an pharmaceutical excipient, to a patient, as described herein. Depending upon the manner of introduction, the compounds may be formulated in a variety of ways as discussed below. The concentration of therapeutically active compound in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of a compound of the present invention. In one aspect of the invention, a compound of the present invention is co-administered with one or more other chemotherapeutic agents. By "co-administer" it is meant that the present compounds are administered to a patient such that the present compounds as well as the co-administered compound may be found in the patient's bloodstream at the same time, regardless when the compounds are actually administered, including simultaneously.

The administration of the compounds and compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include a compound of formula I or a pharmaceutically acceptable salt, solvate, or solvate of a salt thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Fluids used commonly for intravenous (IV) use are disclosed in Remington, the Science and Practice of Pharmacy [full citation previously provided], and include:
  alcohol (e.g., in dextrose and water ("D/W") [e.g., 5% dextrose] or dextrose and water [e.g., 5% dextrose] in normal saline solution ("NSS"); e.g. 5% alcohol);
  synthetic amino acid such as Aminosyn, FreAmine, Travasol, e.g., 3.5 or 7; 8.5; 3.5, 5.5 or 8.5% respectively;
  ammonium chloride e.g., 2.14%;
  dextran 40, in NSS e.g., 10% or in D5/W e.g., 10%;
  dextran 70, in NSS e.g., 6% or in D5/W e.g., 6%;
  dextrose (glucose, D5/W) e.g., 2.5-50%;
  dextrose and sodium chloride e.g., 5-20% dextrose and 0.22-0.9% NaCl;
  lactated Ringer's (Hartmann's) e.g., NaCl 0.6%, KCl 0.03%, $CaCl_2$ 0.02%;
  lactate 0.3%;
  mannitol e.g., 5%, optionally in combination with dextrose e.g., 10% or NaCl e.g., 15 or 20%;
  multiple electrolyte solutions with varying combinations of electrolytes, dextrose, fructose, invert sugar Ringer's e.g., NaCl 0.86%, KCl 0.03%, $CaCl_2$ 0.033%;
  sodium bicarbonate e.g., 5%;
  sodium chloride e.g., 0.45, 0.9, 3, or 5%;
  sodium lactate e.g., ⅙ M; and
  sterile water for injection The pH of such fluids may vary, and will typically be from 3.5 to 8 such as known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All publications, including but not limited to patents and patent applications, cited in this specification are herein incorporated by reference as if each individual publication were specifically and individually indicated to be incorporated by reference herein as though fully set forth.

EXAMPLES

All anhydrous solvents were purchased from Aldrich Chemical Company in SureSeal® containers.

Example 1

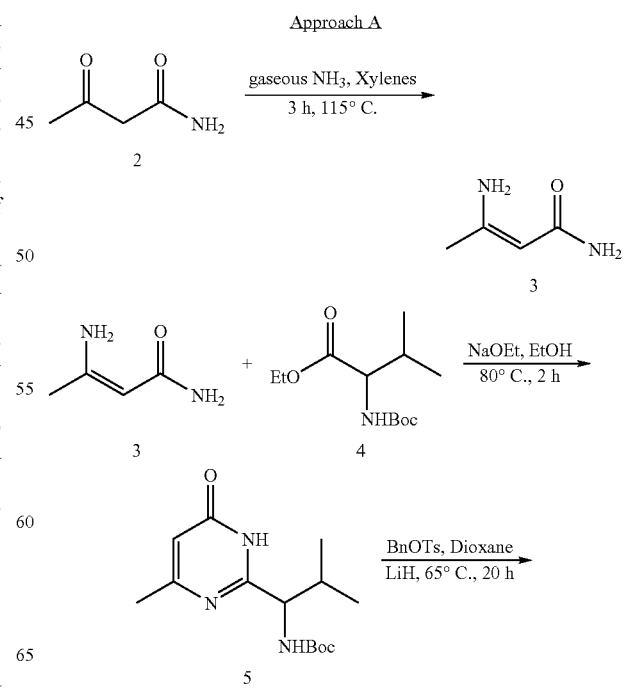

-continued

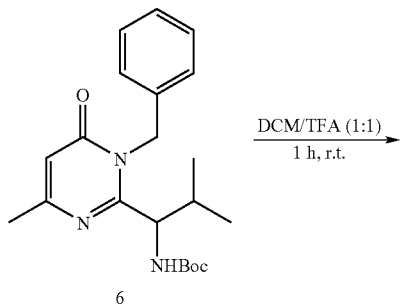
6

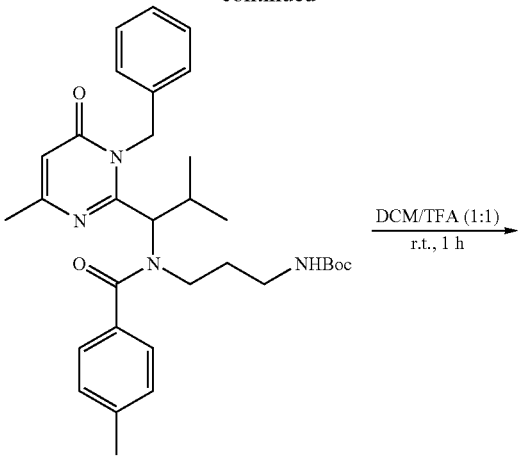
10

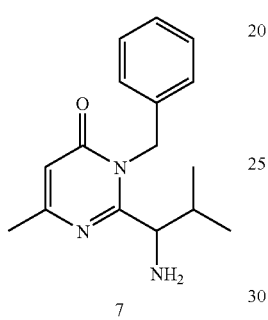
7

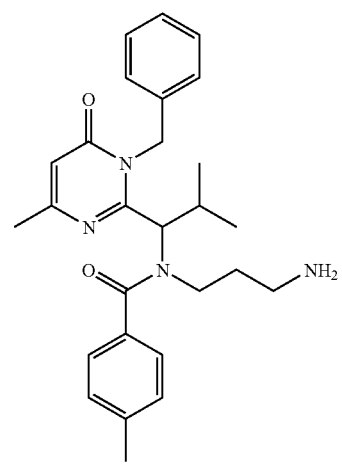
1

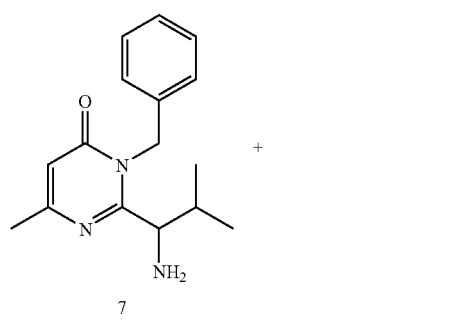
7 + 8

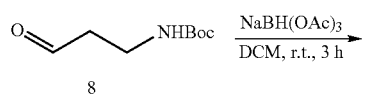

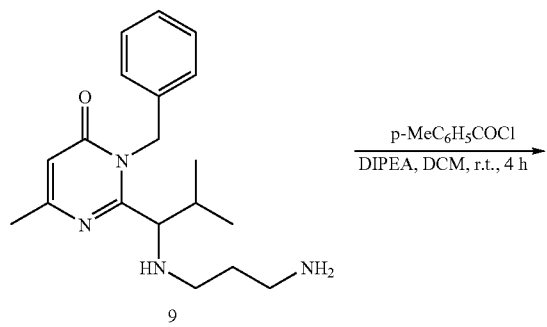
9

Acetoacetamide 2 (12.0 g, 0.119 mol) and xylenes (200 mL) were added to a 3-necked 500 mL round bottom flask equipped with a dry-ice reflux condenser. The resulting mixture was heated to 115° C. and purged continuously with gaseous ammonia for 3 hours, and then cooled to room temperature. The reaction mixture was filtered and the filtrate was concentrated under reduced pressure. The remaining white solid was determined from $^1$H NMR analysis to be the pure desired product 3 (1.491 g, 14.9 mmol). To the remaining solid residue obtained from filtration was added 200 mL of distilled water. The aqueous solution was extracted with ethyl acetate (3×100 mL) and hot chloroform (3×100 mL). The combined organic layers were dried over sodium sulfate and concentrated under reduced pressure to yield additional desired product 3 (3.628 g, 36.2 mmol). The overall yield for the reaction was 47.4%.

Sodium ethoxide was freshly generated by addition of sodium metal (1.0 g) to anhydrous ethanol (50 mL) carefully at room temperature. To a mixture of β-aminocrotonamide 3 (1.389 g, 13.87 mmol) and ester 4 (3.744 g, 15.26 mmol) in a 250 mL flask was added the sodium ethoxide solution in anhydrous ethanol (50 mL) at room temperature. The resulting solution was heated to 80° C. and stirred under an atmosphere of nitrogen for 2 hours. Then the mixture was cooled to room temperature and concentrated in vacuo. The remaining residue was combined with 50 mL of distilled water and neutralized with 1 M aqueous HCl solution. It was then extracted with ethyl acetate (3×40 mL) and hot chloroform (3×40 mL). The combined organic layers were dried over sodium sulfate and concentrated under reduced pressure, and the yellow residue was purified via flash column chromatography using a mixture of ethyl acetate and hexane as eluent. The desired product 5 (1.261 g, 32.3%) was characterized by $^1$H-NMR and LC/MS (LRMS (MH) m/z 282.2).

To a solution of pyrimidinone 5 (506 mg, 1.80 mmol) in dioxane (30 mL) was added lithium hydride (17 mg, 2.16 mmol) at room temperature. The resulting suspension was stirred for 15 minutes at room temperature, followed by addition of benzyl tosylate (519 mg, 1.98 mmol). The reaction mixture was stirred under nitrogen at 65° C. for 20 hours. The dioxane was removed in vacuo, and the residue was diluted with ethyl acetate (50 mL) and distilled water (50 mL). The organic layer was separated and the aqueous phase was extracted with additional ethyl acetate (3×25 mL). The combined organic layers were washed with brine and dried over sodium sulfate. After evaporation of solvents, the residual amorphous solid was purified via flash column chromatography using a mixture of ethyl acetate and hexane as eluent. The pure desired product 6 (388 mg, 58.1%) was isolated as a white solid, which was fully characterized using $^1$H-NMR and LC/MS (LRMS (MH) m/z 372.2).

To a solution of pyrimidinone 6 (388 mg 1.04 mmol) in dichloromethane (15 mL) was added trifluoroacetic acid (15 mL) at 0° C. The resulting solution was stirred at room temperature for one hour and then concentrated in vacuo. The residue was dissolved in ethyl acetate (25 mL) and neutralized with saturated aqueous sodium bicarbonate (25 mL). The organic layer was separated and the aqueous phase was extracted with ethyl acetate (3×25 mL). The combined organic layers were dried over sodium sulfate and concentrated to provide the desired product 7 (245 mg, 88.0%) as an oil, which was characterized by LC/MS analysis (LRMS (MH) m/z 272.2) and used in the next step without further purification.

To a solution of pyrmidinone 7 (245 mg, 0.903 mmol) in dichloromethane (20 mL) at room temperature were added aldehyde 8 (188 mg, 1.084 mmol) and sodium triacetoxyborohydride (230 mg, 1.084 mmol), successively. The resulting mixture was stirred under nitrogen for 3 hours, followed by addition of water (40 mL). The organic layer was separated, and the aqueous phase was extracted with dichloromethane (3×40 mL). The combined organic layers were washed with brine and dried over sodium sulfate. After evaporation of the solvents, the residue was purified via flash column chromatography using a mixture of ethyl acetate and hexane as eluent providing the desired product 9 (250 mg, 64.5%) as a white solid, which was fully characterized using $^1$H NMR and LC/MS (LRMS (MH) m/z 429.6).

To a solution of pyrimidinone 9 (250 mg, 0.583 mmol) and diisopropylethylamine (90 mg, 0.700 mmol) in dichloromethane (20 mL) at 0° C. was added p-toluoyl chloride (108 mg, 0.700 mmol). The resulting solution was stirred under nitrogen at room temperature for 4 hours, and quenched with saturated aqueous sodium bicarbonate (20 mL). The organic layer was separated and the aqueous phase was extracted with dichloromethane (3×25 mL). The organic combined layers were washed with brine and dried over sodium sulfate. After evaporation of solvents, the residue was purified via flash column chromatography using a mixture of ethyl acetate and hexane as eluent, the pure product 10 (191 mg, 60.0%) was isolated as an amorphous solid, which was characterized using $^1$H-NMR and LC/MS (LRMS (MH) m/z 547.7).

To a solution of pyrimidinone 10 (67 mg, 0.12 mmol) in dichloromethane (10 mL) was added trifluoroacetic acid (10 mL) at room temperature. The resulting solution was stirred at room temperature for one hour and then concentrated under reduced pressure. The residue was dried under high vacuum and dissolved in ethyl acetate (25 mL). It was neutralized with saturated aqueous sodium bicarbonate solution (25 mL), and the aqueous phase was extracted with ethyl acetate (3×25 mL). The combined organic layers were dried over sodium sulfate. After evaporation of solvents, the residue was purified via flash column chromatography (NH$_4$OH/MeOH/DCM 0.1:1:10 as eluent). The desired product 1 (52 mg, 90.0%) was isolated as a glassy solid, which was fully characterized with $^1$H-NMR and LC/MS analysis (LRMS (MH) m/z 447.3).

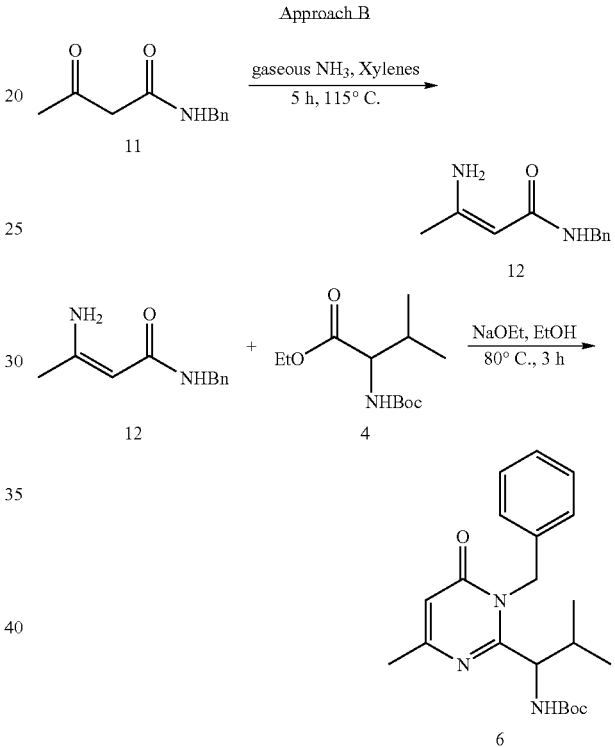

To a 3-necked 500 mL round bottom flask equipped with a dry-ice reflux condenser were added β-ketoamide 11 (13.0 g, 68.0 mmol) and xylenes (200 mL). The mixture was heated to 115° C., purged continuously with gaseous ammonia for 5 hours, and then it was cooled to room temperature. The resulting mixture was concentrated and the remaining off-white residue was dried under high vacuum for 12 hours. $^1$H-NMR indicated the residue contained 88% of the desired product 12 (11.4 g). The crude product was used in the next step without further purification.

Sodium ethoxide was freshly generated by addition of sodium metal (1.0 g) to anhydrous ethanol (50 mL) carefully at room temperature. To this mixture of β-aminoamide 12 (813 mg, 4.27 mmol) and ester 4 (1.258 g, 5.12 mmol) in a 250 mL flask was added the sodium ethoxide solution in anhydrous ethanol (50 mL) at room temperature. The resulting solution was heated to 80° C. and stirred under an atmosphere of nitrogen for 3 hours. Then the mixture was cooled to room temperature and concentrated in vacuo. The residue was combined with distilled water (50 mL) and neutralized with 1 M aqueous HCl solution, and it was then extracted with ethyl acetate (3×40 mL). The combined organic layers were dried over sodium sulfate and concentrated under reduced pressure, and the yellow residue was purified via flash column chromatography using a mixture of ethyl acetate and hexane as eluent. The desired product 6 (10 mg, 1.0%) was isolated, which was characterized by ¹H-NMR and LC/MS (LRMS (MH) m/z 372.2) and found to be identical to the product obtained from Approach A.

Example 2

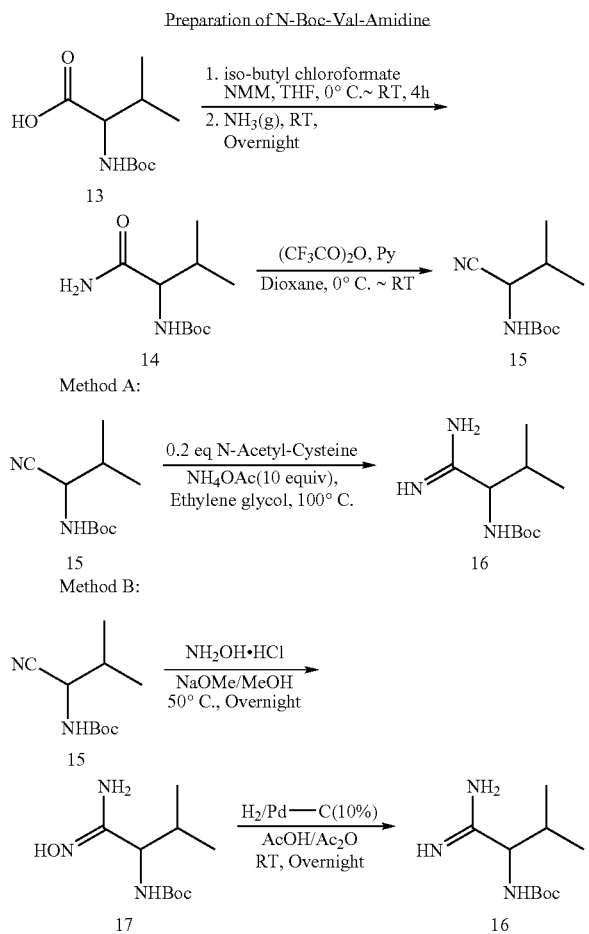

Preparation of N-Boc-Val-Amidine

Method A:

Method B:

To a 0° C. solution of N-Boc-DL-Val-OH (Compound 13, 11.0 g, 50.0 mmol) and N-methyl morpholine (7.5 mL, 70.0 mmol) in anhydrous tetrahydrofuran (300 mL) was added iso-butyl chloroformate (8.5 mL, 66.0 mmol). The resulting mixture was stirred at room temperature for 4 hours. The flask was then equipped with a dry-ice reflux condenser and purged continuously with gaseous ammonia for 2 hours. The resulting reaction mixture was then stirred at room temperature overnight. After most of the solvent was evaporated, the residue was diluted with saturated aqueous sodium bicarbonate and extracted with ethyl acetate. The combined organic layers were dried over sodium sulfate and evaporated. The residue (10.8 g) was confirmed to be the desired amide 14 as judged by ¹H-NMR and LC/MS (LRMS (MH) m/z 216.28). Amide 14 was not purified for the subsequent transformation.

To a room temperature solution of amide 14 (1.2 g, 5.0 mmol) in dioxane (20 mL) were added pyridine (1.0 mL, 12.5 mmol) and trifluoroacetic anhydride (1.41 mL, 10.0 mmol), successively. The resulting solution was stirred for 4 hours until no starting material was present. The reaction was quenched with saturated aqueous sodium bicarbonate solution and extracted with ethyl acetate (3×100 mL). The combined organic layers were dried over sodium sulfate and concentrated in vacuo. The residue was purified by flash chromatography (silica gel, Hexane/ethyl acetate) to provide compound 15 (1.0 g), which was characterized by ¹H-NMR and LC/MS (LRMS (MH) m/z 198.26).

To a room temperature solution of nitrile 15 (14.0 g, 71.0 mmol) and N-acetylcysteine (230 mg, 1.4 mmol) in ethylene glycol (200 mL) was added solid ammonium acetate (17.8 g, 231.0 mmol). The resulting solution was heated to 100° C. for 48 hours. Most of the ethylene glycol was distilled in vacuo. The resulting residue was dissolved in saturated aqueous sodium bicarbonate (100 mL) and extracted with a mixture of diethyl ether and hexane (3×50 mL). The aqueous phase was then saturated with sodium chloride and extracted with tetrahydrofuran (4×100 mL). The combined organic layers were dried over sodium sulfate and concentrate in vacuo, yielding residue 16 (4.5 g) which was determined to be pure enough for use in subsequent transformations (¹H-NMR and LC/MS (LRMS (MH) m/z 217.20)).

Nitrile 15 (1.0 g, 5.0 mmol) was loaded into a 100 mL flask. A solution of sodium methoxide in methanol (20.0 mL, 10.0 mmol., 0.5 M) was then added to the flask. To the resulting reaction mixture was added hydroxylamine hydrochloride (690 mg, 10.0 mmol). The reaction mixture was then heated to 50° C. overnight. The solvent was then evaporated in vacuo, and the residue was dissolved in saturated sodium chloride solution and extracted with tetrahydrofuran (3×50 mL). The combined organic layers were dried over sodium sulfate and concentrated in vacuo. Compound 17 (960 mg) was determined to be pure enough for subsequent transformations without further purification (LC/MS (LRMS (MH) m/z 232.29)).

To a room temperature solution of intermediate 17 (462 mg, 2.0 mmol) in acetic acid (5.0 mL) were added acetic anhydride (300 uL, 3.0 mmol) and Pd/C (10% wt, 65 mg). The reaction mixture was stirred under a hydrogen atmosphere for 24 hours and then filtered through Celite. The Celite plug was washed with additional methanol. After evaporation of the solvents, the residue was dissolved in saturated aqueous sodium bicarbonate solution (20 mL) and extracted with a mixture of diethyl ether/hexane (3×10 mL). The aqueous phase was then saturated with sodium chloride and extracted with tetrahydrofuran (4×50 mL). The combined tetrahydrofuran layers were dried over sodium sulfate and concentrated in vacuo. Amidine 16 (315 mg) was determined to be pure enough for the next transformation (¹H-NMR and LC/MS (LRMS (MH) m/Z 217.20)).

Example 3

Preparation of Pyrimidinone Cores from N-Boc-Val-Amidine (4)

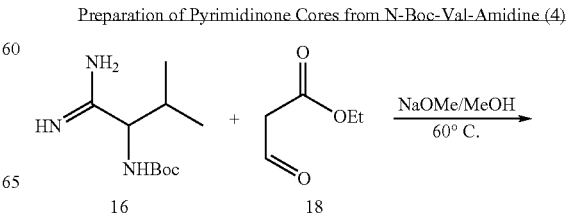

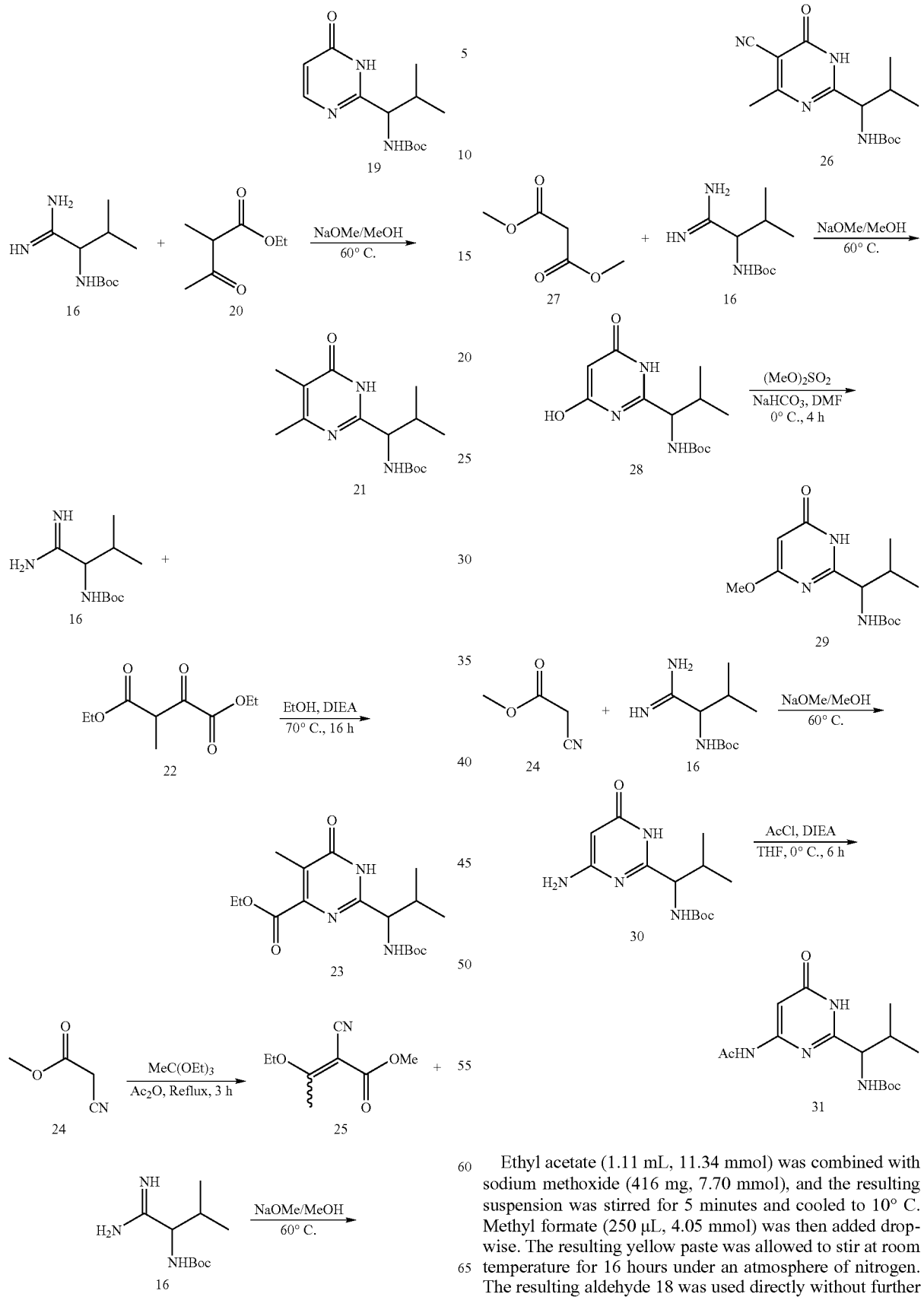
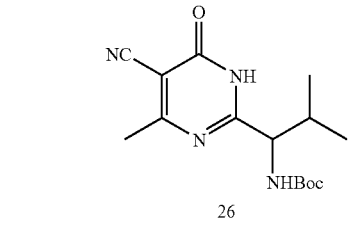

Ethyl acetate (1.11 mL, 11.34 mmol) was combined with sodium methoxide (416 mg, 7.70 mmol), and the resulting suspension was stirred for 5 minutes and cooled to 10° C. Methyl formate (250 µL, 4.05 mmol) was then added drop-wise. The resulting yellow paste was allowed to stir at room temperature for 16 hours under an atmosphere of nitrogen. The resulting aldehyde 18 was used directly without further purification in the next step.

To a solution of aldehyde 18 (523 mg, 4.05 mmol) and unpurified amidine 16 (872 mg, 4.05 mmol) was added a solution of sodium methoxide in methanol (20 mL, 10.00 mmol, 0.5 M). The resulting solution was heated to 60° C. for 30 minutes. Most of the methanol was removed in vacuo, and the residue was diluted with ethyl acetate (20 mL) and distilled water (20 mL). The layers were separated, and the aqueous phase was extracted with ethyl acetate (3×20 mL). The combined organic layers were washed with brine, dried over sodium sulfate and concentrated in vacuo to provide a brown amorphous solid. Purification by flash chromatography (silica gel, ethyl acetate and hexane) yielded the desired pyrimidinone 19 as a foamy white solid (477 mg), which was characterized by $^1$H-NMR and LC/MS (LRMS (MH) m/z: 267.32).

To a solution of β-ketoester 20 (238 mg, 1.65 mmol) and crude amidine 16 (355 mg, 1.65 mmol) in methanol was added a solution of sodium methoxide in methanol (10 mL, 5.00 mmol, 0.5 M). The resulting solution was heated to 60° C. for 30 minutes. Most of the methanol was removed in vacuo, and the residue was diluted with ethyl acetate (20 mL) and distilled water (20 mL). The layers were separated, and the aqueous phase was extracted with ethyl acetate (3×20 mL). The combined organic layers were then washed with brine, dried over sodium sulfate, and concentrated to provide a brown amorphous solid. Purification by flash chromatography (silica gel, ethyl acetate and hexane) yielded the desired pyrimidinone 21 as a foamy white solid (98 mg), which was characterized by $^1$H-NMR and LC/MS (LRMS (MH) m/z: 295.38).

To a room temperature solution of amidine 16 (3.17 g, 14.7 mmol) and diisopropylethylamine (2.56 mL, 14.7 mmol) in anhydrous ethanol (75 mL) was added ester 22 (2.98 g, 14.7 mmol). The resulting mixture was heated to 70° C. for 16 hours. Most of the ethanol was removed in vacuo, and the residue was diluted with ethyl acetate (50 mL) and water (50 mL). The layers were separated, and the aqueous phase was extracted with ethyl acetate (3×50 mL). The combined organic layers were washed with brine and dried over sodium sulfate. After evaporation of the solvents in vacuo, the residual amorphous yellow solid was purified by flash chromatography (silica gel, ethyl acetate and hexane) to yield the desired pyrimidinone 23 (936 mg) as a white solid, which was characterized by $^1$H-NMR and LC/MS (LRMS (MH) m/z: 353.41).

A solution of methyl cyanoacetate 24 (1.673 g, 16.88 mmol) and triethylorthoacetate (3.424 mL, 18.57 mmol) in acetic anhydride (30 mL) was heated to reflux for 3 hours. The resulting solution was cooled to room temperature, and most of acetic anhydride was removed in vacuo. The residue was allowed to stand for three days as crystals formed. Crystalline 25 was isolated by filtration and used directly in the next transformation.

To a solution of ester 25 (51 mg, 0.28 mmol) and amidine 16 (20 mg, 0.90 mmol) in methanol was added a solution of sodium methoxide in methanol (3 mL, 1.5 mmol, 0.5 M). The resulting solution was stirred at 60° C. under an atmosphere of nitrogen for 30 minutes. Most of the methanol was removed under reduced pressure, and the residue was diluted with ethyl acetate (50 mL) and water (50 mL). The layers were separated, and the aqueous phase was extracted with ethyl acetate (3×50 mL). The combined organic layers were washed with brine and dried over sodium sulfate. After evaporation of solvents, the residue was purified by flash chromatography (silica gel, ethyl acetate and hexane) to provide the desired pyrimidinone 26 (27 mg), which was characterized using $^1$H-NMR and LC/MS (LRMS (MH) m/z: 306.36).

To a room temperature solution of diethyl malonate (27, 1.6 mL, 10.0 mmol) and unpurified amidine 16 (2.5 g, 15 mmol) in methanol was added a solution of sodium methoxide in methanol (35.0 mL, 17.5 mmol, 0.5 M in methanol). The resulting solution was heated to 60° C. for 4 hours. The reaction mixture was then allowed to cool to room temperature, and the solvent was removed in vacuo. The resulting residue was dissolved in distilled water (15 mL) and saturated with sodium chloride. The aqueous solution was extracted with tetrahydrofuran (3×100 mL), and the combined organic layers were dried over sodium sulfate. After concentration in vacuo, residue 28 was used in the next step without further purification. Compound 28 was characterized by LC/MS (LRMS (MH) m/z: 283.32).

To a solution of unpurified 28 (2.0 g) in dimethylformamide (100 mL) at 0° C. were added sodium bicarbonate (4.0 g) and dimethyl sulfate (0.8 mL). The resulting solution was stirred at 0° C. for 4 hours until LC/MS analysis indicated that monomethylated 29 was the major product. The reaction was then quenched with water (100 mL), and extracted with dichloromethane (3×60 mL) and ethyl acetate (3×60 mL). The combined organic layers were dried over sodium sulfate. After concentration in vacuo, the residue was purified by flash chromatography (silica gel, dichloromethane/methanol) to provide the desired pyrimidinone 29 (855 mg), which was characterized by $^1$H-NMR and LC/MS (LRMS (MH) m/z: 297.35).

To a room temperature solution of methyl cyanoacetate (24, 0.8 mL, 8.0 mmol) and unpurified amidine 16 (2.0 g, 12 mmol) in methanol was added a solution of sodium methoxide in methanol (30.0 mL, 15.0 mmol, 0.5 M in methanol). The resulting solution was heated to 60° C. for 4 hours. After the reaction was allowed to cool to room temperature, the solvent was removed in vacuo, and the residue was dissolved in distilled water (15 mL) and saturated with sodium chloride. The aqueous solution was extracted with tetrahydrofuran (3×100 mL), and the combined organic layers were dried over sodium sulfate. After evaporation of the solvents, compound 30 (1.4 g) was used in the next step without further purification. Compound 30 was characterized using LC/MS (LRMS (MH) m/z: 282.34).

To a 0° C. solution of unpurified amine 30 (400 mg, 1.42 mmol) in tetrahydrofuran (60 mL) were successively added diisopropylethylamine (1.0 mL) and acetyl chloride (0.24 mL, 2.82 mmol). The resulting solution was stirred at 0° C. for 6 hours. The reaction was then quenched with aqueous sodium bicarbonate solution and extracted with dichloromethane (3×60 mL) and ethyl acetate (3×60 mL). The combined organic layers were then dried over sodium sulfate. After evaporation of the solvents, the residue was purified by flash chromatography (silica gel, dichloromethane/methanol) to provide the desired pyrimidinone 31 (265 mg), which was characterized by $^1$H-NMR and LC/MS (LRMS (MH) m/z: 324.38).

Example 4

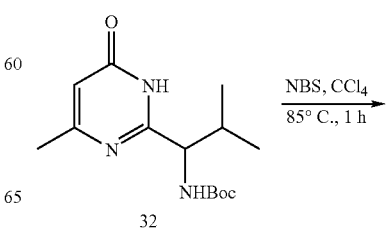

32

-continued

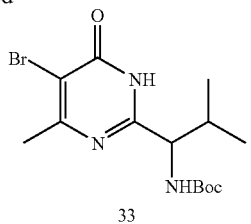
33

To a room temperature solution of pyrimidinone 32 (4.66 g, 16.6 mmol) in carbon tetrachloride (75 mL) was added N-bromosuccinimide (2.95 g, 16.6 mmol). The resulting mixture was heated to 85° C. for 1 hour. The reaction mixture was then quenched with water (50 mL), and extracted with dichloromethane (3×25 mL). The combined organic layers were washed with brine and dried over sodium sulfate. After evaporation of the solvents, the crude product was purified by flash chromatography (silica gel, ethyl acetate and hexane) to provide bromide 33 as a white solid (3.24 g), which was characterized by $^1$H-NMR and LC/MS (LRMS (MH) m/z: 360.25).

Example 5

General Procedure to Prepare the Desired Pyrimidinones

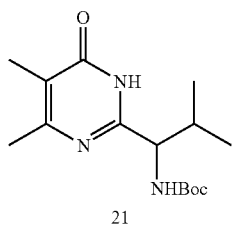
21
→ BnOTs, 60° C. / LiH, Dioxane →

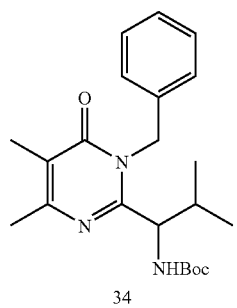
34
→ TFA/DCM / RT →

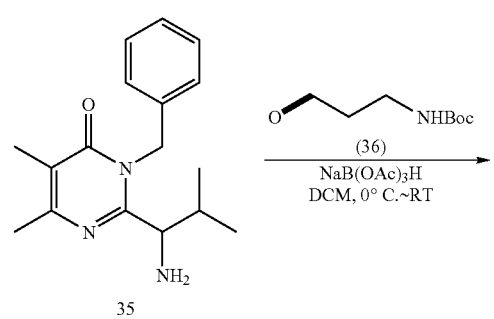
35
→ (36) NaB(OAc)$_3$H / DCM, 0° C.~RT →

-continued

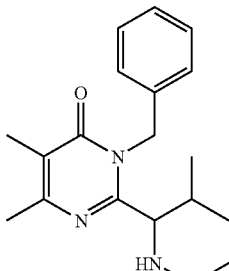
37
→ p-MeC$_6$H$_5$COCl / DIEA, DCM, RT →

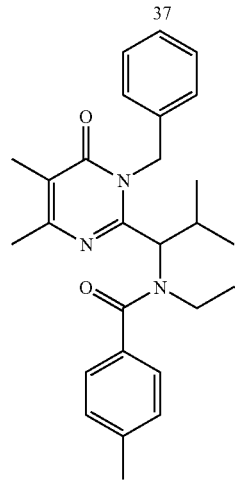
38
→ TFA/DCM / RT →

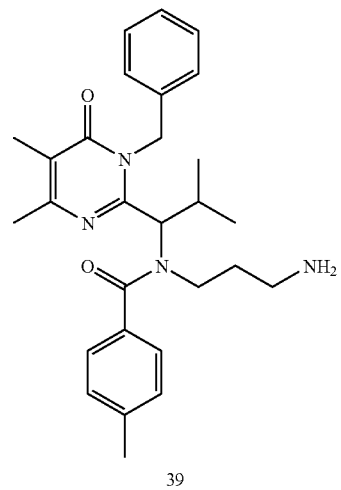
39

To a room temperature solution of pyrimidinone 21 (670 mg, 2.27 mmol) in dioxane (30 mL) was added lithium hydride (23 mg, 2.27 mmol). The resulting suspension was stirred for 15 minutes. Benzyl tosylate (774 mg, 2.95 mmol) was then added, and the reaction mixture was heated to 60° C. for 16 hours under nitrogen. Most of the dioxane was removed under reduced pressure, and the residue was diluted with ethyl acetate (50 mL) and distilled water (50 mL). The layers were separated and the aqueous phase was extracted with ethyl acetate (3×25 mL). The combined organic layers were washed with brine and dried over sodium sulfate. After evaporation of the solvents, the crude product was purified by flash chromatography (silica gel, diethyl ether and dichloromethane) to yield the desired product 34 (686 mg) as a white solid, which was characterized by ¹H-NMR and LC/MS (LRMS (MH) m/z: 385.50).

To a 0° C. solution of pyrimidinone 34 (99 mg 0.26 mmol) in dichloromethane (5 mL) was added trifluoroacetic acid (5 mL). The resulting solution was stirred at room temperature for 1 hour. Most of solvents were then removed in vacuo; the residue was then dried under high vacuum for 1 hour. The resulting material was then diluted with ethyl acetate (50 mL) and washed with saturated sodium bicarbonate solution (25 mL). The aqueous phase was extracted with ethyl acetate (3×25 mL), and the combined organic layers were dried over sodium sulfate. After evaporation of the solvents, amine 35 (65 mg) was used in the next step without further purification. Compound 35 was characterized by ¹H-NMR and LC/MS (LRMS (MH) m/z: 285.38).

To a room temperature solution of amine 35 (744 mg, 2.61 mmol) in dichloromethane (25 mL) were successively added sodium triacetoxyborohydride (718 mg, 3.39 mmol) and aldehyde 36 (587 mg, 3.39 mmol). The resulting mixture was stirred at room temperature under nitrogen for 3 hours until almost no starting material was present. The reaction was then quenched with saturated aqueous sodium bicarbonate, and the aqueous phase was extracted with dichloromethane (3×60 mL). The combined organic layers were dried over sodium sulfate and concentrated in vacuo. The resulting residue was purified by flash chromatography (silica gel, dichloromethane/methanol) to provide desired product 37 (1.038 g), which was characterized by LC/MS (LRMS (MH) m/z: 442.59).

To a 0° C. solution of pyrimidinone 37 (1.038 g, 2.35 mmol) in dichloromethane (25 mL) were added diisopropylethylamine (1.0 mL) and p-toluoyl chloride (434 mg, 2.81 mmol), successively. The resulting solution was stirred at room temperature under nitrogen overnight. The reaction was then quenched with saturated aqueous sodium bicarbonate, and the resulting aqueous phase was extracted with dichloromethane (4×50 mL). The combined organic layers were dried over sodium sulfate. After evaporation of the solvent, the residue was purified by flash column chromatography (silica gel, dichloromethane and methanol) to provide product 38 (943 mg), which was characterized by ¹H-NMR and LC/MS (LRMS (MH) m/z: 560.73).

To a 0° C. solution of pyrimidinone 38 (72 mg, 0.13 mmol) in dichloromethane (10 mL) was added trifluoroacetic acid (10 mL). The resulting solution was stirred at room temperature for 2 hours and then concentrated in vacuo. The residue was then dried under high vacuum for 1 hour and dissolved in ethyl acetate (25 mL). The mixture was washed with saturated aqueous sodium bicarbonate, and the aqueous phase was extracted with ethyl acetate (3×50 mL). The combined organic layers were dried over sodium sulfate and concentrated in vacuo; the residue was purified by flash column chromatography (silica gel, methanol/dichloromethane) to provide the desired product 39 (57 mg), which was fully characterized by ¹H-NMR and LC/MS analysis (LRMS (MH) m/z: 460.61)

Using the procedures set forth above, the following compounds were prepared:

| Structure | Molecular Mass |
| --- | --- |
| N-(3-Amino-propyl)-N-[1-(1-benzyl-4-methyl-6-oxo-1,6-dihydro-pyrimidin-2-yl)-2-methyl-propyl]-4-methyl-benzamide | 446.58462 |
| N-(3-Amino-propyl)-N-[1-(1-benzyl-6-oxo-4-phenyl-1,6-dihydro-pyrimidin-2-yl)-2-methyl-propyl]-4-methyl-benzamide | 508.654 |
| N-(3-Amino-propyl)-N-[1-(1-benzyl-6-oxo-4-propyl-1,6-dihydro-pyrimidin-2-yl)-2-methyl-propyl]-4-methyl-benzamide | 474.63778 |
| N-(3-Amino-propyl)-N-[1-(1-benzyl-4-isopropyl-6-oxo-1,6-dihydro-pyrimidin-2-yl)-2-methyl-propyl]-4-methyl-benzamide | 474.63778 |
| N-(3-Amino-propyl)-N-[1-(1-benzyl-4-methoxymethyl-6-oxo-1,6-dihydro-pyrimidin-2-yl)-2-methyl-propyl]-4-methyl-benzamide | 476.6106 |
| N-(3-Amino-propyl)-N-[1-(1-benzyl-4-hydroxymethyl-6-oxo-1,6-dihydro-pyrimidin-2-yl)-2-methyl-propyl]-4-methyl-benzamide | 462.58402 |
| N-(3-Amino-propyl)-N-[1-(1-benzyl-6-oxo-4-trifluoromethyl-1,6-dihydro-pyrimidin-2-yl)-2-methyl-propyl]-4-methyl-benzamide | 500.5560096 |
| N-(3-Amino-propyl)-N-[1-(1-benzyl-4,5-dimethyl-6-oxo-1,6-dihydro-pyrimidin-2-yl)-2-methyl-propyl]-4-methyl-benzamide | 460.6112 |
| N-(3-Amino-propyl)-N-[1-(3-benzyl-4-oxo-3,4,5,6,7,8-hexahydro-quinazolin-2-yl)-2-methyl-propyl]-4-methyl-benzamide | 486.64848 |
| N-(3-Amino-propyl)-N-[1-(1-benzyl-4-methoxy-6-oxo-1,6-dihydro-pyrimidin-2-yl)-2-methyl-propyl]-4-methyl-benzamide | 462.58402 |
| N-[1-(4-Acetylamino-1-benzyl-6-oxo-1,6-dihydro-pyrimidin-2-yl)-2-methyl-propyl]-N-(3-amino-propyl)-4-methyl-benzamide | 489.6094 |
| N-(3-Amino-propyl)-N-[1-(1-benzyl-5-methyl-6-oxo-1,6-dihydro-pyrimidin-2-yl)-2-methyl-propyl]-4-methyl-benzamide | 446.58462 |
| N-(3-Amino-propyl)-N-[1-(1-benzyl-6-oxo-1,6-dihydro-pyrimidin-2-yl)-2-methyl-propyl]-4-methyl-benzamide | 432.55804 |
| N-(3-Amino-propyl)-N-[1-(1-benzyl-5-isopropyl-4-methyl-6-oxo-1,6-dihydro-pyrimidin-2-yl)-2-methyl-propyl]-4-methyl-benzamide | 488.66436 |
| N-(3-Amino-propyl)-N-[1-(1-benzyl-5-fluoro-4-methyl-6-oxo-1,6-dihydro-pyrimidin-2-yl)-2-methyl-propyl]-4-methyl-benzamide | 464.5750832 |
| N-(3-Amino-propyl)-N-[1-(1-benzyl-5-bromo-4-methyl-6-oxo-1,6-dihydro-pyrimidin-2-yl)-2-methyl-propyl]-4-methyl-benzamide | 525.48068 |
| N-(3-Amino-propyl)-N-[1-(1,5-dibenzyl-4-methyl-6-oxo-1,6-dihydro-pyrimidin-2-yl)-2-methyl-propyl]-4-methyl-benzamide | 536.70716 |
| N-(3-Amino-propyl)-N-[1-(1-benzyl-5-cyano-4-methyl-6-oxo-1,6-dihydro-pyrimidin-2-yl)-2-methyl-propyl]-4-methyl-benzamide | 471.59412 |
| N-(3-Amino-propyl)-N-[1-(1-benzyl-4,5-dimethyl-6-oxo-1,6-dihydro-pyrimidin-2-yl)-2-methyl-propyl]-3-fluoro-4-methyl-benzamide | 478.6016632 |
| N-(3-Amino-propyl)-N-[1-(1-benzyl-4,5-dimethyl-6-oxo-1,6-dihydro-pyrimidin-2-yl)-2-methyl-propyl]-4-methoxy-benzamide | 476.6106 |
| 5-Methyl-isoxazole-3-carboxylic acid (3-amino-propyl)-[1-(1-benzyl-4,5-dimethyl-6-oxo-1,6-dihydro-pyrimidin-2-yl)-2-methyl-propyl]-amide | 451.56142 |
| Benzo[1,2,3]thiadiazole-5-carboxylic acid (3-amino-propyl)-[1-(1-benzyl-4,5-dimethyl-6-oxo-1,6-dihydro-pyrimidin-2-yl)-2-methyl-propyl]-amide | 504.64822 |
| N-(3-Amino-propyl)-N-[1-(1-benzyl-4,5-dimethyl-6-oxo-1,6-dihydro-pyrimidin-2-yl)-2-methyl-propyl]-6-methyl-nicotinamide | 461.5993 |
| 5-Methyl-pyrazine-2-carboxylic acid (3-amino-propyl)-[1-(1-benzyl-4,5-dimethyl-6-oxo-1,6-dihydro-pyrimidin-2-yl)-2-methyl-propyl]-amide | 462.5874 |
| N-(3-Amino-propyl)-N-[1-(1-benzyl-4,5-dimethyl-6-oxo-1,6-dihydro-pyrimidin-2-yl)-2-methyl-propyl]-4-cyano-benzamide | 471.59412 |
| N-(3-Amino-propyl)-N-[1-(1-benzyl-4,5-dimethyl-6-oxo-1,6-dihydro-pyrimidin-2-yl)-2-methyl-propyl]-2-methoxy-acetamide | 414.54122 |

-continued

| Structure | Molecular Mass |
|---|---|
| N-(3-Amino-propyl)-N-[1-(1-benzyl-4,5-dimethyl-6-oxo-1,6-dihydro-pyrimidin-2-yl)-2-methyl-propyl]-4-methyl-benzenesulfonamide | 496.6659 |
| Benzo[1,3]dioxole-5-carboxylic acid (3-amino-propyl)-[1-(1-benzyl-4,5-dimethyl-6-oxo-1,6-dihydro-pyrimidin-2-yl)-2-methyl-propyl]-amide | 490.59412 |
| 2-{1-[(3-Amino-propyl)-(4-methyl-benzoyl)-amino]-2-methyl-propyl}-1-benzyl-5-methyl-6-oxo-1,6-dihydro-pyrimidine-4-carboxylic acid ethyl ester | 518.64728 |
| 5-Methyl-thiophene-2-carboxylic acid (3-amino-propyl)-[1-(1-benzyl-4,5-dimethyl-6-oxo-1,6-dihydro-pyrimidin-2-yl)-2-methyl-propyl]-amide | 466.63992 |

Example 6

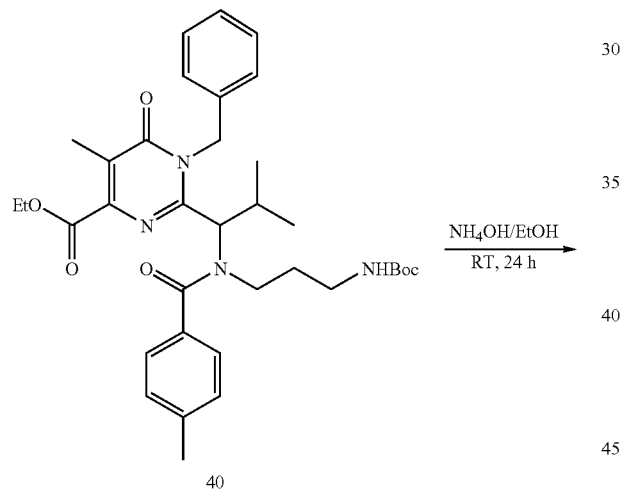

40

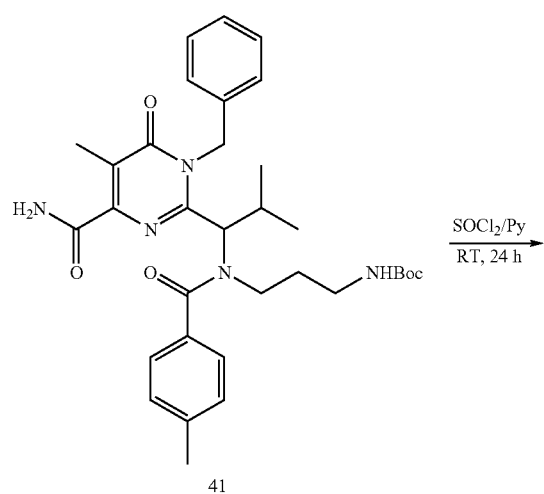

41

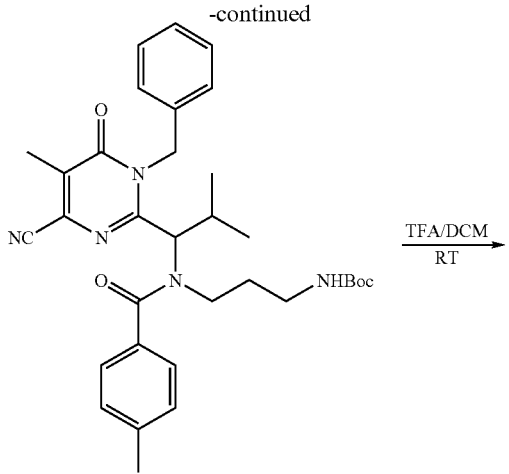

42

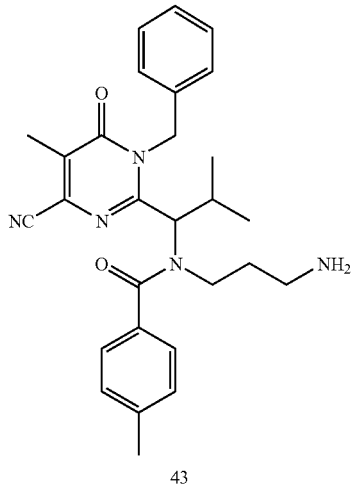

43

To a room temperature solution of pyrimidinone 40 (238 mg, 0.385 mmol) in ethanol (3 mL) was added concentrated aqueous ammonia (5 mL). The resulting mixture was stirred at room temperature for 24 hours. The ethanol was then removed in vacuo, and the remaining aqueous layer was extracted with ethyl acetate (3×10 ml). The combined organic layers were washed with brine and dried over sodium sulfate. After evaporation of the solvents, the resulting amorphous solid was purified by flash chromatography (silica gel, ethyl acetate/hexane) to provide 41 (135 mg) as a white solid, which was characterized by $^1$H-NMR and LC/MS analysis (LRMS (MH) m/z: 589.73).

To a room temperature solution of pyrimidinone 41 (76 mg, 0.128 mmol) in pyridine (5 mL) was added thionyl chloride (200 µL, 1.03 mmol). The reaction mixture was stirred at room temperature for 16 hours. The solvent was then removed in vacuo and the residue purified by flash chromatography (silica gel, ethyl acetate/hexane) to provide nitrile 42 (46 mg) as a white solid, which was characterized by $^1$H-NMR and LC/MS (LRMS (MH) m/z: 571.71).

To a 0° C. solution of pyrimidinone 42 (46 mg, 0.08 mmol) in dichloromethane (5 mL) was added trifluoroacetic acid (5 mL). The resulting solution was stirred at room temperature for 2 hours and then concentrated in vacuo. The residue was dried under high vacuum for 1 hour and then dissolved in ethyl acetate (25 mL). The resulting solution was washed with saturated aqueous sodium bicarbonate, and the aqueous phase was extracted with ethyl acetate (3×50 mL). The combined organic layers were dried over sodium sulfate and concentrated in vacuo. Purification by flash column chromatography (silica gel, methanol/dichloromethane) provided the desired product 43 (27 mg), which was characterized by ¹H-NMR and LC/MS analysis (LRMS (MH) m/z: 471.59).

Using the procedures set forth above, the following compounds were prepared:

| Structure | Molecular Mass |
| --- | --- |
| 2-{1-[(3-Amino-propyl)-(4-methyl-benzoyl)-amino]-2-methyl-propyl}-1-benzyl-5-methyl-6-oxo-1,6-dihydro-pyrimidine-4-carboxylic acid ethyl ester | 518.64728 |
| 2-{1-[(3-Amino-propyl)-(4-methyl-benzoyl)-amino]-2-methyl-propyl}-1-benzyl-5-methyl-6-oxo-1,6-dihydro-pyrimidine-4-carboxylic acid amide | 489.6094 |
| N-(3-Amino-propyl)-N-[1-(1-benzyl-4-cyano-5-methyl-6-oxo-1,6-dihydro-pyrimidin-2-yl)-2-methyl-propyl]-4-methyl-benzamide | 471.59412 |

Example 7

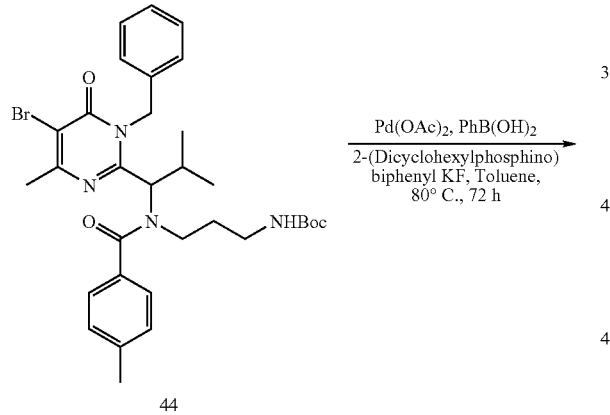

44

Pd(OAc)₂, PhB(OH)₂
2-(Dicyclohexylphosphino)biphenyl KF, Toluene, 80° C., 72 h

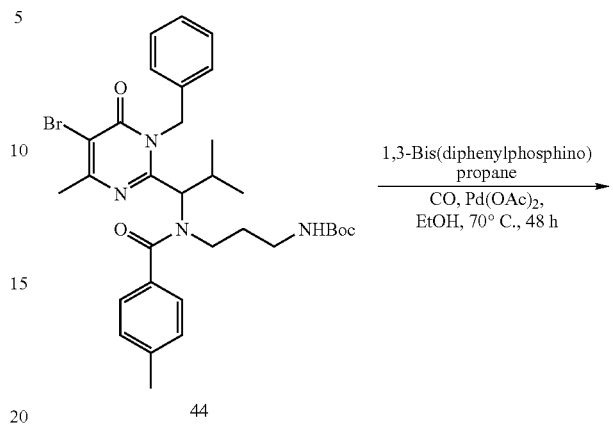

44

1,3-Bis(diphenylphosphino)propane
CO, Pd(OAc)₂, EtOH, 70° C., 48 h

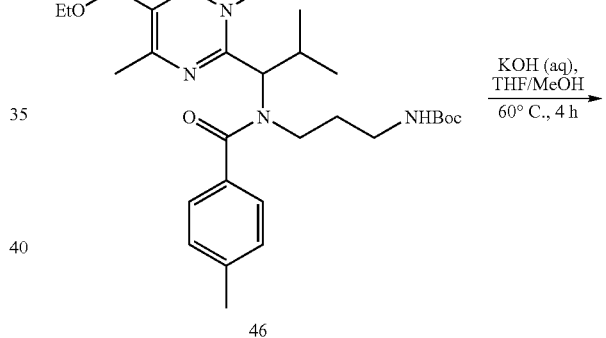

46

KOH (aq), THF/MeOH
60° C., 4 h

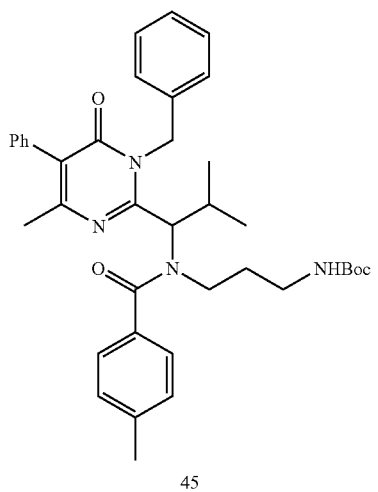

45

47

1) isobutyl chloroformate DIEA, THF, RT, 3 h
2) NH₃(g), RT, 2 h

-continued

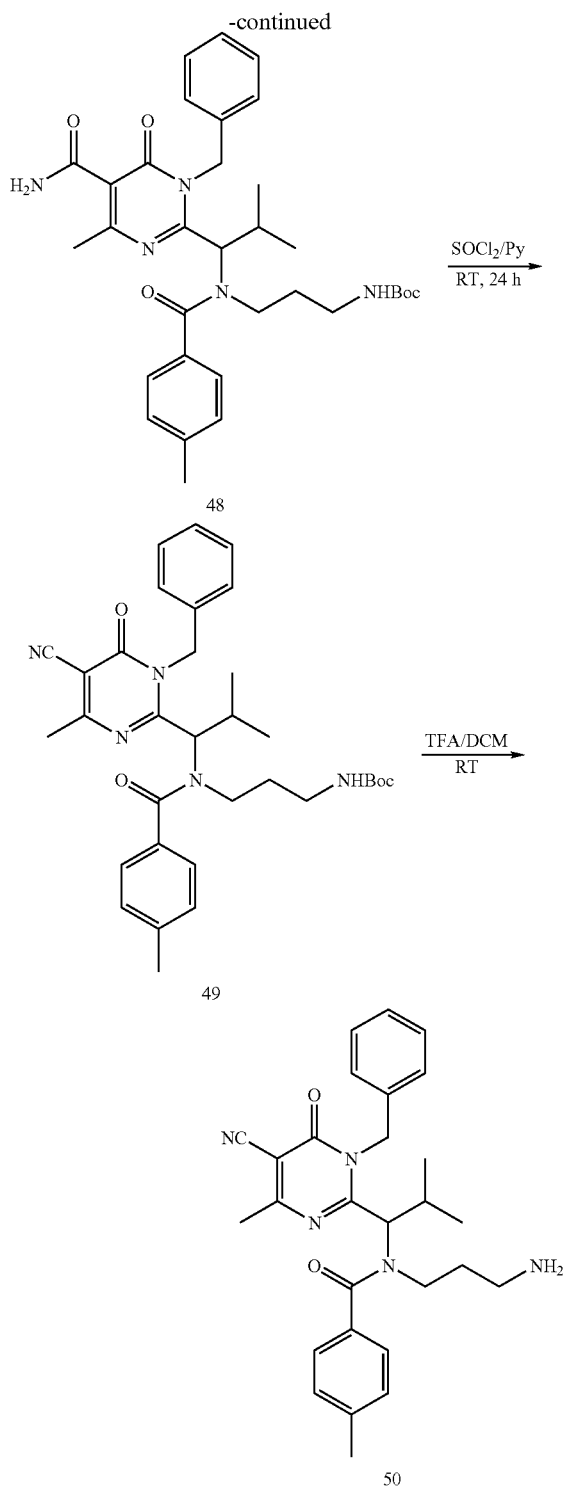

Pyrimidinone 44 (375 mg, 0.599 mmol), 2-(dicyclohexylphosphino)biphenyl (4.0 mg, 0.012 mmol), palladium acetate (1.3 mg, 0.006 mmol), phenylboronic acid (110 mg, 0.899 mmol), and potassium fluoride (104 mg, 1.798 mmol) were placed in a resealable Schlenk tube. The tube was evacuated and back-filled with nitrogen 3 times. Toluene (3 mL) was then added by syringe, and the resulting mixture was heated to 80° C. for 72 h. The reaction mixture was then diluted with diethyl ether (15 mL) and washed with aqueous potassium hydroxide solution (20 mL, 1 M). The aqueous layers were extracted with diethyl ether (2×15 mL), and the combined organic layers were dried over sodium sulfate and concentrated in vacuo. Purification by flash column chromatography (silica gel, ethyl acetate/hexane) yielded the desired product 45 (160 mg), which was fully characterized by $^1$H-NMR and LC/MS analysis (LRMS (MH) m/z: 622.80).

To a solution of pyrimidinone 44 (750 mg, 1.20 mmol) in anhydrous ethanol (5 mL) in a thick-walled glass tube was added 1,3-bis(diphenylphosphino)propane (124 mg, 0.30 mmol), triethylamine (1.673 mL, 12.0 mmol) and palladium acetate (51 mg, 0.23 mmol). The tube was evacuated and back-filled with carbon monoxide three times and then pressurized with carbon monoxide (30 psi). The mixture was heated to 70° C. for 48 hours. The ethanol was evaporated, and the residue was diluted with ethyl acetate (20 mL) and water (20 mL). The layers were separated and the aqueous phase was extracted with ethyl acetate (3×10 mL). The combined organic layers were dried over sodium sulfate and concentrated in vacuo. Purification by flash chromatography (silica gel, ethyl acetate/hexane) provided 46 (357 mg), which was characterized by $^1$H-NMR and LC/MS analysis (LRMS (MH) m/z: 618.76).

To a room temperature solution of ester 46 (382 mg, 0.617 mmol) in tetrahydrofuran (10 mL) and methanol (5 mL) was added aqueous potassium hydroxide (2.5 mL, 1.0 M). The resulting mixture was heated to 70° C. for 4 hours. The reaction was allowed to cool to room temperature, and the solvents were removed in vacuo. The residue was diluted with ethyl acetate and acidified with aqueous hydrochloric acid (1.0 M). The aqueous layer was extracted with ethyl acetate (3×15 mL). The combined organic layers were dried over sodium sulfate and concentrated. Acid 47 (320 mg) was used in the next step without further purification. Compound 47 was characterized by $^1$H-NMR and LC/MS analysis (LRMS (MH) m/z: 590.71).

To a room temperature solution of acid 47 (310 mg, 0.53 mmol) in anhydrous tetrahydrofuran (5 mL) were successively added diisopropylethylamine (274 µL, 1.58 mmol) and isobutyl chloroformate (83 µL, 0.63 mmol). The resulting mixture was stirred for 3 hours at room temperature under an atmosphere of nitrogen. The reaction was then cooled to 0° C. and purged with gaseous ammonia for 45 minutes. The mixture was then allowed to warm to room temperature for an addition 45 minutes. The solvents were removed in vacuo, and the residue was diluted with ethyl acetate (15 mL) and water (15 mL). The layers were separated, and the aqueous phase was extracted with ethyl acetate (2×15 mL). The combined organic layers were dried over sodium sulfate and concentrated in vacuo. Purification by flash column chromatography (silica gel, ethyl acetate/hexane) yielded product 48 (156 mg), which was characterized by $^1$H-NMR and LC/MS analysis (LRMS (MH) m/z: 589.73).

To a room temperature solution of pyrimidinone 48 (105 mg, 0.178 mmol) in pyridine (10 mL) was added thionyl chloride (250 µL, 1.25 mmol). The reaction mixture was stirred at room temperature for 16 hours. The solvents were then removed in vacuo, and the residue was purified by flash chromatography (silica gel, ethyl acetate/hexane) to provide 49 (65 mg) as a glassy solid, which was characterized by $^1$H-NMR and LC/MS (LRMS (MH) m/z: 571.71).

To a 0° C. solution of pyrimidinone 49 (65 mg, 0.08 mmol) in dichloromethane (5 mL) was added trifluoroacetic acid (5 mL). The resulting solution was stirred at room temperature for 2 hours and then concentrated in vacuo. The residue was dried under high vacuum for 1 hour and then dissolved in ethyl acetate (25 mL). The resulting solution was washed with saturated aqueous sodium bicarbonate, and the aqueous phase was extracted with ethyl acetate (3×50 mL). The combined organic layers were dried over sodium sulfate and concentrated in vacuo. Purification by flash column chromatography (silica gel, methanol/dichloromethane) provided the desired product 50 (37 mg), which was fully characterized by $^1$H-NMR and LC/MS analysis (LRMS (MH) m/z: 471.59).

Using the procedures set forth above, the following compounds were prepared:

| Structure | Molecular Mass |
| --- | --- |
| N-(3-Amino-propyl)-N-[1-(1-benzyl-5-bromo-4-methyl-6-oxo-1,6-dihydro-pyrimidin-2-yl)-2-methyl-propyl]-4-methyl-benzamide | 525.48068 |
| N-(3-Amino-propyl)-N-[1-(1-benzyl-4-methyl-6-oxo-5-phenyl-1,6-dihydro-pyrimidin-2-yl)-2-methyl-propyl]-4-methyl-benzamide | 522.68058 |
| 2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid ethyl ester | 518.64728 |
| 2-{1-[(3-Amino-propyl)-(4-methyl-benzoyl)-amino]-2-methyl-propyl}-1-benzyl-4-methyl-6-oxo-1,6-dihydro-pyrimidine-5-carboxylic acid amide | 489.6094 |
| N-(3-Amino-propyl)-N-[1-(1-benzyl-5-cyano-4-methyl-6-oxo-1,6-dihydro-pyrimidin-2-yl)-2-methyl-propyl]-4-methyl-benzamide | 471.59412 |

Example 8

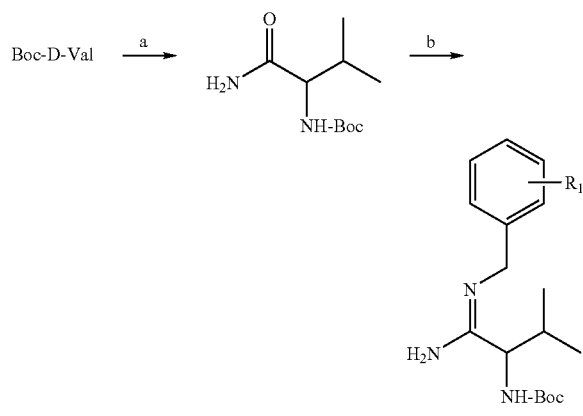

Conditions: a) iBuOCOCl, Et$_3$N, THF; NH$_4$OH; b) Et$_3$O.PF$_6$, CH$_2$Cl$_2$; R$_1$PhCH$_2$NH$_2$, EtOH, 60° C., 24 h.

[(R)-1-(N-Benzyl-carbamimidoyl)-2-methyl-propyl]-carbamic acid t-butyl ester a) Boc-D-Valine amide To a stirred solution of Boc-D-Valine (25 g, 115 mMol) in THF (300 mL) at 0° C. was added N-Methylmorpholine (15 mL, 136 mMol) followed by the dropwise addition of isoButyl chloroformate (18 mL, 139 mMol) over 5 minutes. The reaction was stirred at 0° C. for 30 minutes after which a solution of 30 wt. % NH$_4$OH (50 mL, 385 mMol) was quickly poured into the reaction. (Vigorous gas evolution was seen which subsided after a few minutes.) The reaction was allowed to warm to RT and stirred for 4 h. The reaction was concentrated under vacuum on the rotoevaporator to a volume which precipitated most of the product. The thick white slurry was diluted with an equal volume of water, filtered, rinsed with water, pressed dry then dried under vacuum to give the title compound (22.56 g, 91%) as a white solid: $^1$H NMR (400 MHz, CDCl$_3$) δ 6.17 (br s, 1H), 5.75 (br s, 1H), 5.12 (d, 1H), 4.00 (app. t, 1H), 2.13 (m, 1H), 1.44 (s, 9H), 0.99 (d, 3H), 0.94 (d, 3H).

b) [(R)-1-(N-Benzyl-carbamimidoyl)-2-methyl-propyl]-carbamic acid t-butyl ester

To a stirred solution of Boc-D-Valine amide (10 g, 46 mMol) in CH$_2$Cl$_2$ (200 mL) was added Triethyloxonium hexafluorophosphate (13.0 g, 48 mMol). (The reaction started out as a suspension which gradually cleared.) The reaction was stirred for 48 h at RT, poured into a separatory funnel, washed with 1 N Na$_2$CO$_3$, dried (Na$_2$SO$_4$), filtered and concentrated under vacuum. To the remaining oil was added Benzylamine (5.0 mL, 23 mMol) and EtOH (20 mL). The reaction was stirred at 60° C. for 24 h. After cooling to RT the reaction was evaporated under vacuum. The title compound (14.16 g, >95% pure by LCMS) was obtained without purification as a pale yellow oil which eventually solidified to a waxy solid: MS (ES) m/e 306.4 (M+H)$^+$.

Example 9

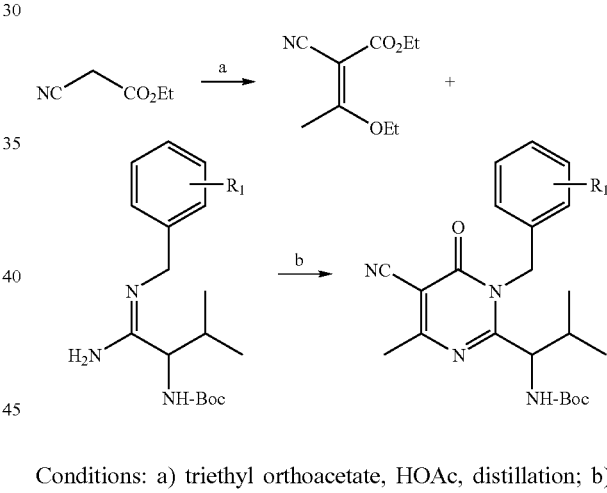

Conditions: a) triethyl orthoacetate, HOAc, distillation; b) EtOH, reflux, 18 h.

[1-(3-Benzyl-5-cyano-6-methyl-4-oxo-3,4-dihydro-pyrimidin-2-yl)-2-methyl-propyl]-carbamic acid-t-butyl ester a) Ethyl 2-ethoxyethylidene-cyanoacetate To a stirred solution of Ethyl cyanoacetate (46.8 g, 414 mMol) and Triethyl orthoacetate (84.4 g, 520 mMol), in a 250 mL round bottom flask fitted with a short path distillation head, was added HOAc (1.2 mL, 21 mMol). The reaction was slowly heated to 135° C. and maintained at that temperature to distill off the ethyl alcohol that was produced. (Distillation started at ~106° C.) At 15 min. intervals HOAc (1.2 mL, 21 mMol) was added to the reaction for an additional three times. The reaction was then slowly heated to 150° C. then cooled back down to ~80° C. The title product (62.64 g, 82%) was obtained by short path distillation under high vacuum (bp 128° C., HV) as a pale yellow crystalline solid. (Note: Cooling to the condensor was shut off to prevent plugging.): $^1$H NMR (400 MHz, CDCl$_3$) δ 4.27 (q, 2H), 4.22 (q, 2H), 2.61 (s, 3H), 1.43 (t, 3H), 1.31 (t, 3H).

b) [1-(3-Benzyl-5-cyano-6-methyl-4-oxo-3,4-dihydro-pyrimidin-2-yl)-2-methyl-propyl]-carbamic acid-t-butyl ester To a stirred solution of [(R)-1-(N-Benzyl-carbamimidoyl)-2-methyl-propyl]-carbamic acid t-butyl ester (14.16 g, 46 mMol) in EtOH (50 mL) was added Ethyl 2-ethoxyethylidene-cyanoacetate (8.4 g, 46 mMol). The reaction was refluxed for 18 h, cooled to RT and concentrated under vacuum. Purification by flash chromatography on silica gel (5% EtOAc, CH$_2$Cl$_2$) followed by crystallization from EtOAc, hexane and Et$_2$O, pet. ether gave the title compound (8.03 g, 44%) as a white solid: MS (ES) m/e 397.2 (M+H)$^+$.

Example 10

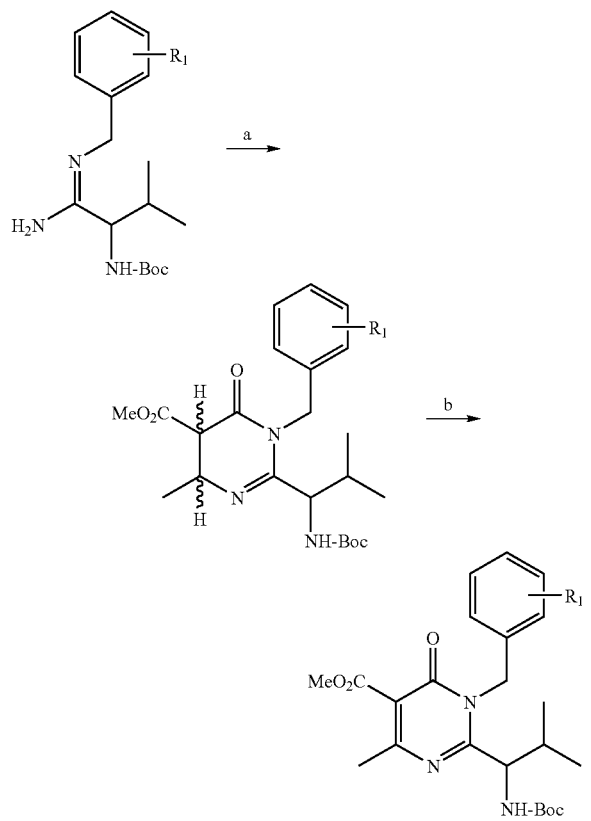

Conditions: a) dimethyl ethylidenemalonate, MeOH; b) NBS, cat. benzoyl peroxide, K$_2$CO$_3$, CCl$_4$ reflux 1-Benzyl-2-(1-t-butoxycarbonylamino-2-methyl-propyl)-4-methyl-6-oxo-1,6-dihydro-pyrimidine-5-carboxylic acid methyl ester a) 1-Benzyl-2-(1-t-butoxycarbonylamino-2-methyl-propyl)-4-methyl-6-oxo-1,4,5,6-tetrahydro-pyrimidine-5-carboxylic acid methyl ester To a solution of [(R)-1-(N-Benzyl-carbamimidoyl)-2-methyl-propyl]-carbamic acid t-butyl ester (7.08 g, 23 mMol) in MeOH (15 mL) was added Dimethyl ethylidenemalonate (3.64 g, 23 mMol). The reaction was slowly heated to 110° C.

allowing the MeOH to distill off. The reaction was stirred for 5 h at 110° C. then allowed to cool to RT. Purification by flash chromatography (25% EtOAc, hexane) gave the title compound (6.37 g, 64%) as an oil: ~(3:1) mixture of diastereomers by LCMS; MS (ES) m/e 432.2 and 432.4 (M+H)$^+$.

b) 1-Benzyl-2-(1-t-butoxycarbonylamino-2-methyl-propyl)-4-methyl-6-oxo-1,6-dihydro-pyrimidine-5-carboxylic acid methyl ester To a stirred solution of 1-Benzyl-2-(1-t-butoxycarbonylamino-2-methyl-propyl)-4-methyl-6-oxo-1,4,5,6-tetrahydro-pyrimidine-5-carboxylic acid methyl ester (6.37 g, 14.8 mMol) in CCl$_4$ (150 mL) was added K$_2$CO$_3$ (4.0 g, 29 mMol), N-Bromosuccinimde (2.63 g, 14.8 mMol) and Benzoyl peroxide (0.18 g, 0.74 mMol). The reaction was refluxed for 0.5 h, cooled to RT, filtered through a pad of Celite®, and rinsed with CH$_2$Cl$_2$. The filtrate was concentrated under vacuum and purified by flash chromatography (step gradient of 0 to 5% EtOAc in CH$_2$Cl$_2$). The semi-purified product obtained was taken up in a solution of 20% EtOAc in hexane (10 mL) at which point the product began to crystallize out. The mixture was diluted with a solution of 10% Et$_2$O in pet. Et$_2$O (50 mL), triturated, filtered and dried under vacuum to give the title compound (2.56 g, 40%) as a white solid: MS (ES) m/e 432.2 and 430.2 (M+H)$^+$.

Example 11

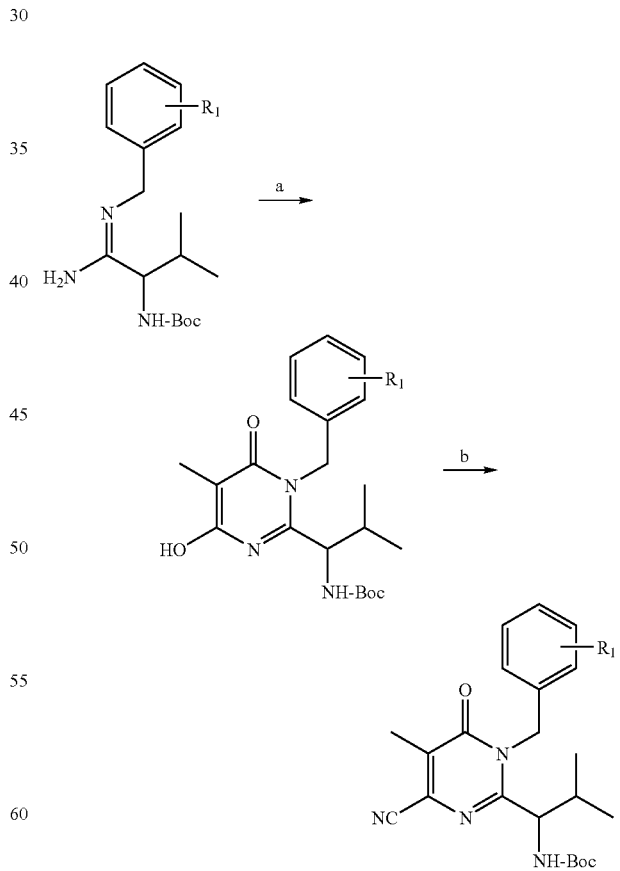

Conditions: a) 2-Chlorocarbonyl-propionic acid ethyl ester, Et$_3$N, CH$_2$Cl$_2$; DMF 100° C. 18 h; b) NaH, DMF; PhN(Tf)$_2$; Zn(CN)$_2$, (PPh$_3$)$_4$Pd, DMF, 90° C., 4 h.

[1-(3-Benzyl-5-methyl-6-cyano-4-oxo-3,4-dihydro-pyrimidin-2-yl)-2-methyl-propyl]-carbamic acid-t-butyl ester a) [1-(3-Benzyl-5-methyl-6-hydroxy-4-oxo-3,4-dihydro-pyrimidin-2-yl)-2-methyl-propyl]-carbamic acid-t-butyl ester To a stirred solution of [(R)-1-(N-Benzyl-carbamimidoyl)-2-methyl-propyl]-carbamic acid t-butyl ester (16.37 g, 53.6 mMol) in $CH_2Cl_2$ (150 mL) with cooling at 0° C. was added $Et_3N$ (9 mL, 64.3 mMol) followed by 2-chlorocarbonyl-propionic acid ethyl ester (10 g, 60.8 mMol) dropwise over 15 minutes. The reaction was allowed to warm to RT and stirred for 4 h, poured into a separatory funnel, washed with water, brine, dried ($Na_2SO_4$), and evaporated to dryness under vacuum. The unpurified acylamidine (~90% pure by LCMS, MS (ES) m/e (M+H)+434.4) was taken up in DMF (150 mL) and heated to 100° C. with stirring for 18 h. The reaction was concentrated under vacuum and purified by flash chromatography (90:10:1, $CH_2Cl_2$:EtOAc:HOAc) then (30:70:1, EtOAc:hexane:HOAc) to give the title compound (8.42 g, 41%) as an off-white solid: MS (ES) m/e 388.2 (M+H)+.

b) [1-(3-Benzyl-5-methyl-6-cyano-4-oxo-3,4-dihydro-pyrimidin-2-yl)-2-methyl-propyl]-carbamic acid-t-butyl ester To a stirred solution of [1-(3-Benzyl-5-methyl-6-hydroxy-4-oxo-3,4-dihydro-pyrimidin-2-yl)-2-methyl-propyl]-carbamic acid-t-butyl ester (8.42 g, 21.7 mMol) in DMF (150 mL) was added portionwise a 60% dispersion of NaH in mineral oil (0.95 g, 24 mMol). After stirring for 15 minutes at RT, N-Phenyltrifluoromethanesulfonimide (8.6 g, 24 mMol) was added. The reaction was stirred at RT for 18 h, concentrated under vacuum, taken up in EtOAc, washed with sat. $NH_4Cl$, dried ($MgSO_4$), filtered and evaporated under vacuum. Purification by flash chromatography (step gradient of 0 to 5% EtOAc in $CH_2Cl_2$) then (10% EtOAc/hexane) gave the semi-purified triflate (11.70 g), (MS (ES) m/e 520.2 (M+H)+, contained 23% $PhNHSO_2CF_3$ by LCMS) as a white solid.

To the crude triflate with stirring in DMF (150 mL) was added $Zn(CN)_2$ (2.6 g, 22.2 mMol) and $(PPh_3)_4Pd$ (2.6 g, 2.3 mMol). The reaction was heated under Ar at 90° C. for 4 h, cooled to RT, and evaporated under vacuum. Purification by flash chromatography (step gradient of 0 to 5% EtOAc in $CH_2Cl_2$) gave the title compound (7.11 g, 82%) as a white solid: MS (ES) m/e 520.2 (M+H)+.

Example 12

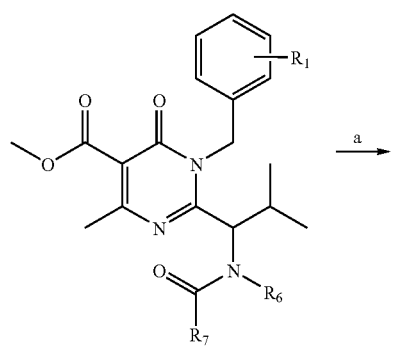

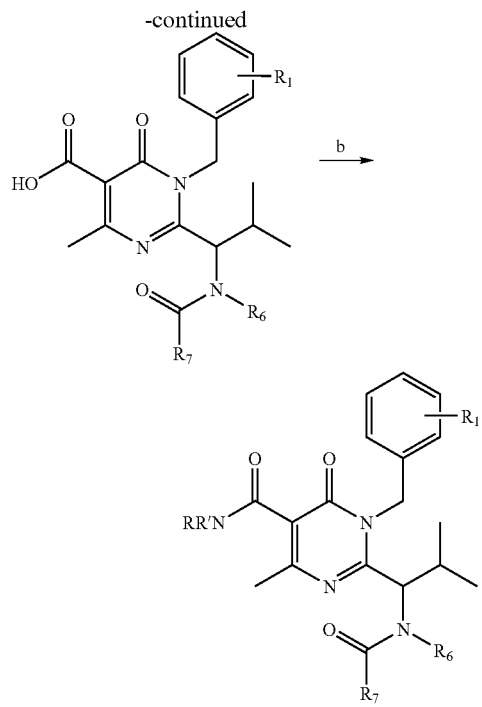

Conditions: a) 1 N KOH, THF, MeOH, 60° C.; b) RR'NH, EDC, HOBt, TEA, $CH_2Cl_2$, ambient temperature; then TFA.

2-{(R)-[(3-Amino-propyl)-(1-p-tolyl-methanoyl)-amino]-methyl-propyl}-1-benzyl-4-methyl-6-oxo-1,6-dihydro-pyrimidine-5-carboxylic acid ethylamide a) 1-Benzyl-2-{(R)-[(3-tert-butoxycarbonylamino-propyl)-(1-p-tolyl-methanoyl)-amino]-methyl-propyl}-4-methyl-6-oxo-1,6-dihydro-pyrimidine-5-carboxylic acid To a solution of 1-benzyl-2-{(R)-[(3-tert-butoxycarbonylamino-propyl)-(1-p-tolyl-methanoyl)-amino]-methyl-propyl}-4-methyl-6-oxo-1,6-dihydro-pyrimidine-5-carboxylic acid methyl ester (2.75 g, 4.55 mmol) in THF (60 mL) was added MeOH (30 mL) followed by 1N KOH (18.2 mL, 18.2 mmol). The resultant solution was heated to 60° C. for 3 h, then concentrated under reduced pressure. The residue was diluted with $H_2O$ (75 mL), adjusted to pH ~7 with 1N HCl, and extracted with EtOAc (3×75 mL). The extracts were dried over $Na_2SO_4$, filtered and concentrated under reduced pressure to give 2.69 g (100%) of 1-benzyl-2-{(R)-[(3-tert-butoxycarbonylamino-propyl)-(1-p-tolyl-methanoyl)-amino]-methyl-propyl}-4-methyl-6-oxo-1,6-dihydro-pyrimidine-5-carboxylic acid as an oil which was used in the subsequent step without purification: MS (ES) m/e 591.4 (M+H)+.

b) 2-{(R)-[(3-Amino-propyl)-(1-p-tolyl-methanoyl)-amino]-methyl-propyl}-1-benzyl-4-methyl-6-oxo-1,6-dihydro-pyrimidine-5-carboxylic acid ethylamide To a solution of 1-benzyl-2-{(R)-[(3-tert-butoxycarbonylamino-propyl)-(1-p-tolyl-methanoyl)-amino]-methyl-propyl}-4-methyl-6-oxo-1,6-dihydro-pyrimidine-5-carboxylic acid (100 mg, 0.169 mmol) in $CH_2Cl_2$ (1.7 mL) was added EDC (36 mg, 0.186 mmol), HOBt (25 mg, 0.186 mmol), TEA (28 uL, 0.203 mmol) followed by ethylamine (85 uL of a 2.0M solution in THF, 0.169 mmol). The reaction mixture was stirred at ambient temperature for 16 h, then TFA (1 mL)

was added. After 3 h, the reaction mixture was concentrated under reduced pressure and the residue was purified by reverse phase HPLC to give 47 mg (53%) of 2-{(R)-[(3-amino-propyl)-(1-p-tolyl-methanoyl)-amino]-methyl-propyl}-1-benzyl-4-methyl-6-oxo-1,6-dihydro-pyrimidine-5-carboxylic acid ethylamide as a pale yellow solid: MS (ES) m/e 518.4 (M+H)+.

Example 13

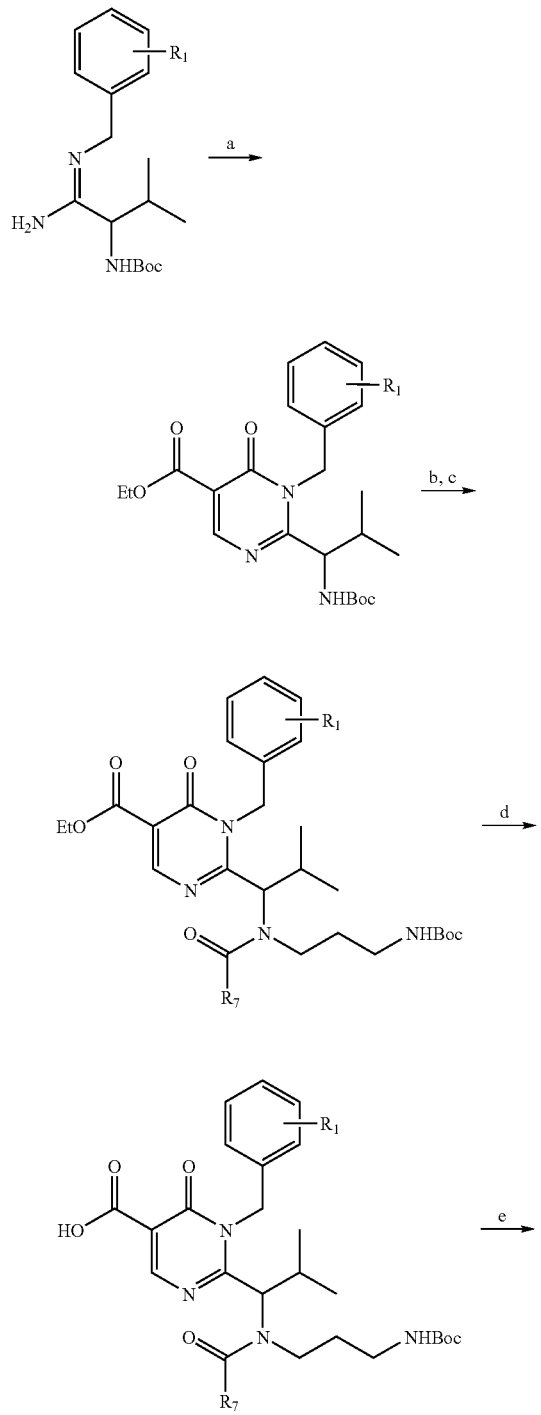

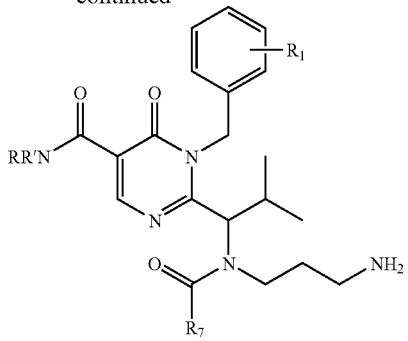

Conditions: a) Diethyl ethoxymethylenemalonate, MeOH; b) 4 M HCl/dioxane then aq. 1 M NaOH; OHC(CH$_2$)$_2$NHBoc, NaB(OAc)$_3$H, CH$_2$Cl$_2$; c) R$_7$COCl, DIEA, CH$_2$Cl$_2$; d) 4 M KOH, EtOH/H$_2$O; e) RR'NH$_2$, EDC/HOBt, DMF; then 4 M HCl/dioxane.

2-{[(3-Amino-propyl)-(1-p-tolyl-methanoyl)-amino]-methyl-propyl}-1-benzyl-6-oxo-1,6-dihydro-pyrimidine-5-carboxylic acid phenylamide hydrochloride a) 1-Benzyl-2-(1-tert-butoxycarbonylamino-2-methyl-propyl)-6-oxo-1,6-dihydro-pyrimidine-5-carboxylic acid ethyl ester Following the procedure of Veale, *J. Org. Chem.*, 58, 4490 (1993), to [1-(N-Benzyl-carbamimidoyl)-2-methyl-propyl]-carbamic acid tert-butyl ester (10.86 g, 35.6 mmol) in methanol (160 mL) was added diethyl ethoxymethylenemalonate (7.7 g, 35.6 mmol). The reaction is equipped with a Dean-Stark trap. The reaction was heated at 100° C. until all solvent was removed. The residue was dissolved in methylene chloride, washed with 1 N HCl and water, dried (Na$_2$SO$_4$), and concentrated. The resulting pale yellow syrup was used in the next step without further purification.

b) 1-Benzyl-2-[1-(3-tert-butoxycarbonylamino-propylamino)-2-methyl-propyl]-6-oxo-1,6-dihydro-pyrimidine-5-carboxylic acid ethyl ester To 1-Benzyl-2-(1-tert-butoxycarbonylamino-2-methyl-propyl)-6-oxo-1,6-dihydro-pyrimidine-5-carboxylic acid ethyl ester (14.22 g from previous step) was added a solution of 4M HCl in 1,4-dioxane (50 mL, 200 mmol) and the reaction was stirred at room temperature for 2.0 h. The reaction was concentrated in vacuo and the residue was dissolved in water and washed with ether. The aqueous layer was basified with 1 N NaOH and extracted into ether. The ether layer was washed with water, dried (Na$_2$SO$_4$), and concentrated to give a crystalline orange solid. This solid (7.08 g, 21.5 mmol) was dissolved in dry CH$_2$Cl$_2$ (100 mL) and to this was added (3-Oxo-propyl)-carbamic acid tert-butyl ester (3.076 g, 17.76 mmol) in dry CH$_2$Cl$_2$ (50 mL) followed by portionwise addition of sodium triacetoxyborohydride (5.65 g, 26.64 mmol). The reaction was stirred for 72 h at room temperature under N$_2$ at which time the reaction was made basic with saturated sodium bicarbonate. The layers were separated, the aqueous layer was extracted with methylene chloride, and the combined organics were washed with brine, dried (Na$_2$SO$_4$), and evaporated to dryness. The residue was purified by flash chromatography on silica gel (1:1 hexanes:EtOAc) to give the title compound as a pale yellow foam (5.59 g, 32%, 3 steps). MS(ES+) m/e 487 [M+H]+.

c) 1-Benzyl-2-{[3-tert-butoxycarbonylamino-propyl)-(1-p-tolyl-methanoyl)-amino]-methylpropyl}-6-oxo-1,6-dihydro-pyrimidine-5-carboxylic acid ethyl ester A solution of 1-Benzyl-2-[1-(3-tert-butoxycarbonylamino-propylamino)-2-methyl-propyl]-6-oxo-1,6-dihydro-pyrimidine-5-carboxylic acid ethyl ester (1.45 g, 2.98 mmol), N,N-diisopropylethylamine (1.93 g, 14.91 mmol), and p-toluoyl chloride (1.38 g, 8.95 mmol) in $CH_2Cl_2$ (30 mL) was stirred at room temperature for 24 h. The reaction was washed with 1 N HCl and brine, dried ($Na_2SO_4$), and evaporated to dryness. The residue was purified by flash chromatography (2:1 hexanes:EtOAc) to give the title compound as a white solid (1.22 g, 68%). MS(ES+) m/e 605 [M+H]+.

d) 1-Benzyl-2-{[3-tert-butoxycarbonylamino-propyl)-(1-p-tolyl-methanoyl)-amino]-methylpropyl}-6-oxo-1,6-dihydro-pyrimidine-5-carboxylic acid To a solution of 1-Benzyl-2-{[3-tert-butoxycarbonylamino-propyl)-(1-p-tolyl-methanoyl)-amino]-methylpropyl}-6-oxo-1,6-dihydro-pyrimidine-5-carboxylic acid ethyl ester (1.22 g, 2.02 mmol) in EtOH (18 mL) was added a solution of potassium hydroxide (0.453 g, 8.068 mmol) in water (2 mL) and the reaction was stirred at room temperature for 24 h. The reaction was concentrated in vacuo and the residue was dissolved in water and acidified with 1N HCl to pH=2. The resulting precipitate was dissolved in EtOAc, washed with water and brine, dried ($Na_2SO_4$), and concentrated to give the title compound as a white solid (1.124 g, 96%). MS(ES+) m/e 577 [M+H]+.

e) 2-{[(3-Amino-propyl)-(1-p-tolyl-methanoyl)-methyl-propyl}-1-benzyl-6-oxo-1,6-dihydro-pyrimidine-5-carboxlic acid phenylamide hydrochloride To a solution of 1-Benzyl-2-{[3-tert-butoxycarbonylamino-propyl)-(1-p-tolyl-methanoyl)-amino]-methylpropyl}-6-oxo-1,6-dihydro-pyrimidine-5-carboxylic acid (0.171 g, 0.297 mmol) in DMF (3 mL) were added EDCI (0.0568 g, 0.297 mmol), HOBt monohydrate (0.04 g, 0.297 mmol), and aniline (0.0276 g, 0.297 mmol) and the reaction was stirred at roon temperature for 24 h. The reaction was quenched with water, extracted into $CH_2Cl_2$, dried ($Na_2SO_4$), and concentrated. The resulting residue was stirred with excess 4M HCl in dioxane for 2 h at room temperature. The reaction was concentrated in vacuo, triturated with diethyl ether, and filtered to give the title compound as a tan solid (0.086 g, 50%, 2 steps). MS(ES+) m/e 552 [M+H]+.

Example 14

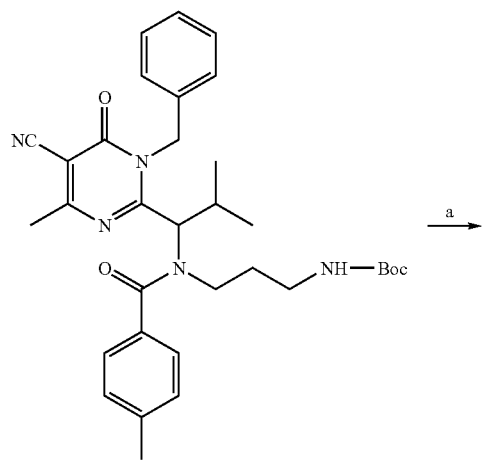

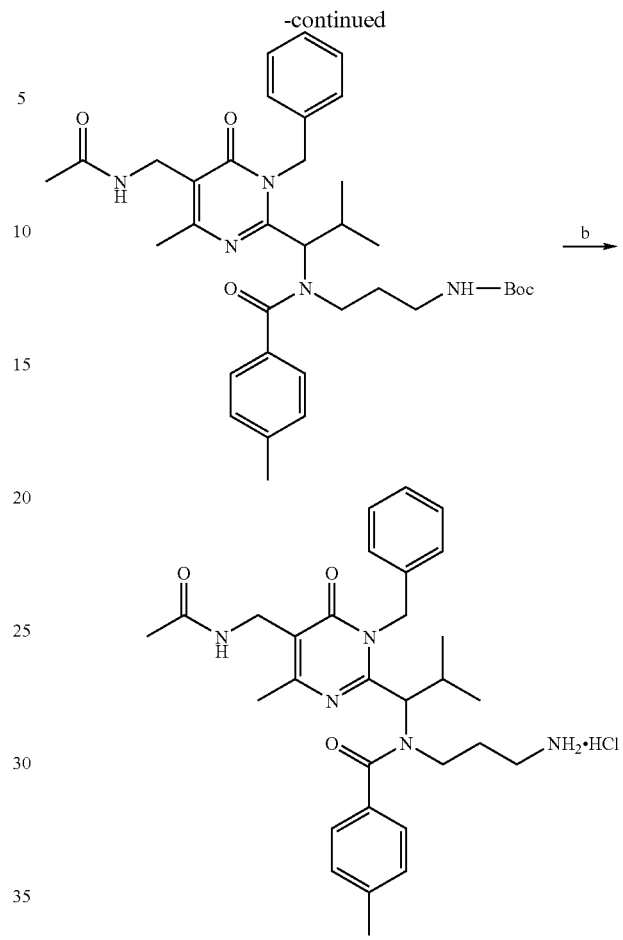

Conditions: a) $H_2$, 10% Pd/C, HOAc; $Ac_2O$, $Et_3N$, $CH_2Cl_2$ b) 4 N HCl, dioxane N-{1-[5-(Acetylamino-methyl)-3-benzyl-6-methyl-4-oxo-3,4-dihydro-pyrimidin-2-yl]-2-methyl-propyl}-N-(3-amino-propyl)-4-methyl-benzamide HCl salt a) {1-[{1-[5-(Acetylamino-methyl)-3-benzyl-6-methyl-4-oxo-3,4-dihydro-pyrimidin-2-yl]-2-methyl-propyl}-(1-p-tolyl-methanoyl)-amino]-propyl}-carbamic acid tert-butyl ester To a stirred solution of {1-[{1-[5-Cyano-3-benzyl-6-methyl-4-oxo-3,4-dihydro-pyrimidin-2-yl]-2-methyl-propyl}-(1-p-tolyl-methanoyl)-amino]-propyl}-carbamic acid tert-butyl ester (350 mg, 0.6 mMol) in HOAc (10 mL) was carefully added 10% Pd/C (150 mg). The reaction was hydrogenated under a balloon of $H_2$ for 18 h at RT, filtered through a pad of Celite®, rinsed with HOAc and evaporated under vacuum. To the crude amine (~34% pure by LCMS, MS (ES) m/e 576.4 (M+H)+) in $CH_2Cl_2$ (10 mL) was added with stirring $Et_3N$ (280 uL, 2 mMol) and $Ac_2O$ (114 uL, 1.2 mMol). After stirring at RT for 2 h the reaction was concentrated under vacuum, taken up in EtOAc, washed with 1 N $Na_2CO_3$, 1 N HCl, brine, dried ($MgSO_4$), filtered and evaporated under vacuum. Purification by flash chromatography (80% EtOAc/hexane) gave the title compound (0.10 g, 27%) as an off-white solid: MS (ES) m/e 618.4 (M+H)+.

b) N-{1-[5-(Acetylamino-methyl)-3-benzyl-6-methyl-4-oxo-3,4-dihydro-pyrimidin-2-yl]-2-methyl-propyl}-N-(3-amino-propyl)-4-methyl-benzamide HCl salt To {1-[{1-[5-(Acetylamino-methyl)-4-oxo-3,4-dihydro-pyrimidin-2-yl]-2-methyl-propyl}-(1-p-tolyl-methanoyl)-amino]-propyl}-carbamic acid tert-butyl ester (0.10 g, 0.16 mMol) was added a solution of 4 N HCl in dioxane (20 mL). The reaction was stirred for 1 h at RT then evaporated under vacuum. Trituration with Et₂O, filtration and drying under vacuum gave the title compound (54 mg, 61%) as an off-white solid: MS (ES) m/e 518.6 (M+H)⁺.

Example 15

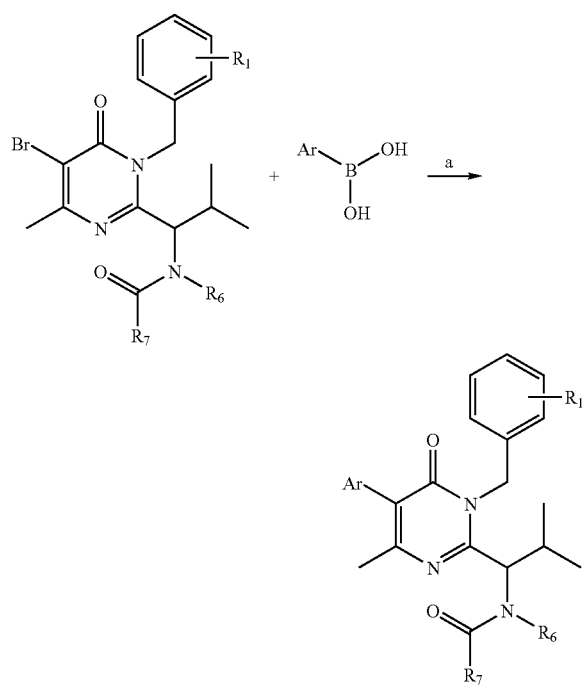

Conditions: a) Na₂CO₃, PdCl₂(PPh₃)₂, MeCN—H₂O, microwave, 5 min.

N-(3-Amino-propyl)-N-{(R)-1-[1-benzyl-5-(3-chloro-phenyl)-4-methyl-6-oxo-1,6-dihydro-pyrimidin-2-yl]-2-methyl-propyl}-4-methyl-benzamide a) N-(3-Amino-propyl)-N-{(R)-1'-[1-benzyl-5-(3-chloro-phenyl)-4-methyl-6-oxo-1,6-dihydro-pyrimidin-2-yl]-2-methyl-propyl}-4-methyl-benzamide A 10-mL Smith microwave reaction vial was charged with N-(3-amino-propyl)-N—[(R)-1-(1-benzyl-5-bromo-4-methyl-6-oxo-1,6-dihydro-pyrimidin-2-yl)-2-methyl-propyl]-4-methyl-benzamide (50 mg, 0.095 mmol), 3-chloroboronic acid (14.9 mg, 0.095 mmol), Na₂CO₃ (20.1 mg, 0.190 mmol), PdCl₂(PPh₃)₂ (3.3 mg, 0.005 mmol), followed by MeCN—H₂O (1:1, 0.4 mL). The mixture was purged with argon gas, sealed, and subjected to the microwave reactor for 5 min at 150° C. The residue was purified by reverse phase HPLC to give 27.5 mg (51%) of N-(3-amino-propyl)-N-{(R)-1'-[1-benzyl-5-(3-chloro-phenyl)-4-methyl-6-oxo-1,6-dihydro-pyrimidin-2-yl]-2-methyl-propyl}-4-methyl-benzamide as a yellow solid: MS (ES) m/e 557.4 (M+H)⁺.

Example 16

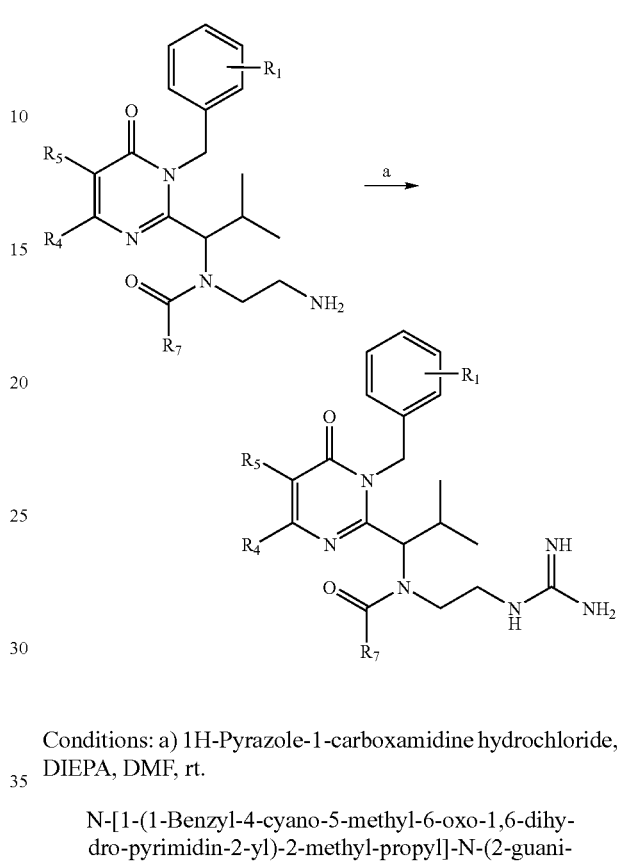

Conditions: a) 1H-Pyrazole-1-carboxamidine hydrochloride, DIEPA, DMF, rt.

N-[1-(1-Benzyl-4-cyano-5-methyl-6-oxo-1,6-dihydro-pyrimidin-2-yl)-2-methyl-propyl]-N-(2-guanidino-ethyl)-4-methyl-benzamide To a solution of N-[1-(1-benzyl-4-cyano-5-methyl-6-oxo-1,6-dihydro-pyrimidin-2-yl)-2-methyl-propyl]-N-(2-amino-ethyl)-4-methyl-benzamide (75 mg, 0.16 mMol) in DMF (1.5 mL) was added 1H-pyrazole-1-carboxamidine hydrochloride (25 mg, 0.17 mMol) and diisopropylethyl amine (57 µL, 0.33 mMol). The reaction was stirred at RT for 16 h, quenched with water (2 mL) and diluted with methylene chloride (2 mL). The aqueous layer was adjusted to pH 7 and extracted with methylene chloride (2×5 mL). The combined organic layers were dried (Na₂SO₄), filtered, and evaporated. Purification of the residue by reverse phase HPLC furnished the title compound (38 mg, 37%) as a white powder. MS (ES) m/e 500.4 (M+H)⁺.

Example 17

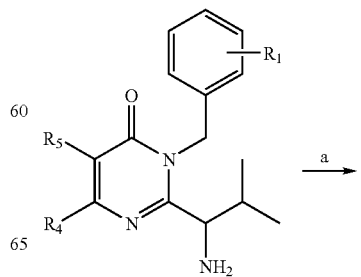

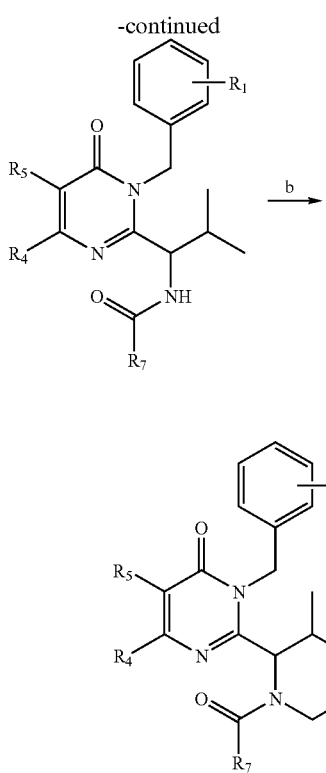

Conditions: a) R₇COCl, triethylamine, dichloromethane, ambient temperature; b) C₄H₈NCH₂CH₂Cl, sodium hydride, N,N-dimethylformamide, ambient temperature.

N—[(R)-1-(1-Benzyl-4,5-dimethyl-6-oxo-1,6-dihydro-pyrimidin-2-yl)-2-methyl-propyl]4-methyl-N-(2-pyrrolidin-1-yl-ethyl)-benzamide a) N—[(R)-1-(1-Benzyl-4,5-dimethyl-6-oxo-1,6-dihydro-pyrimidin-2-yl)-2-methyl-propyl]-4-methyl-benzamide To 2-((R)-1-amino-2-methyl-propyl)-3-benzyl-5,6-dimethyl-3H-pyrimidin-4-one (50 mg, 0.175 mMol) and triethylamine (49 µL, 0.350 mMol) in CH₂Cl₂ was add 4-methyl-benzoyl chloride (21 µL, 0.157 mMol) was added. The reaction was stirred at RT for 48 h, quenched with water and extracted with ethyl acetate (3×20 mL). The combined organic layers were dried (Na₂SO₄), filtered, and evaporated to give the title compound (50 mg, 72%) as colorless oil. MS (ES) m/e 404.2 (M+H)⁺.

b) N—[(R)-1-(1-Benzyl-4,5-dimethyl-6-oxo-1,6-dihydro-pyrimidin-2-yl)-2-methyl-propyl]-4-methyl-N-(2-pyrrolidin-1-yl-ethyl)-benzamide To N—[(R)-1-(1-benzyl-4,5-dimethyl-6-oxo-1,6-dihydro-pyrimidin-2-yl)-2-methyl-propyl]-4-methyl-benzamide (50 mg, 0.123 Mmol) in DMF was added sodium hydride (5 mg, 0.147 Mmol). The reaction stirred for 15 at RT then 1-(2-chloro-ethyl)-pyrrolidine (20 mg, 0.135 mmol) (Tilford et al.; J. Am. Chem. Soc.; 70; 1948; 4001). was added. The reaction was stirred at RT for 24 h, quenched with water and extracted with ethyl acetate (3×20 mL). The combined organic layers were washed with water (1×20 ml), brine (1×20 mL), dried (Na₂SO₄), filtered, and evaporated to yield the title compound (30 mg, 49%) as a colorless oil: MS (ES) m/e 501.4 (M+H)⁺.

Example 18

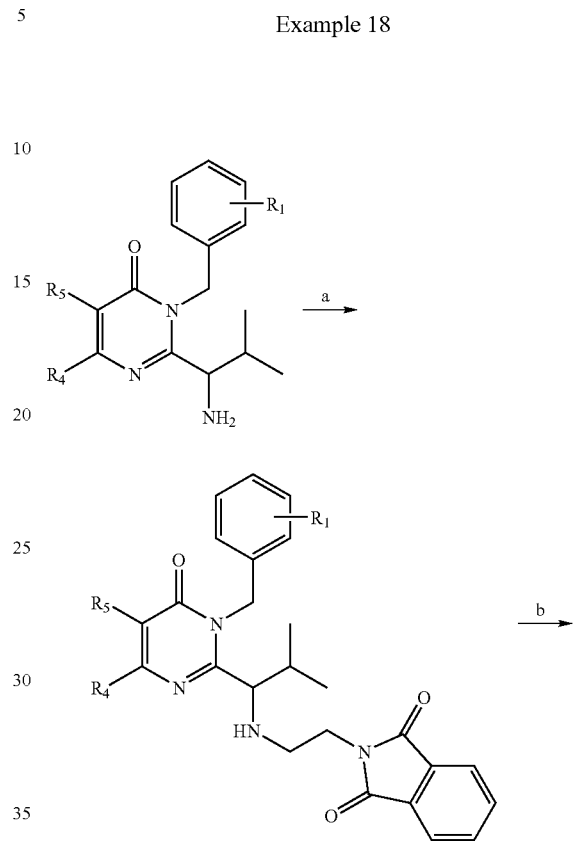

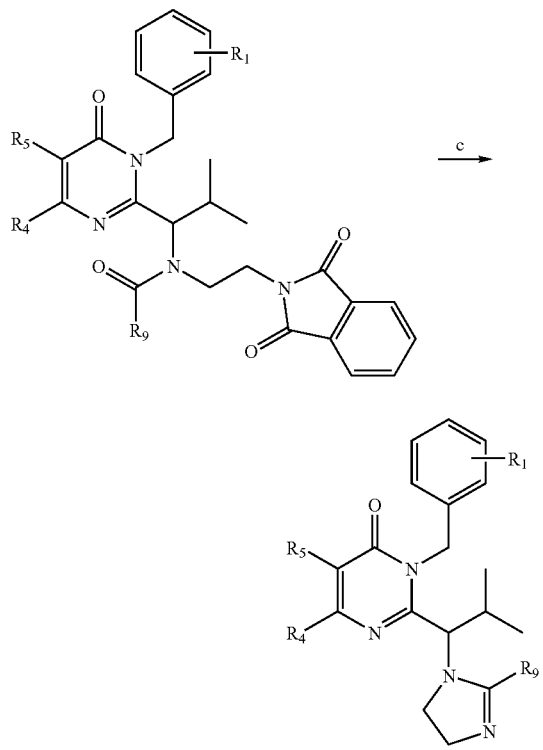

Conditions: a) NaBH(AcO)$_3$, AcOH, DCE, rt; b) R$_9$COCl, DIEPA, toluene, 100° C.; c) hydrazine, EtOH, 70° C.

3-Benzyl-5,6-dimethyl-2-[(R)-2-methyl-1-(2-p-tolyl-4,5-dihydro-imidazol-1-yl)-propyl]-3H-pyrimidin-4-one a) 2-{2-[(R)-1-(1-Benzyl-4,5-dimethyl-6-oxo-1,6-dihyro-pyrimidin-2-yl)-2-methyl-propylamino]-ethyl}-isoindole-1,3-dione 2-((R)-1-Amino-2-methyl-propyl)-3-benzyl-5,6-dimethyl-3-H-pyrimidin-4-one (0.500 g, 1.75 mMol) and 2H-isoindole-2-acetaldehyde [2913-97-5] (0.661 g, 3.50 mMol) were dissolved in dichloroethane (20 mL). Glacial acetic acid was added (0.400 mL, 0.70 mMol) followed by sodium triacetoxy borohydride (0.942 g, 4.40 mMol). The reaction stirred at room temperature under nitrogen for 3.5 h. The reaction was quenched with NaHCO$_3$ (sat. Aq.) and extracted with EtOAc (3×). The organic layer was evaporated under reduced pressure and purified by flash chromatography. (EtOAc/hexane 50-95% gradient) to give the title compound 420 mg (0.92 mMol) MS (ES) m/e 459 (M+H)$^+$.

b) N—[(R)-1-(1-Benzyl-4,5-dimethyl-6-oxo-1,6-dihyro-pyrimidin-2-yl)-2-methyl-propyl]-N-[2(1,3-dioxo-1,3-dihydro-isoindol-2-yl-ethyl]-4-methyl-benzamide p-Toluoyl chloride (0.033 mL, 0.25 mMol) was dissolved in toluene (2 mL) and was treated with DIPEA (0.093 mL, 0.53 mMol) followed by 2-{2-[(R)-1-(1-benzyl-4,5-dimethyl-6-oxo-1,6-dihyro-pyrimidin-2-yl)-2-methyl-propylamino]-ethyl}-isoindole-1,3-dione (0.100 g, 0.22 mMol) The reaction stirred at 110° C. for 3 h. The reaction was cooled to room temperature and was evaporated under reduced pressure and purified by flash chromatography. (EtOAc/hexane 0-55% gradient) to give the title compound 0.075 g (0.13 mMol) MS (ES) m/e 577 (M+H)$^+$.

c) 3-Benzyl-5,6-dimethyl-2-[(R)-2-methyl-1-(2-p-tolyl-4,5-dihydro-imidazol 1-yl)-propyl]-3H-pyrimidin-4-one The phthalimide protected amine, N—[(R)-1-(1-benzyl-4,5-dimethyl-6-oxo-1,6-dihyro-pyrimidin-2-yl)-2-methyl-propyl]-N-[2-(1,3-dioxo-1,3-dihydro-isoindol-2-yl)-ethyl]-4-methyl-benzamide, (0.075 g, 0.13 mMol) was treated with hydrazine monohydrate (0.013 mL, 0.26 mMol) in ethanol (1 mL) at 70° C. for 12 h. The reaction was filtered, concentrated under vacuum and dissolved in toluene (1 mL) and heated to 120° C. for 20 h. The reaction was concentrated under vacuum, taken up in CH$_3$CN and purified by reverse phase HPLC (YMC, ODS-A, 20 min, 5-90% gradient, CH$_3$CN:H$_2$O, 0.1% TFA) The fractions were collected and evaporated to give the title compound as a clear oil. (0.016 g): MS (ES) m/e 429.4 (M+H)$^+$.

Example 19

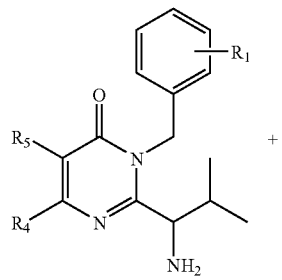

+

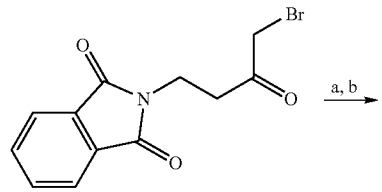

-continued

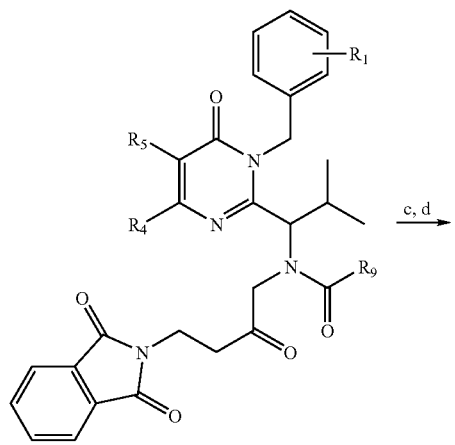

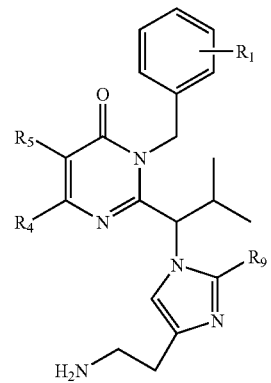

Conditions: a) DIPEA, DMF, rt; b) R$_9$COCl, Et$_3$N, CH$_2$Cl$_2$, rt; c) NH4OAc, AcOH, reflux; d) hydrazine, EtOH, rt.

2-{1-[4-(2-Amino-ethyl)-2-p-tolyl-imidazol-1-yl]-2-methyl-propyl}-3-benzyl-5,6-dimethyl-3H-pyrimidin-4-one a) 2-{4-[1-(1-Benzyl-4,5-dimethyl-6-oxo-1,6-dihydro-pyrimidin-2-yl)-2-methyl-propylamino]-3-oxo-butyl}-isoindole-1,3-dione To 2-(1-Amino-2-methyl-propyl)-3-benzyl-5,6-dimethyl-3H-pyrimidin-4-one (0.66 g, 2.33 mmol) in DMF (15 mL)was added 2-(4-bromo-3-oxo-butyl)-isoindole-1,3-dione (0.69 g, 2.33 mmol, prepared as described in WO 89/10360) and N,N-diisopropylethylamine (0.301 g, 2.33 mmol). The reaction was stirred for 16 h at room temperature, concentrated under vacuum, dissolved in EtOAc/H₂O, washed with water, dried (Na₂SO₄), and evaporated to give the title compound as a white foam (1.04 g, 89%). MS(ES+) m/e 501 [M+H]⁺.

b) N-[1-(1-Benzyl-4,5-dimethyl-6-oxo-1,6-dihydro-pyrimidin-2-yl)-2-methyl-propyl]-N-[4-(1,3-dioxo-1,3-dihydro-isoindol-2-yl)-2-oxo-butyl]-4-methyl-benzamide To 2-{4-[1-(1-Benzyl-4,5-dimethyl-6-oxo-1,6-dihydro-pyrimidin-2-yl)-2-methyl-propylamino]-3-oxo-butyl}-isoindole-1,3-dione (1.024 g, 2.046 mmol) in CH₂Cl₂ (14 mL) was added triethylamine (0.31 g, 3.069 mmol) and p-toluoyl chloride (0.474 g, 3.069 mmol). The reaction was stirred for 16 h at room temperature, washed with water, dried (Na₂SO₄), and evaporated to dryness. The residue was purified by flash chromatography on silica gel (1:1 hexanes:EtOAc) to give the title compound as a white foam (0.885 g, 70%). MS(ES+) m/e 619 [M+H]⁺.

c) 2-(2-{1-[1-(1-Benzyl-4,5-dimethyl-6-oxo-1,6-dihydro-pyrimidin-2-yl)-2-methyl-propyl]-2-p-tolyl-1H-imidazol-4-yl}-ethyl)-isoindole-1,3-dione To N-[1-(1-Benzyl-4,5-dimethyl-6-oxo-1,6-dihydro-pyrimidin-2-yl)-2-methyl-propyl]-N-[4-(1,3-dioxo-1,3-dihydro-isoindol-2-yl)-2-oxo-butyl]-4-methyl-benzamide (0.884 g, 1.62 mmol) in glacial acetic acid (15 mL) was added ammonium acetate (6.22 g, 80.8 mmol) and the reaction was heated at reflux for 16 h. The reaction was concentrated in vacuo and the residue was basified with saturated NaHCO₃, extracted into EtOAc, washed with water and brine, dried (Na₂SO₄), and evaporated to dryness. The residue was purified by flash chromatography on silica gel (3:1 EtOAc:hexanes) to give the title compound as a pale yellow foam (0.371 g, 38%). MS(ES+) m/e 600 [M+H]⁺.

d) 2-{1-[4-(2-Amino-ethyl)-2-p-tolyl-imidazol-1-yl]-2-methyl-propyl}-3-benzyl-5,6-dimethyl-3H-pyrimidin-4-one To 2-(2-{1-[1-(1-Benzyl-4,5-dimethyl-6-oxo-1,6-dihydro-pyrimidin-2-yl)-2-methyl-propyl]-2-p-tolyl-1H-imidazol-4-yl}-ethyl)-isoindole-1,3-dione (0.371 g, 0.619 mmol) in EtOH (14 mL) was added hydrazine monohydrate (0.138 g, 2.48 mmol) and the reaction was stirred at room temperature for 72 h. The reaction was filtered and the filtrate was concentrated to dryness. The residue was purified by flash chromatography on silica gel (90:9:1 CH₂Cl₂:MeOH:NH₄OH) to give the title compound as a white solid (0.209 g, 72%). MS(ES+)m/e 470 [M+H]⁺.

Example 20

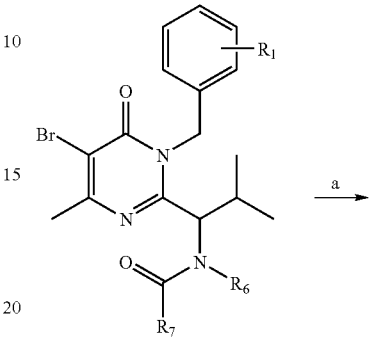

a →

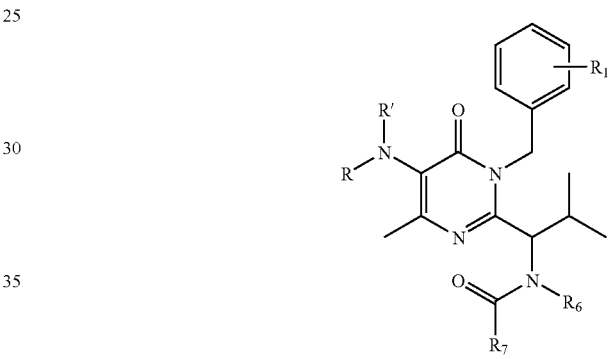

Conditions: a) RR'NH, sodium t-butoxide, Pd₂ dba₃, (S)-BINAP, CH₃CN, 90° C.

N-(3-amino-propyl)-N-{(R)-1-[1-benzyl-4-methyl-6-oxo-5-phenylamino-1,6-dihydro-pyrimidin-2-yl]-2-methyl-propyl}-4-methyl benzamide To N-(3-amino-propyl)-N-{(R)-1-[1-benzyl-5-Br-4-yl-6-oxo-1,6-dihydro-pyrimidin-2-yl]-2-methyl-propyl}-4-methyl benzamide (0.060 g, 0.1 mMol) in toluene (0.30 mL). was added aniline, (0.011 mL, 0.12 mMol), NaO-tBu (0.013 g, 0.14 mmol), Pd₂ DBA (0.003 g, 0.0003 mmol), and (S)-BINAP (0.005 g, 0.0008 mmol) The reaction was stirred at 90° C. for 72 h, concentrated under vacuum, taken up in CH₃CN and purified by reverse phase HPLC (YMC, ODS-A, 20 min, 5-90% gradient, CH₃CN:H₂O, 0.1% TFA) The fractions were collected and evaporated and treated with 4N HCl/dioxane for 1 h and purified by reverse phase HPLC (YMC, ODS-A, 20 min, 5-90% gradient, CH₃CN: H₂O, 0.1% TFA) and evaporated to give the title compound as a clear semi-solid. (0.008 g): MS (ES) m/e 538 (M+H)⁺.

Example 21

The following compounds were prepared by the method indicated:

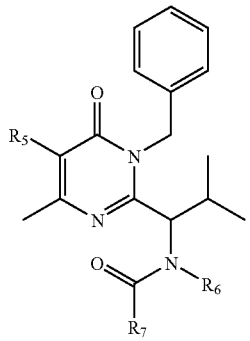

| Method | $R_5$ | $R_6$ | $R_7$ | $[M + H]^+$ |
|---|---|---|---|---|
| 15 | 3-Cl—Ph | —(CH$_2$)$_3$NH$_2$ | 4-Me—Ph— | 557.4 |
| 15 | 4-Cl—Ph | —(CH$_2$)$_3$NH$_2$ | 4-Me—Ph— | 557.2 |
| 15 | 3-F—Ph | —(CH$_2$)$_3$NH$_2$ | 4-Me—Ph— | 541.4 |
| 15 | 3-CF$_3$—Ph | —(CH$_2$)$_3$NH$_2$ | 4-Me—Ph— | 591.2 |
| 15 | 3-NHAc—Ph | —(CH$_2$)$_3$NH$_2$ | 4-Me—Ph— | 580.6 |
| 15 | 3-MeO—Ph | —(CH$_2$)$_3$NH$_2$ | 4-Me—Ph— | 553.4 |
| 15 | 3-CN—Ph | —(CH$_2$)$_3$NH$_2$ | 4-Me—Ph— | 548.4 |
| 15 | 4-Me$_2$N—Ph | —(CH$_2$)$_3$NH$_2$ | 4-Me—Ph— | 552.4 |
| 15 | 3,4-diF—Ph | —(CH$_2$)$_3$NH$_2$ | 4-Me—Ph— | 559.4 |
| 15 | 3-EtO—Ph | —(CH$_2$)$_3$NH$_2$ | 4-Me—Ph— | 567.4 |
| 15 | 4-EtO—Ph | —(CH$_2$)$_3$NH$_2$ | 4-Me—Ph— | 567.4 |
| 15 | 4-F—Ph | —(CH$_2$)$_3$NH$_2$ | 4-Me—Ph— | 541.4 |
| 15 | 2-furyl | —(CH$_2$)$_3$NH$_2$ | 4-Me—Ph— | 513.4 |
| 15 | 3-thiophenyl | —(CH$_2$)$_3$NH$_2$ | 4-Me—Ph— | 529.2 |
| 15 | 3-Me—Ph | —(CH$_2$)$_3$NH$_2$ | 4-Me—Ph— | 537.4 |
| 15 | 4-Me—Ph | —(CH$_2$)$_3$NH$_2$ | 4-Me—Ph— | 537.2 |
| 15 | 3,4-(OCH$_2$O)—Ph | —(CH$_2$)$_3$NH$_2$ | 4-Me—Ph— | 567.4 |
| 15 | 3-NH$_2$—Ph | —(CH$_2$)$_3$NH$_2$ | 4-Me—Ph— | 538.4 |
| 15 | 1-naphthyl | —(CH$_2$)$_3$NH$_2$ | 4-Me—Ph— | 573.4 |
| 15 | 4-MeO—Ph | —(CH$_2$)$_3$NH$_2$ | 4-Me—Ph— | 553.4 |
| 15 | 4-MeS—Ph | —(CH$_2$)$_3$NH$_2$ | 4-Me—Ph— | 569.2 |
| 15 | 2-Me—Ph | —(CH$_2$)$_3$NH$_2$ | 4-Me—Ph— | 537.4 |
| 15 | 2-MeO—Ph | —(CH$_2$)$_3$NH$_2$ | 4-Me—Ph— | 553.6 |
| 15 | 2-F—Ph | —(CH$_2$)$_3$NH$_2$ | 4-Me—Ph— | 541.2 |
| 15 | 2-EtO—Ph | —(CH$_2$)$_3$NH$_2$ | 4-Me—Ph— | 567.4 |
| 15 | 4-HOCH$_2$—Ph | —(CH$_2$)$_3$NH$_2$ | 4-Me—Ph— | 553.4 |
| 15 | 3,4-diMe—Ph | —(CH$_2$)$_3$NH$_2$ | 4-Me—Ph— | 551.2 |
| 15 | 3,4-diMeO—Ph | —(CH$_2$)$_3$NH$_2$ | 4-Me—Ph— | 583.4 |
| 15 | 2-NH$_2$-4-Me—Ph | —(CH$_2$)$_3$NH$_2$ | 4-Me—Ph— | 552.6 |
| 15 | 3-HOCH$_2$—Ph— | —(CH$_2$)$_3$NH$_2$ | 4-Me—Ph— | 553.4 |
| 15 | 3,5-diF—Ph— | —(CH$_2$)$_3$NH$_2$ | 4-Me—Ph— | 559.4 |
| 15 | 4-CN—Ph— | —(CH$_2$)$_3$NH$_2$ | 4-Me—Ph— | 548.4 |
| 15 | 2,4-diF—Ph— | —(CH$_2$)$_3$NH$_2$ | 4-Me—Ph— | 559.4 |
| 15 | 3-furyl- | —(CH$_2$)$_3$NH$_2$ | 4-Me—Ph— | 513.4 |
| 15 | 5-indolyl- | —(CH$_2$)$_3$NH$_2$ | 4-Me—Ph— | 562.2 |
| 15 | 2,3-diF—Ph— | —(CH$_2$)$_3$NH$_2$ | 4-Me—Ph— | 559.2 |
| 15 | 2,5-diF—Ph— | —(CH$_2$)$_3$NH$_2$ | 4-Me—Ph— | 559.4 |
| 15 | 2,5-diMe—Ph— | —(CH$_2$)$_3$NH$_2$ | 4-Me—Ph— | 551.4 |
| 15 | 4-F-3-Me—Ph— | —(CH$_2$)$_3$NH$_2$ | 4-Me—Ph— | 554.2 |
| 12 | —CONHEt | —(CH$_2$)$_3$NH$_2$ | 4-Me—Ph— | 518.4 |
| 12 | —CONHMe | —(CH$_2$)$_3$NH$_2$ | 4-Me—Ph— | 504.4 |
| 12 | —CO-morpholinyl | —(CH$_2$)$_3$NH$_2$ | 4-Me—Ph— | 560.4 |
| 12 | —CONHBn | —(CH$_2$)$_3$NH$_2$ | 4-Me—Ph— | 580.6 |
| 12 | —CONH(CH$_2$)$_2$NHAc | —(CH$_2$)$_3$NH$_2$ | 4-Me—Ph— | 575.4 |
| 12 | —CONH(CH$_2$)$_2$OMe | —(CH$_2$)$_3$NH$_2$ | 4-Me—Ph— | 548.2 |
| 20 | —N-morpholinyl | —(CH$_2$)$_3$NH$_2$ | 4-Me—Ph— | 532 |
| 12 | —CONHPh | —(CH$_2$)$_3$NH$_2$ | 4-Me—Ph— | 566.4 |
| 12 | —CONH(CH$_2$)$_2$OH | —(CH$_2$)$_3$NH$_2$ | 4-Me—Ph— | 534.4 |
| 12 | —COOH | —(CH$_2$)$_3$NH$_2$ | 4-Me—Ph— | 491.4 |
| 05 | Me | —(CH$_2$)$_3$NH$_2$ | 4-MeO—Ph— | 477.2 |
| 05 | Me | —(CH$_2$)$_3$NH$_2$ | 3-(5-methyl-isoxazole)- | 452.4 |
| 05 | Me | —(CH$_2$)$_3$NH$_2$ | 5-benzo[1,2,3]thiadiazole- | 505.2 |
| 05 | Me | —(CH$_2$)$_3$NH$_2$ | 6-methyl-nicotinamide- | 462.4 |
| 05 | Me | —(CH$_2$)$_3$NH$_2$ | 2-(5-methyl-pyrazine)- | 463.4 |

-continued

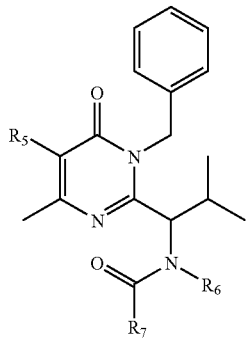

| Method | $R_5$ | $R_6$ | $R_7$ | $[M + H]^+$ |
|---|---|---|---|---|
| 05 | Me | —(CH$_2$)$_3$NH$_2$ | 4-CN—Ph— | 472.4 |
| 05 | Me | —(CH$_2$)$_3$NH$_2$ | MeOCH$_2$— | 415.6 |
| 05 | Me | —(CH$_2$)$_3$NH$_2$ | 5-benzo[1,3]dioxole- | 491.4 |
| 05 | Me | —(CH$_2$)$_3$NH$_2$ | 2-(5-methyl-thiophene)- | 467.2 |
| 05 | Et | —(CH$_2$)$_3$NH$_2$ | 4-MePh— | 475 |
| 05 | Et | —(CH$_2$)$_3$NH$_2$ | 3-F-4-MePh— | 493 |
| 05 | Et | —(CH$_2$)$_3$NH$_2$ | 3-(6-methyl-pyridyl)- | 476 |
| 09, 05 | —CN | —(CH$_2$)$_3$NH$_2$ | 3-F-4-MePh— | 490.4 |
| 09, 05 | —CN | —(CH$_2$)$_3$NH$_2$ | 3,4-diMeO—Ph— | 518.4 |
| 09, 05 | —CN | —(CH$_2$)$_3$NH$_2$ | 3-Me—Ph— | 472.4 |
| 09, 05 | —CN | —(CH$_2$)$_3$NH$_2$ | 4-Et—Ph— | 486.4 |
| 09, 05 | —CN | —(CH$_2$)$_3$NH$_2$ | 4-CF$_3$O—Ph— | 542.2 |
| 09, 05 | —CN | —(CH$_2$)$_3$NH$_2$ | 4-F-3-Me—Ph— | 490.4 |
| 09, 05 | —CN | —(CH$_2$)$_3$NH$_2$ | 4-F-3-CF$_3$—Ph— | 544.2 |
| 09, 05 | —CN | —(CH$_2$)$_3$NH$_2$ | 3-F-4-CF$_3$—Ph— | 544.2 |
| 09, 05 | —CN | —(CH$_2$)$_3$NH$_2$ | 3-Cl—Ph— | 492.2 |
| 09, 05 | —CN | —(CH$_2$)$_3$NH$_2$ | 4-CF$_3$—Ph— | 526.4 |
| 09, 05 | —CN | —(CH$_2$)$_3$NH$_2$ | 4-F—Ph— | 476.2 |
| 09, 05 | —CN | —(CH$_2$)$_3$NH$_2$ | 4-Cl—Ph— | 492.2 |
| 09, 05 | —CN | —(CH$_2$)$_3$NH$_2$ | 3,4-diF—Ph— | 494.2 |
| 09, 05 | —CN | —(CH$_2$)$_3$NH$_2$ | 3-CN—Ph— | 483.2 |
| 09, 05 | —CN | —(CH$_2$)$_3$NH$_2$ | 4-Br—Ph— | 536.2 |
| 09, 05 | —CN | —(CH$_2$)$_3$NH$_2$ | 3-F—Ph— | 476.2 |
| 09, 05 | —CN | —(CH$_2$)$_3$NH$_2$ | 3-Cl-4-F—Ph— | 510.2 |
| 09, 05 | —CN | —(CH$_2$)$_3$NH$_2$ | 4-HOCH$_2$—Ph— | 488.2 |
| 05 | Me | —CH$_2$(4-piperidinyl) | 4-Me—Ph— | 501.4 |
| 05 | Me | —CH$_2$(3-piperidinyl) | 4-Me—Ph— | 501.4 |
| 05 | Me | —CH$_2$(2-pyrolidinyl) | 4-Me—Ph— | 487.4 |
| 05 | Me | —CH$_2$(3-azetidinyl) | 4-Me—Ph— | 473.4 |
| 05 | Me | —CH$_2$(3-azetidinyl) | 4-HOCH$_2$—Ph— | 489.4 |

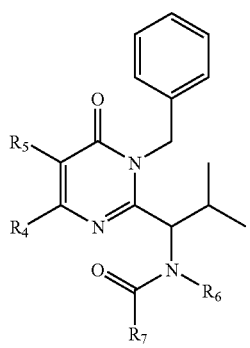

| Method | $R_5$ | $R_4$ | $R_6$ | $R_7$ | $[M + H]^+$ |
|---|---|---|---|---|---|
| 11, 05 | Me | —CN | —(CH$_2$)$_3$NH$_2$ | 3-F-4-MePh— | 490.2 |
| 11, 05 | Me | —CN | —(CH$_2$)$_3$NH$_2$ | 3-F—Ph— | 476.2 |

-continued

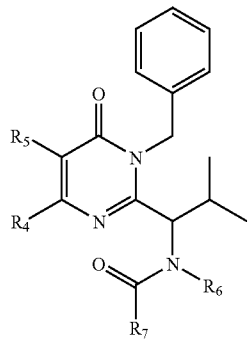

| Method | R₅ | R₄ | R₆ | R₇ | [M + H]⁺ |
|---|---|---|---|---|---|
| 11, 05 | Me | —CN | —(CH₂)₃NH₂ | 4-F—Ph— | 476.2 |
| 11, 05 | Me | —CN | —(CH₂)₃NH₂ | 3-Cl—Ph— | 492.2 |
| 11, 05 | Me | —CN | —(CH₂)₃NH₂ | 3-F-4-CF₃—Ph— | 544.2 |
| 11, 05 | Me | —CN | —(CH₂)₃NH₂ | 4-CF₃O—Ph— | 542.2 |
| 11, 05 | Me | —CN | —(CH₂)₃NH₂ | 4-CF₃—Ph— | 526.2 |
| 11, 05 | Me | —CN | —(CH₂)₃NH₂ | 4-Et—Ph— | 486.4 |
| 11, 05 | Me | —CN | —(CH₂)₃NH₂ | 3,4-diMeO—Ph— | 518.4 |
| 11, 05 | Me | —CN | —(CH₂)₃NH₂ | 3,4-diF—Ph— | 494.4 |
| 11, 05 | Me | —CN | —(CH₂)₃NH₂ | 3-CN—Ph— | 483.2 |
| 05 | Me | —CF₃ | —(CH₂)₃NH₂ | 4-MePh— | 515 |
| 05 | Me | —CF₃ | —(CH₂)₃NH₂ | 3-F-4-MePh— | 533 |
| 05 | Me | —CF₃ | —(CH₂)₃NH₂ | 3-(6-methyl-pyridyl)- | 516 |
| 13 | —CONHMe | H | —(CH₂)₃NH₂ | 4-Me—Ph— | 490 |
| 13 | —CONHBn | H | —(CH₂)₃NH₂ | 4-Me—Ph— | 566 |
| 13 | —CONH(CH₂)₂OH | H | —(CH₂)₃NH₂ | 4-Me—Ph— | 520 |
| 13 | —CONHC₃H₅ | H | —(CH₂)₃NH₂ | 4-Me—Ph— | 516 |
| 11, 05 | Me | —CN | —(CH₂)₂NH₂ | 4-Me—Ph— | 458.4 |
| 11, 05 | Me | —CN | —(CH₂)₂NHC(NH)NH₂ | 4-Me—Ph— | 500.4 |
| 05 | —(CH₂)₃— | | —(CH₂)₃NH₂ | 3-F-4-Me—Ph— | 491.4 |
| 15 | Ph— | H | —(CH₂)₃NH₂ | 4-Me—Ph— | 509.4 |

| Method | R₁ | R₇ | [M + H]⁺ |
|---|---|---|---|
| 05 | 3-cyanobenzyl- | 6-methyl-nicotinamide- | 487.4 |
| 05 | 3-cyanobenzyl- | 4-Me—Ph— | 486.2 |
| 05 | 3-methoxybenzyl- | 4-Me—Ph— | 491.4 |

| Method | R₄ | R₉ | [M + H]⁺ |
|---|---|---|---|
| 18 | —CN | 4-MePh— | 440.4 |
| 18 | Me | 2-(5-methyl-thiophene)- | 435.5 |

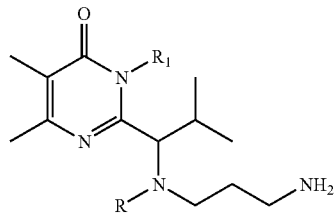

| Method | $R_1$ | R | $[M+H]^+$ |
|---|---|---|---|
| 05 | Benzyl- | —$SO_2$(4-MePh) | 497.4 |
| 05 | Naphthalenylmethyl- | —$COCH_2$OMe | 465.2 |

Example 22

Inhibition of Cellular Viability in Tumor Cell Lines Treated with KSP Inhibitors.r Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.

Procedure: Day 1—Cell Plating:

Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+ 5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C., 100% humidity, and 5% $CO_2$, allowing the cells to adhere to the plates.

Procedure: Day 2—Compound Addition:

To one column of the wells of an autoclaved assay block are added an initial 2.5 µL of test compound(s) at 400× the highest desired concentration. 1.25 µL of 400× (400 µM) Topotecan is added to other wells (optical density's from these wells are used to subtract out for background absorbance of dead cells and vehicle). 500 µL of media without DMSO are added to the wells containing test compound, and 250 µL to the Topotecan wells. 250 µL of media+0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:

The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis

The normalized % of control (absorbance-background) is calculated and an XLfit is used to generate a dose-response curve from which the concentration of compound required to inhibit viability by 50% is determined. The compounds of the present invention show activity when tested by this method as described above.

Example 23

Enantiomer Separation

In general, the procedures described above can be used to prepare substantially pure or enriched R- or S-enantiomers by selected a starting amino acid of the appropriate R- or S-configuration. More preferred compounds of the invention are those of the R-configuration at the stereogenic center to which $R^2$ is attached. An R:S mixture can be separated into its constituent pure enantiomers by methods well known to those skilled in the art. These include the formation and separation of diastereomeric derivatives such as those formed by reaction with an optically pure acid such as dibenzoyltartaric acid. Alternatively, separation can be accomplished by chiral chromatography, for example, using the following conditions:

Column: Chiralcel OD 20×250 mm;
Sample loaded ~100 mg $mL^{-1}$ in 1:2 ethanol:hexane containing 0.01% isopropylamine;
Chromatography conditions: isocratic elution with 1:2 ethanol:hexane containing 0.01% isopropylamine at a flow rate of 15 mL $min^-$;
UV detection at 254 nm.

For example, an enriched 3:1 R:S mixture of enantiomers was separated into its pure enantiomers by chiral chromatography with the following conditions: Chiralpak AD, 250×4.6 mm (Diacel Inc.). Sample—22.5 mg/ml in 1:1 i-PrOH:hexanes. Conditions—40 min at isocratic 50% i-PrOH in Hexanes, (S)-enantiomer elutes at 18.35 min, (R)-enantiomer elutes at 26.87 min. The (R)-enantiomer was significantly more potent than the (S)-enantiomer.

Example 24

Monopolar Spindle Formation following Application of a KSP Inhibitor

Human tumor cells Skov-3 (ovarian) were plated in 96-well plates at densities of 4,000 cells per well, allowed to adhere for 24 hours, and treated with various concentrations of the pyridmidinone derivatives for 24 hours. Cells were fixed in 4% formaldehyde and stained with antitubulin antibodies (subsequently recognized using fluorescently-labeled secondary antibody) and Hoechst dye (which stains DNA).

Visual inspection revealed that the compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Example 25

Inhibition of Cellular Proliferation in Tumor Cell Lines Treated with KSP Inhibitors.

Cells were plated in 96-well plates at densities from 1000-2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (Patent No. 5,185,450) (see Promega product catalog #G3580, Cell-Titer 96® AQ$_{ueous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this.

A $Gi_{50}$ was calculated by plotting the concentration of compound in μM vs the percentage of cell growth in treated wells. The $Gi_{50}$ calculated for the compounds is the estimated concentration at which growth is inhibited by 50% compared to control, i.e., the concentration at which:

$$100 \times [(\text{Treated}_{48} - T_0)/(\text{Control}_{48} - T_0)] = 50$$

wherein $\text{Treated}_{48}$ is the value at 48 hours for the treated cells and $\text{Control}_{48}$ is the value at 48 hours for the control population.

All concentrations of compounds are tested in duplicate and controls are averaged over 12 wells. A very similar 96-well plate layout and $Gi_{50}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Compounds of Examples 1-13 above inhibited cell proliferation in human ovarian tumor cell lines (SKOV-3).

Example 26

Calculation of $IC_{50}$:

Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 μg/ml microtubules, 1 mM DTT (Sigma D9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT4003-01), and 1 mM EGTA (Sigma E3889). Serial dilutions (8-12 two-fold dilutions) of the compound are made in a 96-well microtiter plate (Corning Costar 3695) using Solution 1. Following serial dilution each well has 50 μl of Solution 1. The reaction is started by adding 50 μl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1 + \left(\frac{x}{IC_{50}}\right)^s} + \text{Background}$$

where y is the observed rate and x is the compound concentration.

What is claimed is:

1. A method of inhibiting KSP which comprises contacting KSP in vitro with an effective amount of a compound having the structure:

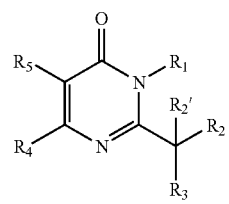

wherein:
 $R_1$ is chosen from optionally substituted phenyl-$C_1$-$C_4$-alkyl-, optionally substituted heteroaryl-$C_1$-$C_4$-alkyl-, and naphthalenylmethyl-;
 $R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_{2'}$ taken together form a 3- to 7-membered ring;
 $R_4$ is chosen from hydrogen; alkoxy; cyano; carboxamido; aminocarbonyl-; lower-alkyl-; lower-alkyl substituted with one or more of the following substituents: halo, lower-alkoxy, or hydroxy; phenyl-; or phenyl substituted with one or more of the following substituents: halo, lower-alkoxy, and hydroxy;
 $R_5$ is chosen from hydrogen; carboxamido, cyano; lower-alkyl; halo; benzyl-; naphthyl-; furyl-; thienyl-; indolyl-; phenyl-; and phenyl substituted with one or more of the following substituents: optionally substituted amino, dialkylamino, cyano, halo, optionally substituted lower-alkyl-, optionally substituted lower-alkoxy, optionally substituted lower-alkyl sulfanyl, hydroxy, and thio;
 $R_3$ is —N($R_6$)(CO$R_7$);
 $R_7$ is chosen from hydrogen, optionally substituted alkyl-, optionally substituted aryl-, optionally substituted aralkyl-, optionally substituted heteroaryl-, optionally substituted heteroaralkyl-, $R_8$O— and $R_{14}$—NH—;
 $R_6$ is chosen from hydrogen, optionally substituted alkyl-, optionally substituted aryl-, optionally substituted aralkyl-, optionally substituted heteroaryl-, and optionally substituted heteroaralkyl-;
 $R_8$ is chosen from optionally substituted alkyl-, optionally substituted aryl-, optionally substituted aralkyl-, optionally substituted heteroaryl-, and optionally substituted heteroaralkyl-, and
 $R_{14}$ is optionally substituted alkyl-, optionally substituted aryl-, optionally substituted aralkyl-, optionally substituted heteroaryl-, or optionally substituted heteroaralkyl-; or
a pharmaceutically acceptable salt thereof;
wherein "substituted" alkyl, aryl and heteroaryl refer respectively to alkyl, aryl and heteroaryl wherein one or more hydrogen atoms are replaced by a substituent independently chosen from optionally substituted alkyl, optionally substituted alkoxy, alkylenedioxy, optionally substituted amino, optionally substituted amidino, optionally substituted aryl, optionally substituted aralkyl, optionally substituted aryloxy, optionally substituted aralkoxy, carboxy, carboalkoxy, carboxyalkyl, carboxamido, aminocarbonyl, benzyloxycarbonylamino, cyano, acyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

2. A method according to claim 1 wherein $R_1$ is phenethyl-, benzyl-, chlorobenzyl-, methylbenzyl-, methoxybenzyl-, cyanobenzyl-, hydroxybenzyl-, dichlorobenzyl-, dimethoxybenzyl-, or naphthalenylmethyl-.

3. A method according to claim 1 wherein $R_2$ is chosen from methyl-, ethyl-, propyl-, butyl-, methylthioethyl-, methyithiomethyl-, aminobutyl-, (CBZ)aminobutyl-, cyclohexylmethyl-, benzyloxymethyl-, methylsulfinylethyl-, methylsulfinylmethyl-, and hydroxymethyl-, and $R_{2'}$ is hydrogen.

4. A method according to claim 1 wherein $R_{2'}$ is hydrogen and $R_2$ is ethyl or propyl.

5. A method according to claim 1 wherein $R_2$ is i-propyl.

6. A method according to claim 1 wherein if either $R_2$ or $R_{2'}$ is hydrogen, then the other is not hydrogen.

7. A method according to claim 1 wherein both $R_2$ and $R_{2'}$ are hydrogen.

8. A method according to claim 1 wherein $R_4$ is hydrogen, cyano or methyl.

9. A method according to claim 1 wherein $R_5$ is hydrogen, methyl or cyano.

10. A method according to claim 1 wherein $R_6$ is $R_{16}$-alkylene-, and $R_{16}$ is chosen from lower alkoxy, amino, lower alkylamino, di(loweralkyl)amino, carboxy, hydroxyl-, and N-heterocyclyl-.

11. A method according to claim 1 wherein $R_6$ is selected from optionally substituted lower-alkyl-, optionally substituted cyclohexyl-; phenyl substituted with hydroxy, lower-alkoxy or lower-alkyl-; benzyl-; heteroarylmethyl-; heteroarylethyl-; and heteroarylpropyl-.

12. A method according to claim 1 wherein $R_7$ is selected from optionally substituted alkyl-, optionally substituted aralkyl-, optionally substituted heteroaralkyl-, optionally substituted heteroaryl-, optionally substituted aryl-, $R_8O$— and $R_{14}$—NH—, wherein $R_8$ is chosen from optionally substituted alkyl and optionally substituted aryl and $R_{14}$ is chosen from optionally substituted alkyl and optionally substituted aryl.

13. A method according to claim 1 wherein $R_7$ is chosen from optionally substituted alkyl-; aryl-; substituted aryl-; benzyl-; heteroaryl, and heteroaryl- substituted with lower alkyl.

14. A method according to claim 1 wherein $R_7$ is p-tolyl.

15. A method according to claim 1 wherein $R_2$ and $R_{2'}$ are each attached to a stereogenic center having an R-configuration.

16. A method according to claim 1 wherein $R_6$ is aminopropyl.

17. A method according to claim 1 wherein $R_1$ is benzyl.

* * * * *